(12) United States Patent  
Brough et al.

(10) Patent No.: US 8,012,980 B2
(45) Date of Patent: Sep. 6, 2011

(54) ISOQUINOLINONE DERIVATIVES

(75) Inventors: Stephen John Brough, Loughborough (GB); Timothy Jon Luker, Loughborough (GB); Bryan Glyn Roberts, Loughborough (GB); Stephen Anthony St-Gallay, Loughborough (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 12/571,894

(22) Filed: Oct. 1, 2009

(65) Prior Publication Data

US 2010/0099665 A1  Apr. 22, 2010

Related U.S. Application Data

(60) Provisional application No. 61/101,764, filed on Oct. 1, 2008, provisional application No. 61/179,417, filed on May 19, 2009.

(51) Int. Cl.
*C07D 401/12* (2006.01)
*A61K 31/4709* (2006.01)

(52) U.S. Cl. .................. 514/253.05; 544/363

(58) Field of Classification Search .................. None
See application file for complete search history.

(56) References Cited

U.S. PATENT DOCUMENTS

2004/0044258 A1  3/2004  Shoda et al.

FOREIGN PATENT DOCUMENTS

| EP | 1484320 A1 | 12/2004 |
|---|---|---|
| WO | WO-2009/001132 A1 | 1/2000 |
| WO | WO-00/55153 A1 | 9/2000 |
| WO | WO-03/076405 A1 | 9/2003 |
| WO | WO-2005/016862 A1 | 2/2005 |
| WO | WO-2005/035503 A1 | 4/2005 |
| WO | WO-2005/054230 A1 | 6/2005 |
| WO | WO-2005/075438 A1 | 8/2005 |
| WO | WO-2006/003517 A1 | 1/2006 |
| WO | WO-2006/039718 A2 | 4/2006 |
| WO | WO-2006/067444 A1 | 6/2006 |
| WO | WO-2007/012422 A1 | 2/2007 |
| WO | WO-2007/129036 A1 | 11/2007 |
| WO | WO-2007/129040 A1 | 11/2007 |
| WO | WO-2007/129963 A1 | 11/2007 |
| WO | WO-2008/122765 A1 | 10/2008 |

OTHER PUBLICATIONS

Hanson, G. J., "Pulmonary-Allergy, Dermatological, Gastrointestinal & Arthritis: Inhibitors of p38 Kinase", Expert Opinion, 1997, vol. 7, pp. 729-733.

STN International, CAPLUS accession No. 2007:1470100, Document No. 148:100635, E.I. DuPont de Nemours and Company, "Preparation of Pyrazinones as Cellular Proliferation Inhibitors", & WO/2007149448 A2, 2007.

*Primary Examiner* — Zinna Northington Davis
(74) *Attorney, Agent, or Firm* — Connolly Bove Lodge & Hutz LLP

(57) ABSTRACT

The present invention relates to isoquinolinone derivatives of formula (I):

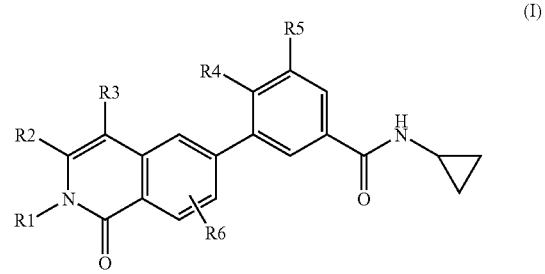

wherein are as herein defined; processes for their preparation, pharmaceutical compositions containing them and their use in therapy.

5 Claims, 6 Drawing Sheets

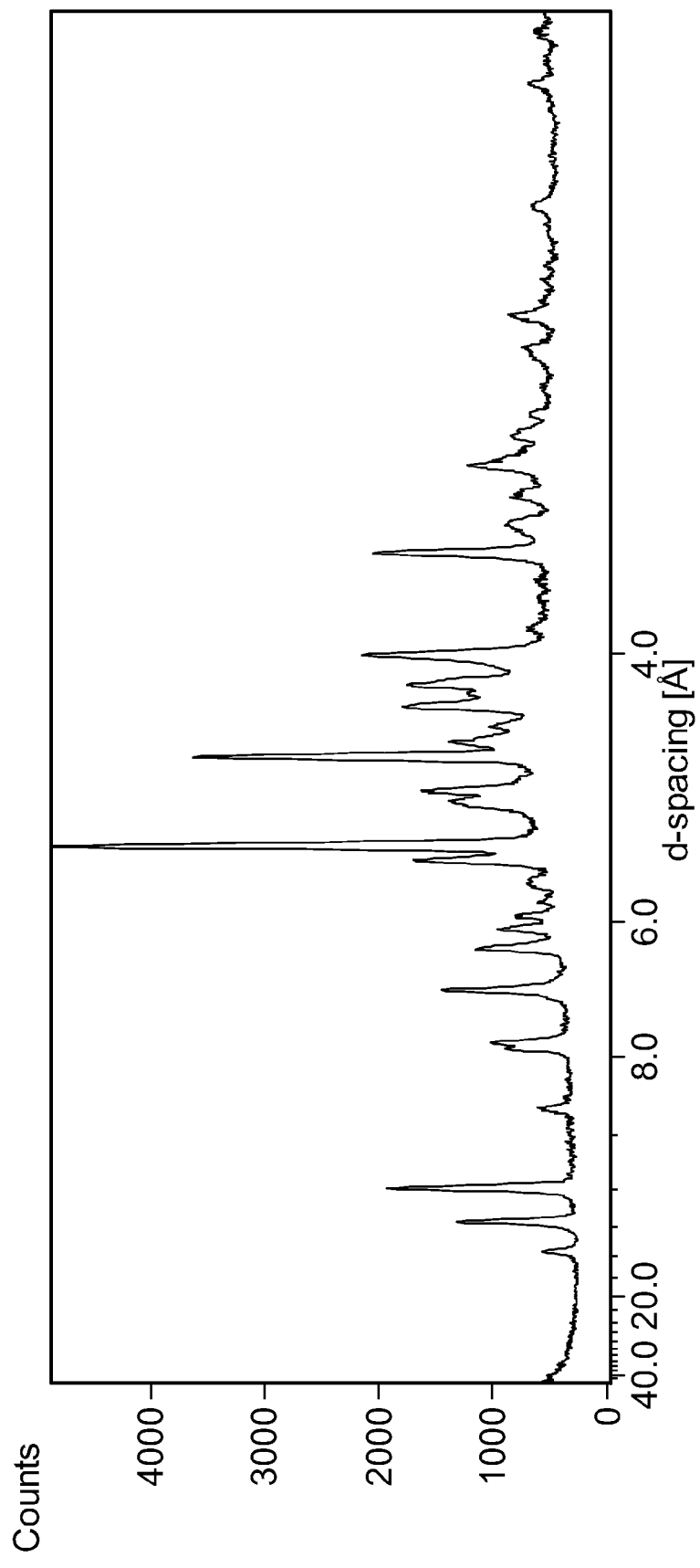
Figure 1: XRPD for Example 26 Free Base Crystalline Form A

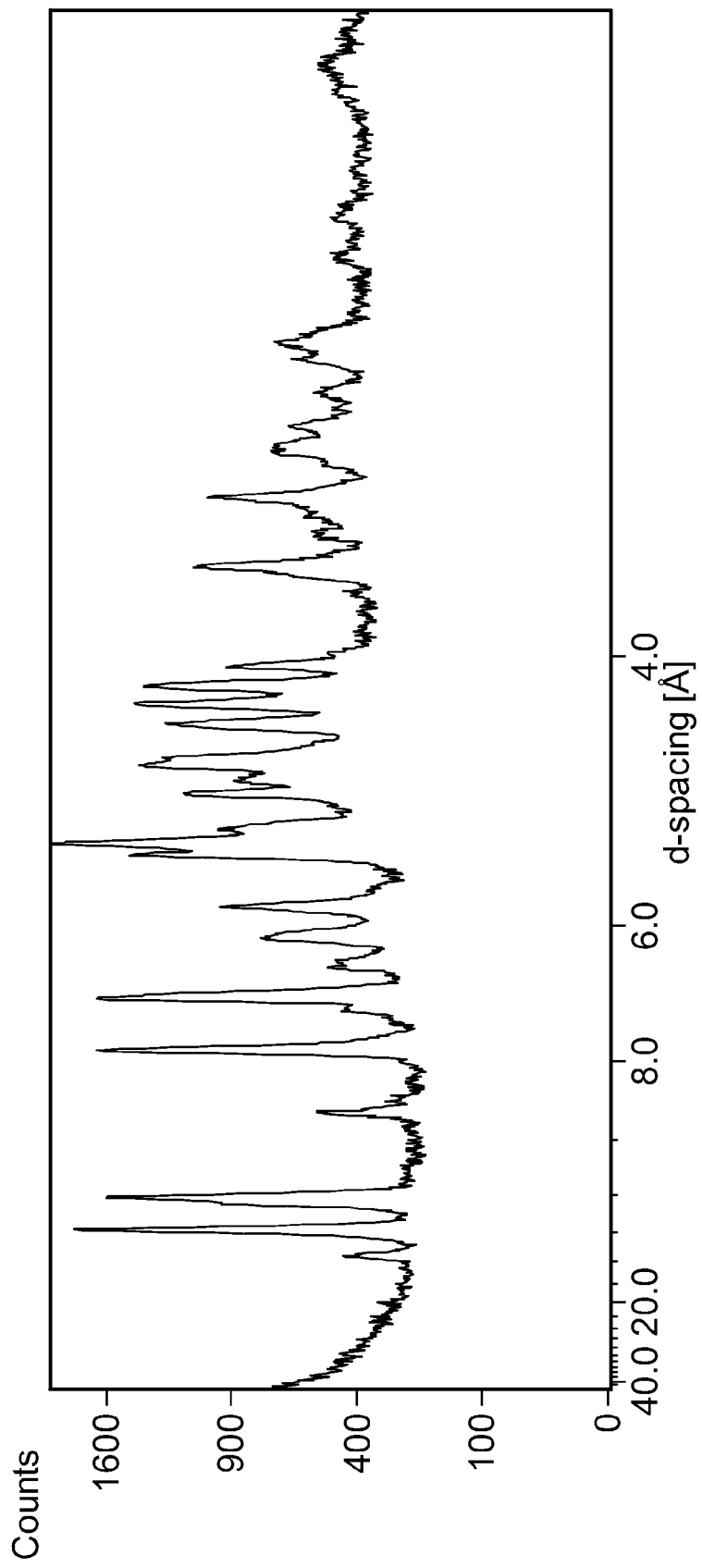

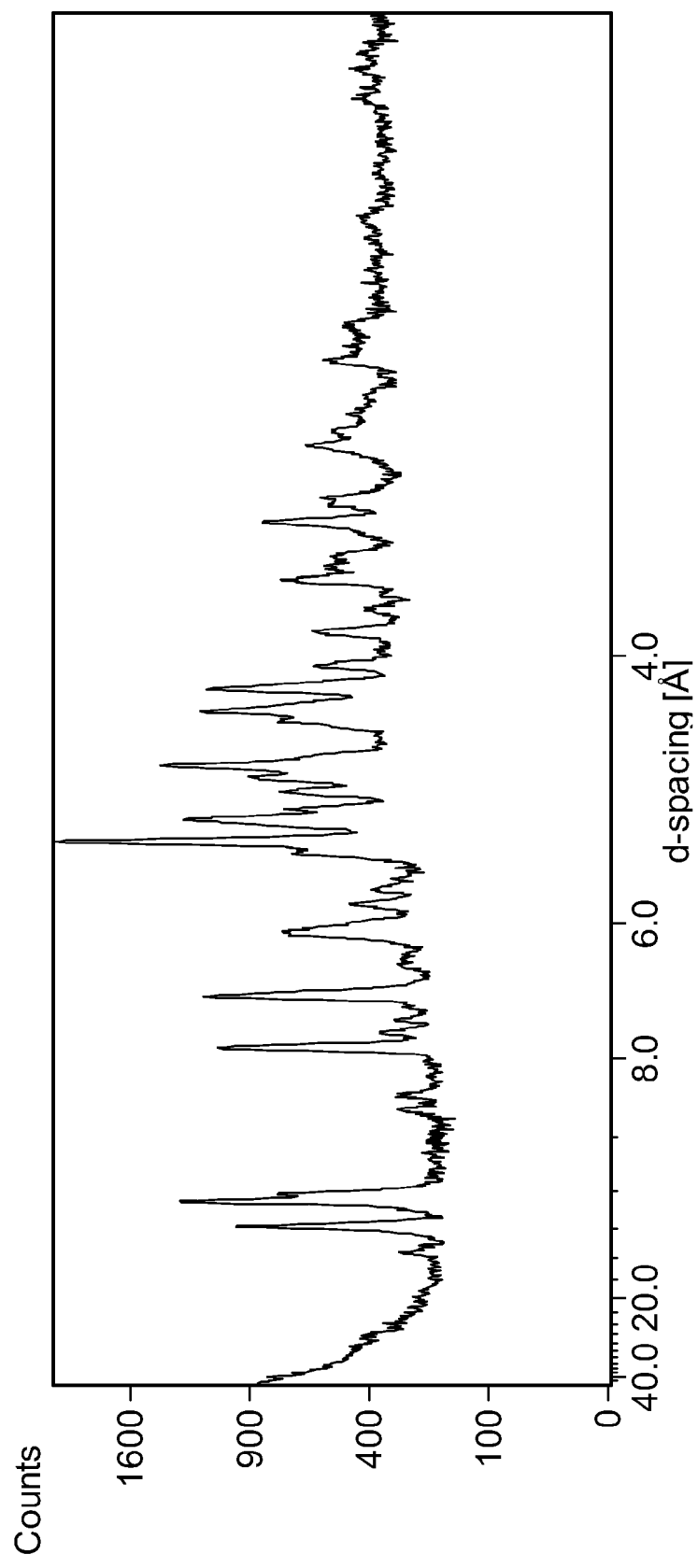
Figure 3: XRPD for Example 26 Free Base Crystalline Form C

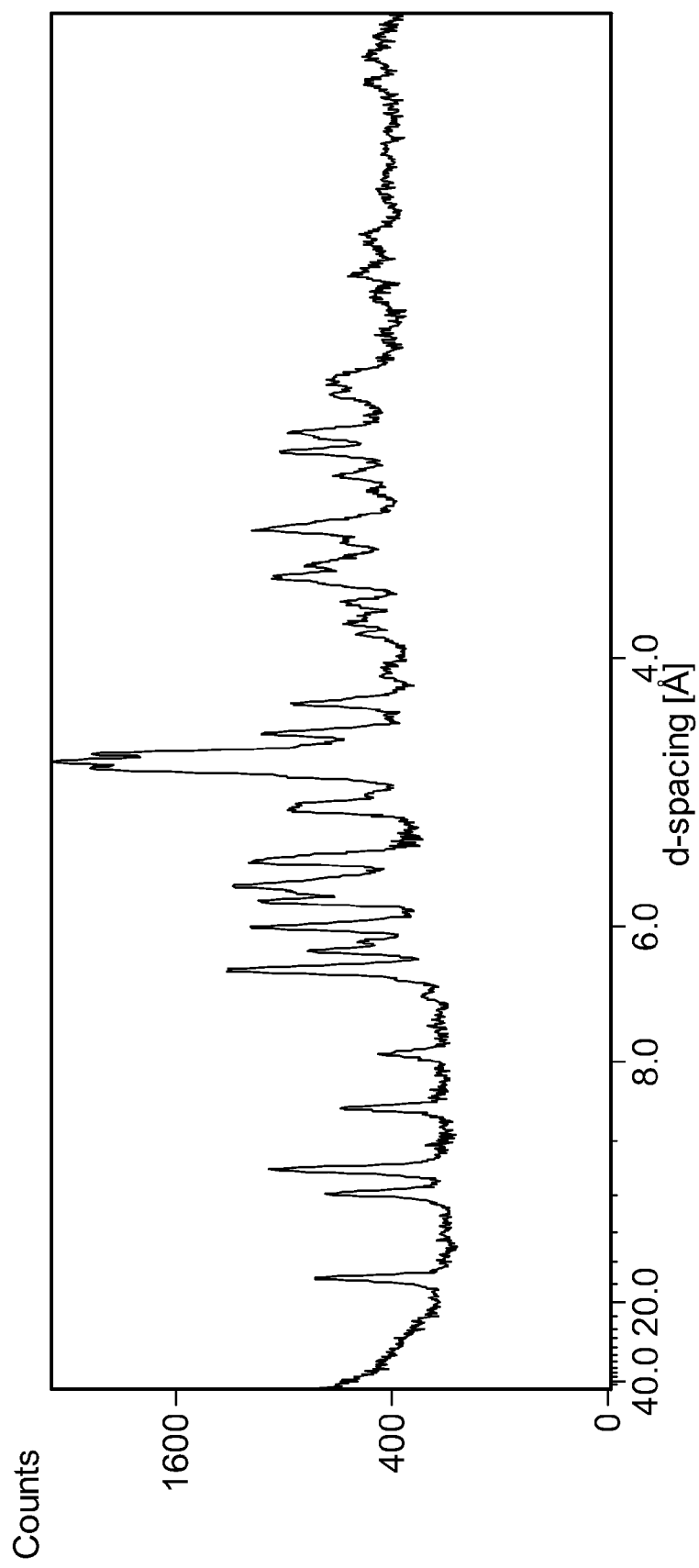
Figure 4: XRPD for Example 26 Acetate Salt Crystalline Form A

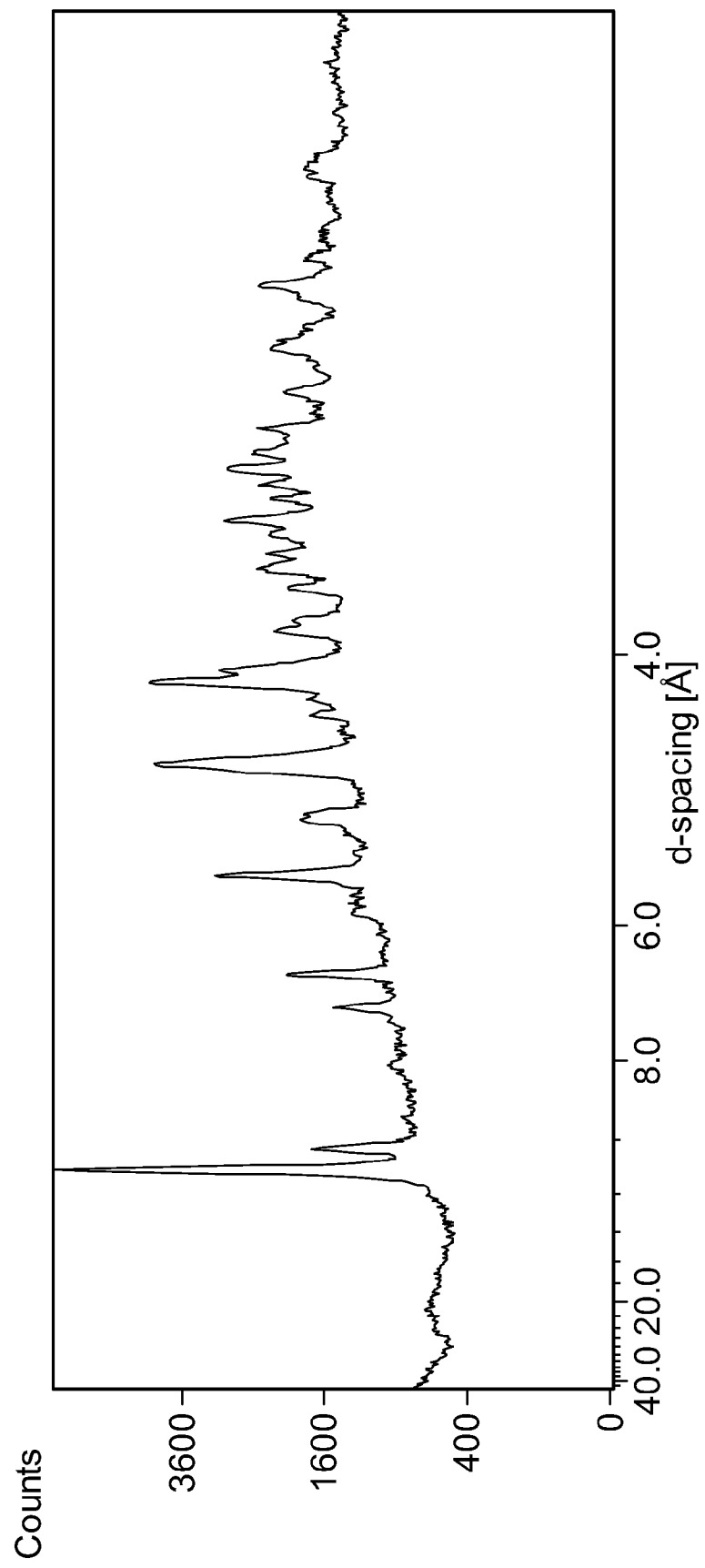
Figure 5: XRPD for Example 26 Dihydrobromide Salt Crystalline Form A

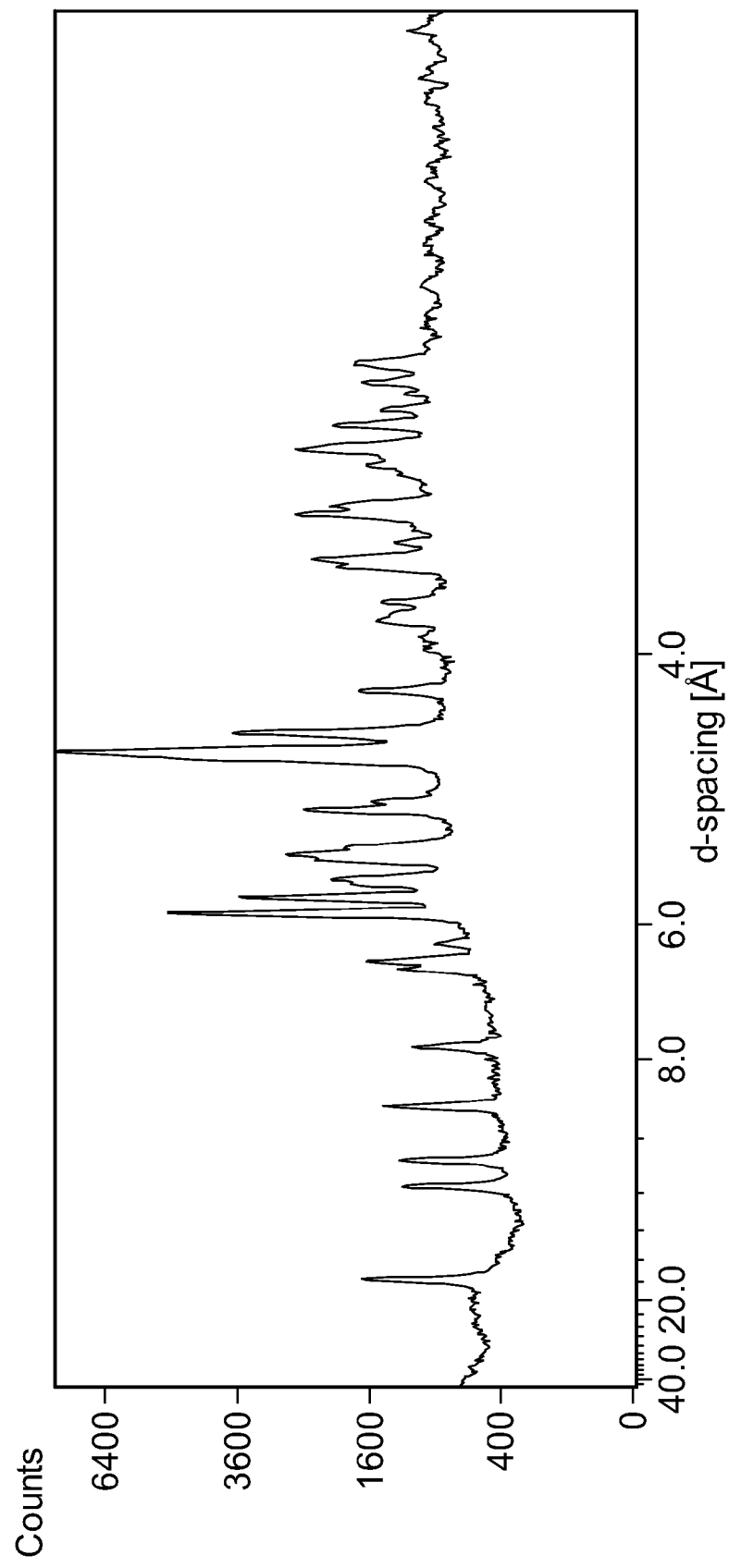
Figure 6: XRPD for Example 26 Free Base Crystalline Form D

ISOQUINOLINONE DERIVATIVES

This application claims the benefit under 35 U.S.C. 119(e) of U.S. Provisional Application No. 61/101,764, filed Oct. 1, 2008, and U.S. Provisional Application No. 61/179,417, filed May 19, 2009, both of which are herein incorporated by reference in their entirety.

The present invention relates to isoquinolinone derivatives, processes for their preparation, pharmaceutical compositions containing them and their use in therapy.

The essential function of the lungs requires a fragile structure with enormous exposure to the environment, including pollutants, microbes, allergens, and carcinogens. Host factors, resulting from interactions of lifestyle choices and genetic composition, influence the response to this exposure. Damage or infection to the lungs can give rise to a wide range of diseases of the respiratory system (or respiratory diseases). A number of these diseases are of great public health importance. Respiratory diseases include Acute Lung Injury, Acute Respiratory Distress Syndrome (ARDS), occupational lung disease, lung cancer, tuberculosis, fibrosis, pneumoconiosis, pneumonia, emphysema, Chronic Obstructive Pulmonary Disease (COPD) and asthma.

Among the most common of the respiratory diseases is asthma. Asthma is generally defined as an inflammatory disorder of the airways with clinical symptoms arising from intermittent airflow obstruction. It is characterised clinically by paroxysms of wheezing, dyspnea and cough. It is a chronic disabling disorder that appears to be increasing in prevalence and severity. It is estimated that 15% of children and 5% of adults in the population of developed countries suffer from asthma. Therapy should therefore be aimed at controlling symptoms so that normal life is possible and at the same time provide basis for treating the underlying inflammation.

COPD is a term which refers to a large group of lung diseases which can interfere with normal breathing. Current clinical guidelines define COPD as a disease state characterized by airflow limitation that is not fully reversible. The airflow limitation is usually both progressive and associated with an abnormal inflammatory response of the lungs to noxious particles and gases. The most important contributory source of such particles and gases, at least in the western world, is tobacco smoke. COPD patients have a variety of symptoms, including cough, shortness of breath, and excessive production of sputum; such symptoms arise from dysfunction of a number of cellular compartments, including neutrophils, macrophages, and epithelial cells. The two most important conditions covered by COPD are chronic bronchitis and emphysema.

Chronic bronchitis is a long-standing inflammation of the bronchi which causes increased production of mucous and other changes. The patients' symptoms are cough and expectoration of sputum. Chronic bronchitis can lead to more frequent and severe respiratory infections, narrowing and plugging of the bronchi, difficult breathing and disability.

Emphysema is a chronic lung disease which affects the alveoli and/or the ends of the smallest bronchi. The lung loses its elasticity and therefore these areas of the lungs become enlarged. These enlarged areas trap stale air and do not effectively exchange it with fresh air. This results in difficult breathing and may result in insufficient oxygen being delivered to the blood. The predominant symptom in patients with emphysema is shortness of breath.

Therapeutic agents used in the treatment of respiratory diseases include corticosteroids. Corticosteroids (also known as glucocorticosteroids or glucocorticoids) are potent anti-inflammatory agents. Whilst their exact mechanism of action is not clear, the end result of corticosteroid treatment is a decrease in the number, activity and movement of inflammatory cells into the bronchial submucosa leading to decreased airway responsiveness. Corticosteroids may also cause reduced shedding of bronchial epithelial lining, vascular permeability, and mucus secretion. Whilst corticosteroid treatment can yield important benefits, the efficacy of these agents is often far from satisfactory, particularly in COPD. Moreover, whilst the use of steroids may lead to therapeutic effects, it is desirable to be able to use steroids in low doses to minimise the occurrence and severity of undesirable side effects that may be associated with regular administration. Recent studies have also highlighted the problem of the acquisition of steroid resistance amongst patients suffering from respiratory diseases. For example, cigarette smokers with asthma have been found to be insensitive to short term inhaled corticosteroid therapy, but the disparity of the response between smokers and non-smokers appears to be reduced with high dose inhaled corticosteroid (Tomlinson et al., Thorax 2005; 60:282-287).

A further class of therapeutic agent used in the treatment of respiratory diseases are bronchodilators. Bronchodilators may be used to alleviate symptoms of respiratory diseases by relaxing the bronchial smooth muscles, reducing airway obstruction, reducing lung hyperinflation and decreasing shortness of breath. Types of bronchodilators in clinical use include $\beta_2$ adrenoceptor agonists, muscarinic receptor antagonists and methylxanthines. Bronchodilators are prescribed mainly for symptomatic relief and they are not considered to alter the natural history of respiratory diseases.

The serine/threonine kinase, p38, is a member of the stress and mitogen activated protein kinase family (SAPK/MAPK) and participates in intracellular signalling cascades involved in a number of responses associated with inflammatory processes. Four isoforms of p38 kinase are known to exist, identified as p38α, p38β, p38γ and p38δ.

The p38 pathway is activated by stress (including tobacco smoke, infections or oxidative products) and pro-inflammatory cytokines (e.g. IL-1 or TNF-α) and is involved in induction of cytokines such as TNF-α, IL-1, IL-6 and matrix metalloprotease by bacterial lipopolysaccharide (LPS). Activation of p38 by dual phosphorylation of $thr^{180}$ and $tyr^{182}$ located in the activation loop is achieved by two dual specificity upstream MAP kinase kinases (MKK); MKK3 and MKK6. In turn p38 phosphorylates numerous targets including other kinases and transcription factors. In addition to effects on transcription, p38 is involved in the control of mRNA stability of several cytokines including TNF-α, IL-3, IL-6 and IL-8. Thus through this cascade, p38 kinase is thought to play a significant role in the control of transcription and translation responsible for the induction of pro-inflammatory genes and the subsequent release of pro-inflammatory cytokines such as TNF-α from cells. This mechanism has been validated by investigation of the effects of inhibiting the p38 kinase enzyme on chronic inflammation and arthritis (Kumar et al, Nature Reviews Drug Discovery (2003) 2: 717-725). In particular, p38 kinase inhibitors have been described as potential agents for treating rheumatoid arthritis.

In addition to the links between p38 activation and chronic inflammation and arthritis, there is also data implicating a role for p38 in the pathogenesis of airway diseases in particular COPD and asthma. Stress stimuli (including tobacco smoke, infections or oxidative products) can cause inflammation within the lung environment. Inhibitors of p38 have been shown to inhibit LPS and ovalbumin induced airway TNF-α, IL-1-β, IL-6, IL-4, IL-5 and IL-13 (Haddad et al Br J Pharmacol, 2001, 132 (8), 1715; Underwood et al., Am J Physiol Lung cell Mol 200, 279, L895; Duan et al., 2005 Am J Respir Crit Care Med, 171, 571; Escott et al Br J Pharmacol., 2000, 131, 173; Underwood et al., J Pharmacol Exp Ther. 293, 281). Furthermore, they significantly inhibit neutrophilia and the release of MMP-9 in LPS, ozone or cigarette smoke models. There is also a significant body of preclinical data highlighting the potential benefits of inhibition of the p38 kinase that could be relevant in the lung (Lee et al. Immunopharmacology, 2000, 47, 185-200). Thus, therapeutic inhibition of p38 activation may be important in the regulation of airway inflammation. Efficacy is anticipated when p38 kinase inhibitors are administered either locally to the lung (for example by inhalation and intranasal delivery) or via systemic routes (for example, oral, intravenous and subcutaneous delivery).

A particular aspect of the present invention relates to pharmaceutical compositions that are formulated to allow the compounds described herein to be administered locally to the lung. Advantages associated with such inhaled drug delivery include large lung surface area for dose absorption; rapid drug absorption, rapid onset of action; avoidance of the gastrointestinal tract and first-pass metabolism, lower dose and reduced side effects.

Known inhibitors of p38 kinase have been reviewed by G. J. Hanson in Expert Opinions on Therapeutic Patents, 1997, 7, 729-733, J Hynes et al Current Topics in Medicinal chemistry 2005, 5, 967-985, C Dominguez et al in Expert Opinions on Therapeutic Patents, 2005, 15, 801-816.

The present invention provides compounds of formula (I):

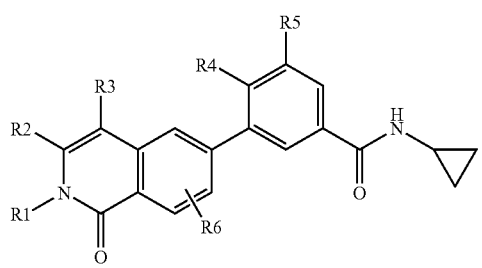

(I)

wherein:
R1 is $(C_1-C_8)$alkyl which is optionally substituted with 1, 2, 3 or 4 groups independently selected from —$(C_1-C_6)$alkyl, —$(C_1-C_6)$alkoxy, -halo, —OH, —$NH_2$, —HN$(C_1-C_6)$alkyl, —N-di-$(C_1-C_6)$alkyl, $(C_3-C_7)$cycloalkyl, —$(C_1-C_6)$alkyl-$(C_3-C_7)$cycloalkyl, —$(C_1-C_6)$alkyl-$(C_1-C_6)$alkoxy or —$(C_1-C_6)$alkyl-hydroxy, and wherein one independent —$(C_1-C_6)$alkyl R1 substituent may optionally be fused to another independent —$(C_1-C_6)$alkyl R1 substituent to form a saturated carbocyclic ring which may be optionally further substituted by 1 or 2 groups independently selected from —$(C_1-C_6)$alkoxy, -halo, —OH, —$NH_2$, —HN$(C_1-C_6)$alkyl, and —N-di-$(C_1-C_6)$alkyl;
R2 is H, halo, $(C_1-C_6)$alkyl and $(C_1-C_6)$alkoxy;
R3 is $(CH_2)_d$—Y and R3 is independently optionally substituted by one or more —$(C_1-C_6)$alkyl, —$(C_1-C_6)$alkoxy, -halo, —OH, —$NH_2$, —HN$(C_1-C_6)$alkyl, —N-di-$(C_1-C_6)$alkyl, —$(C_1-C_6)$alkyl-$NH_2$, —$(C_1-C_6)$alkyl-NH$(C_1-C_6)$alkyl, —$(C_1-C_6)$alkyl-N-di-$(C_1-C_6)$alkyl, $(C_3-C_7)$cycloalkyl, —$(C_1-C_6)$alkyl-$(C_3-C_7)$cycloalkyl, —$(C_1-C_6)$alkyl-hydroxy and —$(C_1-C_6)$alkyl-$(C_1-C_6)$alkoxy;
Y is selected from heterocycloalkyl, O-heterocycloalkyl, S—$(O)_e$-heterocycloalkyl, S—$(O)_e$—$(C_1-C_6)$alkyl-heterocycloalkyl, —$SO_2$NH—$(C_1-C_6)$alkyl and $(C_1-C_6)$alkyl;
d is 0, 1, 2 and 3;
e is 0, 1 or 2;

R4 and R5 are independently selected from H, $(C_1-C_6)$alkyl, $(C_1-C_6)$alkoxy, halo, $CF_3$, and CN;
R6 is selected from H, $(C_1-C_6)$alkyl, $(C_1-C_6)$alkoxy and halo;
heterocycloalkyl is a C- or N-linked 3 to 7 membered non-aromatic cyclic ring,
which when C-linked contains
one or two NR7 atoms, or
one NR7 atom and an S or an O atom, or
one S atom, or
one O atom,
and when N-linked contains,
one N-atom, or
one N-atom and one NR7 atom, or
one N-atom and an S or an O atom,
and which C- or N-linked 3 to 7 membered non-aromatic cyclic ring may optionally contain, where possible, 1 or 2 double bonds, and wherein any S atom in said non-aromatic cyclic ring may optionally be oxidised to SO or SO2;
R7 is H, $(C_1-C_6)$alkyl and C(O)O—$(C_1-C_6)$alkyl, wherein said $(C_1-C_6)$alkyl may be optionally substituted with $(C_1-C_6)$alkoxy, —OH, halo and $(C_3-C_7)$cycloalkyl;
or a pharmaceutically acceptable salt or N-oxide thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms. It will also be understood that is certain compounds of the present invention may exist as co-crystals with other molecules and that the present invention encompasses said co-crystals.

Certain compounds of formula (I) are capable of existing in stereoisomeric forms. It is to be understood that the present invention encompasses all geometric and optical isomers of the compounds of formula (I) and mixtures thereof including racemates. Tautomers and mixtures thereof also form an aspect of the present invention.

Further values of R1, R2, R3, R4, R5, R6, R7, d and e are as follows. Such values may be used where appropriate with any of the definitions, claims or embodiments defined hereinbefore or hereinafter.

R1 is $(C_1-C_4)$alkyl which is optionally substituted with 1, 2, 3 or 4 groups independently selected from —$(C_1-C_6)$alkyl, —$(C_1-C_6)$alkoxy, -halo, —OH, —$NH_2$, —HN$(C_1-C_6)$alkyl, —N-di-$(C_1-C_6)$alkyl, $(C_3-C_7)$cycloalkyl, —$(C_1-C_6)$alkyl-$(C_3-C_7)$cycloalkyl, —$(C_1-C_6)$alkyl-$(C_1-C_6)$alkoxy, and wherein one independent —$(C_1-C_6)$alkyl R1 substituent may optionally be fused to another independent —$(C_1-C_6)$alkyl R1 substituent to form a saturated carbocyclic ring which may be optionally further substituted.

R1 is $(C_1-C_4)$alkyl which is optionally substituted with 1, 2, 3 or 4 groups independently selected from —$(C_1-C_6)$alkyl, —$(C_1-C_6)$alkoxy, -halo, —OH, —$NH_2$, —HN$(C_1-C_6)$alkyl, —N-di-$(C_1-C_6)$alkyl, $(C_3-C_7)$cycloalkyl, —$(C_1-C_6)$alkyl-$(C_3-C_7)$cycloalkyl, —$(C_1-C_6)$alkyl-$(C_1-C_6)$alkoxy, and wherein one independent —$(C_1-C_6)$alkyl R1 substituent may optionally be fused to another independent —$(C_1-C_6)$alkyl R1 substituent to form a saturated carbocyclic ring.

R1 is $(C_1-C_4)$alkyl which is optionally substituted with 1, 2, 3 or 4 groups independently selected from —$(C_1-C_6)$alkyl, —$(C_1-C_6)$alkoxy and —OH, and wherein one independent —$(C_1-C_6)$alkyl R1 substituent may optionally be fused to another independent —(C$_1$-C$_6$)alkyl R1 substituent to form a saturated carbocyclic ring which may be optionally further substituted.

R1 is (C$_1$-C$_4$)alkyl which is optionally substituted with 1, 2, 3 or 4 groups independently selected from —(C$_1$-C$_6$)alkyl, —(C$_1$-C$_6$)alkoxy and —OH, and wherein one independent —(C$_1$-C$_6$)alkyl R1 substituent may optionally be fused to another independent —(C$_1$-C$_6$)alkyl R1 substituent to form a saturated carbocyclic ring.

R1 is (C$_1$-C$_4$)alkyl which is optionally substituted with 1, 2, 3 or 4 groups independently selected from —(C$_1$-C$_6$)alkyl, —(C$_1$-C$_6$)alkoxy and —OH, and wherein one independent methyl R1 substituent is fused to another independent methyl R1 substituent to form a cyclopropyl ring.

R1 is (C$_1$-C$_4$)alkyl which is optionally substituted with 1, 2, 3 or 4 groups independently selected from —(C$_1$-C$_6$)alkyl, —(C$_1$-C$_6$)alkoxy and —OH, and wherein one independent methyl R1 substituent is fused to another independent ethyl R1 substituent to form a cyclobutyl ring.

R1 is ethyl, propyl or butyl which is optionally substituted with 1, 2, 3 or 4 groups independently selected from —(C$_1$-C$_6$)alkyl, —(C$_1$-C$_6$)alkoxy and —OH, and wherein one independent methyl R1 substituent is fused to another independent methyl R1 substituent to form a cyclopropyl ring.

R1 is ethyl, propyl or butyl which is optionally substituted with 1, 2, 3 or 4 groups independently selected from —(C$_1$-C$_6$)alkyl, —(C$_1$-C$_6$)alkoxy and —OH, and wherein one independent methyl R1 substituent is fused to another independent methyl R1 substituent to form a cyclobutyl ring.

R1 is ethyl, propyl or butyl which is optionally substituted with 1, 2, 3 or 4 groups independently selected from methyl, ethyl, methoxy, ethoxy and —OH, and wherein one independent methyl R1 substituent is fused to another independent methyl R1 substituent to form a cyclopropyl ring.

R1 is ethyl, propyl or butyl which is optionally substituted with 1, 2, 3 or 4 groups independently selected from methyl, ethyl, methoxy, ethoxy and —OH.

R1 is propyl which is optionally substituted with 1, 2, 3 or 4 groups independently selected from methyl and —OH, and wherein one independent methyl R1 substituent is fused to another independent methyl R1 substituent to form a cyclopropyl ring.

R1 is propyl which is optionally substituted with 1, 2, 3 or 4 groups independently selected from methyl, ethyl and —OH, and wherein one independent methyl R1 substituent is fused to another independent ethyl R1 substituent to form a cyclobutyl ring.

R1 is propyl which is optionally substituted with 1, 2, 3 or 4 groups independently selected from methyl and —OH.

R1 is

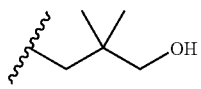

R2 is H, halo, methyl and methoxy.
R2 is H and halo.
R2 is H.
R3 is (CH$_2$)$_d$—Y and which is independently optionally substituted by one or more —(C$_1$-C$_6$)alkyl, —(C$_1$-C$_6$)alkoxy, —(C$_1$-C$_6$)alkyl-hydroxy and —(C$_1$-C$_6$)alkyl-(C$_1$-C$_6$)alkoxy.

R3 is (CH$_2$)$_d$—Y and which is independently optionally substituted by one or more methyl, methoxy, -methyl-hydroxy (i.e. —CH$_2$OH), -methyl-methoxy (i.e. —CH$_2$OCH$_3$) and amino.

R3 is (CH$_2$)$_d$—Y and which is independently optionally substituted by one or more methyl, methoxy, -methyl-hydroxy and methyl-methoxy.

R3 is (CH$_2$)$_d$—Y and which is independently optionally substituted by one or more methyl, -methyl-hydroxy and -methyl-methoxy.

R3 is

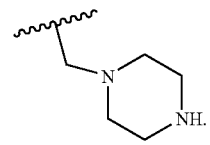

R3 is

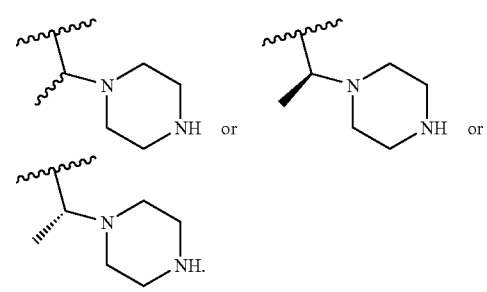

R3 is

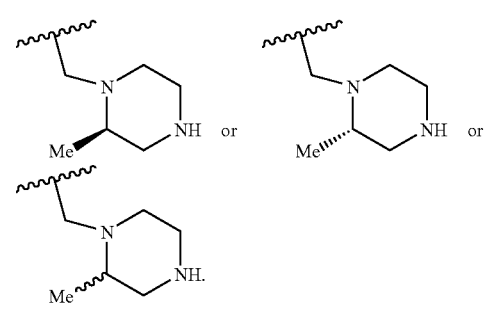

R3 is

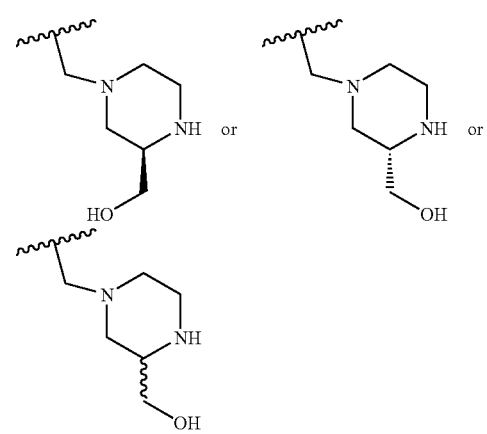

R3 is

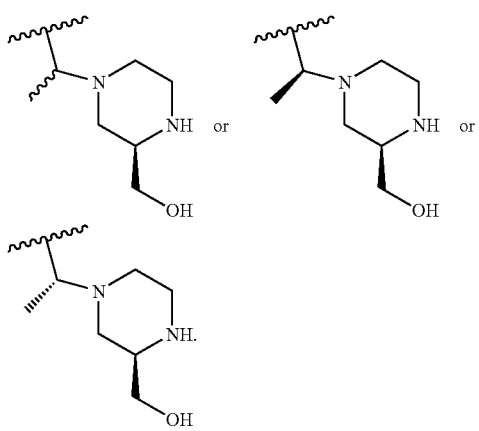

Y is selected from heterocycloalkyl, S—(O)$_e$-heterocycloalkyl and S—(O)$_e$—(C$_1$-C$_6$)alkyl-heterocycloalkyl.
Y is heterocycloalkyl.
Y is S—(O), heterocycloalkyl.
Y is azetidine, pyrrolidine, piperidine, homopiperidine, piperazine, homopiperazine, morpholine, homomorpholine and thiomorpholine.
Y is S—(O), pyrrolidine, S—(O)$_e$-piperidine, S—(O)$_e$-homopiperidine, S—(O)$_e$-piperazine and S—(O)$_e$-homopiperazine.
Y is S—(O)$_e$-homopiperazine.
Y is piperidine, homopiperidine, piperazine and homopiperazine.
Y is piperidine, piperazine and homopiperazine.
Y is piperidine.
d is selected from 0, 1, 2 and 3.
d is 0.
d is 1
d is 2
d is 3
d is 0, 1 or 2.
d is 1 or 2.
e is 0, 1 or 2.
e is 0.
e is 1.
e is 2.
R4 and R5 are independently selected from H, methyl, ethyl, methoxy, halo, CF$_3$, and CN.
R4 and R5 are independently selected from methyl, halo, CF$_3$, and CN.
R4 and R5 are independently selected from methyl and halo.
R4 and R5 are independently selected from methyl and fluoro.
R4 is methyl.
R5 is fluoro.
R6 is selected from H, methyl, methoxy and halo.
R6 is selected from H, methyl, and halo.
R6 is H.
R6 is methyl.
R6 is halo.
R7 is H and (C$_1$-C$_6$)alkyl.
R7 is H and methyl.
R7 is H.
R7 is methyl.

In one embodiment, the present invention provides a compound of formula (I) wherein
R1 is (C$_1$-C$_8$)alkyl which is optionally substituted with 1, 2, 3 or 4 groups independently selected from —(C$_1$-C$_6$)alkyl, —(C$_1$-C$_6$)alkoxy, -halo, —OH, —NH$_2$, —HN(C$_1$-C$_8$)alkyl, —N-di-(C$_1$-C$_6$)alkyl, (C$_3$-C$_7$)cycloalkyl, —(C$_1$-C$_6$)alkyl-(C$_3$-C$_7$)cycloalkyl, —(C$_1$-C$_6$)alkyl-(C$_1$-C$_6$)alkoxy, and wherein one independent —(C$_1$-C$_6$)alkyl R1 substituent may optionally be fused to another independent —(C$_1$-C$_6$)alkyl R1 substituent to form a saturated carbocyclic ring;
R2 is H, halo, (C$_1$-C$_6$)alkyl and (C$_1$-C$_6$)alkoxy;
R3 is (CH$_2$)$_d$—Y and R3 is independently optionally substituted by one or more —(C$_1$-C$_6$)alkyl, —(C$_1$-C$_6$)alkoxy, -halo, —OH, —NH$_2$, —HN(C$_1$-C$_8$)alkyl, —N-di-(C$_1$-C$_6$)alkyl, —(C$_3$-C$_7$)cycloalkyl, —(C$_1$-C$_6$)alkyl-(C$_3$-C$_7$)cycloalkyl, —(C$_1$-C$_6$)alkyl-hydroxy and —(C$_1$-C$_8$)alkyl-(C$_1$-C$_6$)alkoxy;
Y is selected from heterocycloalkyl, O-heterocycloalkyl, S—(O)$_e$-heterocycloalkyl and (C$_1$-C$_6$)alkyl;
d is 0, 1, 2 and 3;
e is 0, 1 or 2;
R4 and R5 are independently selected from H, (C$_1$-C$_6$)alkyl, (C$_1$-C$_6$)alkoxy, halo, CF$_3$, and CN;
R6 is selected from H, (C$_1$-C$_6$)alkyl, (C$_1$-C$_6$)alkoxy and halo;
heterocycloalkyl is a C- or N-linked 3 to 7 membered non-aromatic cyclic ring,
which when C-linked contains
one or two NR7 atoms, or
one NR7 atom and an S or an O atom, or
one S atom, or
one O atom,
and when N-linked contains,
one N-atom, or
one N-atom and one NR7 atom, or
one N-atom and an S or an O atom,
and which C- or N-linked 3 to 7 membered non-aromatic cyclic ring may optionally contain, where possible, 1 or 2 double bonds, and wherein any S atom in said non-aromatic cyclic ring may optionally be oxidised to SO or SO2;
R7 is H, (C$_1$-C$_6$)alkyl and C(O)O—(C$_1$-C$_6$)alkyl, wherein said (C$_1$-C$_6$)alkyl may be optionally substituted with (C$_1$-C$_6$)alkoxy, —OH, halo and (C$_3$-C$_7$)cycloalkyl;
or a pharmaceutically acceptable salt or N-oxide thereof.

In one embodiment, the present invention provides a compound of formula (I), wherein:
R1 is (C$_1$-C$_8$)alkyl which is optionally substituted with 1, 2, 3 or 4 groups independently selected from —(C$_1$-C$_6$)alkyl, —(C$_1$-C$_6$)alkoxy, -halo, —OH, —NH$_2$, —HN(C$_1$-C$_6$)alkyl, —N-di-(C$_1$-C$_6$)alkyl, (C$_3$-C$_7$)cycloalkyl, —(C$_1$-C$_6$)alkyl-(C$_3$-C$_7$)cycloalkyl, —(C$_1$-C$_6$)alkyl-(C$_1$-C$_6$)alkoxy or —(C$_1$-C$_6$)alkyl-hydroxy, and wherein one independent —(C$_1$-C$_6$)alkyl R1 substituent may optionally be fused to another independent —(C$_1$-C$_6$)alkyl R1 substituent to form a saturated carbocyclic ring which may be optionally further substituted;
R2 is H, halo, (C$_1$-C$_6$)alkyl and (C$_1$-C$_6$)alkoxy;
R3 is (CH$_2$)$_d$—Y and R3 is independently optionally substituted by one or more —(C$_1$-C$_6$)alkyl, —(C$_1$-C$_6$)alkoxy, -halo, —OH, —NH$_2$, —HN(C$_1$-C$_6$)alkyl, (C$_3$-C$_7$)cycloalkyl, —(C$_1$-C$_6$)alkyl-(C$_3$-C$_7$)cycloalkyl, —(C$_1$-C$_6$)alkyl-hydroxy and —(C$_1$-C$_6$)alkyl-(C$_1$-C$_6$)alkoxy;
Y is selected from heterocycloalkyl, O-heterocycloalkyl, S—(O)$_e$-heterocycloalkyl, S—(O)$_e$—(C$_1$-C$_6$)alkyl-heterocycloalkyl, —SO$_2$NH—(C$_1$-C$_6$)alkyl and (C$_1$-C$_6$)alkyl;
d is 0, 1, 2 and 3;
e is 0, 1 or 2;

R4 and R5 are independently selected from H, $(C_1-C_6)$alkyl, $(C_1-C_6)$alkoxy, halo, $CF_3$, and CN;
R6 is selected from H, $(C_1-C_6)$alkyl, $(C_1-C_6)$alkoxy and halo;
heterocycloalkyl is a C- or N-linked 3 to 7 membered non-aromatic cyclic ring, containing from 1 to 2 NR7 atoms, or one NR7 atom and an S or an O atom, or one S atom, or one O atom; optionally containing, where possible, 1 or 2 double bonds, and wherein any S atom in a heterocycloalkyl group atom may optionally be oxidised to SO or SO2.
R7 is H, $(C_1-C_6)$alkyl and $C(O)O-(C_1-C_6)$alkyl, wherein said $(C_1-C_6)$alkyl may be optionally substituted with $(C_1-C_6)$alkoxy, —OH, halo and $(C_3-C_7)$cycloalkyl;
or a pharmaceutically acceptable salt or N-oxide thereof.

In the above embodiment where R1 is substituted with one independent —$(C_1-C_6)$alkyl R1 substituent fused to another independent —$(C_1-C_6)$alkyl R1 substituent to form a saturated carbocyclic ring which may be optionally further substituted, the saturated carbocyclic ring may for example be optionally further substituted with 1 or 2 groups independently selected from —$(C_1-C_6)$alkoxy, -halo, —OH, —$NH_2$, —$HN(C_1-C_8)$alkyl, and —N-di-$(C_1-C_6)$alkyl. Moreover, it will be understood that in the above embodiment where heterocycloalkyl is a N-linked 3 to 7 membered non-aromatic cyclic ring containing from 1 to 2 NR7 atoms, one of the NR7 atoms will be the N ring atom at which the ring is linked to the structure of formula (I) and at this N atom the group R7 is absent.

In another embodiment, the present invention provides a compound of formula (I), wherein
R1 is $(C_1-C_8)$alkyl which is optionally substituted with 1, 2, 3 or 4 groups independently selected from —$(C_1-C_6)$alkyl, —$(C_1-C_6)$alkoxy, -halo, —OH, —$NH_2$, —$HN(C_1-C_6)$alkyl, $(C_3-C_7)$cycloalkyl, —$(C_1-C_8)$alkyl-$(C_3-C_7)$cycloalkyl, —$(C_1-C_6)$alkyl-$(C_1-C_6)$alkoxy, and wherein one independent —$(C_1-C_6)$alkyl R1 substituent may optionally be fused to another independent —$(C_1-C_6)$alkyl R1 substituent to form a saturated carbocyclic ring which may be optionally further substituted;
R2 is H, halo, $(C_1-C_6)$alkyl and $(C_1-C_6)$alkoxy;
R3 is $(CH_2)_d$—Y and R3 is independently optionally substituted by one or more —$(C_1-C_6)$alkyl, —$(C_1-C_6)$alkoxy, -halo, —OH, —$NH_2$, —$HN(C_1-C_8)$alkyl, $(C_3-C_7)$cycloalkyl, —$(C_1-C_6)$alkyl-$(C_3-C_7)$cycloalkyl, —$(C_1-C_6)$alkyl-hydroxy and —$(C_1-C_6)$alkyl-$(C_1-C_6)$alkoxy;
Y is selected from heterocycloalkyl, O-heterocycloalkyl, S—$(O)_e$-heterocycloalkyl and $(C_1-C_6)$alkyl;
d is 0, 1, 2 and 3;
e is 0, 1 or 2;
R4 and R5 are independently selected from H, $(C_1-C_6)$alkyl, $(C_1-C_6)$alkoxy, halo, $CF_3$, and CN;
R6 is selected from H, $(C_1-C_6)$alkyl, $(C_1-C_6)$alkoxy and halo;
heterocycloalkyl is a C- or N-linked 3 to 7 membered non-aromatic cyclic ring, containing from 1 to 2 NR7 atoms, or one NR7 atom and an S or an O atom, or one S atom, or one O atom; optionally containing, where possible, 1 or 2 double bonds, and wherein any S atom in a heterocycloalkyl group atom may optionally be oxidised to SO or $SO_2$;
R7 is H, $(C_1-C_6)$alkyl and $C(O)O-(C_1-C_6)$alkyl, wherein said $(C_1-C_6)$alkyl may be optionally substituted with $(C_1-C_6)$alkoxy, —OH, halo and $(C_3-C_7)$cycloalkyl;
or a pharmaceutically acceptable salt or N-oxide thereof.

In the above embodiment where R1 is substituted with one independent —$(C_1-C_6)$alkyl R1 substituent fused to another independent —$(C_1-C_6)$alkyl R1 substituent to form a saturated carbocyclic ring which may be optionally further substituted, the saturated carbocyclic ring may for example be optionally further substituted with 1 or 2 groups independently selected from —$(C_1-C_6)$alkoxy, -halo, —OH, —$NH_2$, —$HN(C_1-C_6)$alkyl, and —N-di-$(C_1-C_6)$alkyl. Moreover, it will be understood that in the above embodiment where heterocycloalkyl is a N-linked 3 to 7 membered non-aromatic cyclic ring containing from 1 to 2 NR7 atoms, one of the NR7 atoms will be the N ring atom at which the ring is linked to the structure of formula (I) and at this N atom the group R7 is absent.

In one embodiment, the present invention provides a compound of formula (IA)

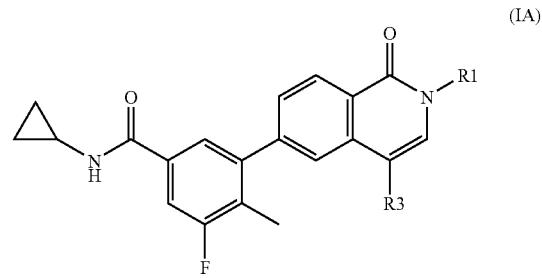

(IA)

wherein
R1 is ethyl, propyl or butyl which is optionally substituted with 1, 2, 3 or 4 groups independently selected from methyl, ethyl, methoxy, ethoxy and —OH, and wherein one independent methyl R1 substituent may or may not be fused to another independent methyl R1 substituent to form a cyclopropyl ring;
R3 is $(CH_2)_d$—Y and R3 is independently optionally substituted by one or more groups selected from methyl, methoxy, -methyl-hydroxy, methyl-methoxy and amino;
d is 1; and Y is a heterocycloalkyl selected from piperidine, piperazine and homopiperazine
or a pharmaceutically acceptable salt or N-oxide thereof.

In one embodiment, the present invention provides a compound of formula (IA), wherein
R1 is propyl which is optionally substituted with 1, 2, 3 or 4 groups independently selected from methyl and —OH;
R3 is $(CH_2)_d$—Y and R3 is independently optionally substituted by one or more groups selected from methyl, and -methyl-hydroxy;
d is 1; and Y is an N-linked heterocycloalkyl which is homopiperazine;
or a pharmaceutically acceptable salt or N-oxide thereof.

In one embodiment, the present invention provides a compound of formula (IA), wherein
R1 is propyl which is optionally substituted with 1, 2, 3 or 4 groups independently selected from methyl and —OH;
R3 is $(CH_2)_d$—Y and R3 is independently optionally substituted by one or more groups selected from methyl, and -methyl-hydroxy;
d is 1; and Y is an N-linked heterocycloalkyl which is piperazine;
or a pharmaceutically acceptable salt or N-oxide thereof.

In one embodiment, the present invention provides a compound which is N-Cyclopropyl-3-fluoro-5-[2-(3-hydroxy-2,2-dimethylpropyl)-4-{[2-methylpiperazin-1-yl]methyl}-1-oxo-1,2-dihydroisoquinolin-6-yl]-4-methylbenzamide or a pharmaceutically acceptable salt or N-oxide thereof. In one aspect of this embodiment, the compound is a racemic mixture of R and S enantiomers. In a further aspect, the compound is the S enantiomer, i.e. N-Cyclopropyl-3-fluoro-5-[2-(3-hydroxy-2,2-dimethylpropyl)-4-{[(2S)-2-methylpiperazin-1-yl]methyl}-1-oxo-1,2- dihydroisoquinolin-6-yl]-4-methylbenzamide. In another aspect, the compound is the R enantiomer, i.e. N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide.

In one embodiment the present invention provides a compound which is N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide or a pharmaceutically acceptable salt or N-oxide thereof.

In another embodiment, the present invention provides a compound which is N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide acetate. In one aspect of this embodiment, the stoichiometric ratio of acetate to N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide is 1:1.

In other aspects of the above embodiment the stoichiometric ratio of acetate to N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide may vary as in some circumstances the respective molecules may form co-crystals wherein the components utilise intermolecular interactions to combine and form crystalline material. When co-crystals are present the stoichiometric ratio of acetate to N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide may for example be in the range of from 1:3 to 3:1, and in one aspect the ratio is 3:2. Where co-crystals are present all the acetate and N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide molecules may be combined as co-crystals or alternatively the material may comprise a mixture of co-crystals and acetate salt.

In another embodiment, the present invention provides a compound which is N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide dihydrobromide.

In one embodiment, the present invention provides a compound which is N-Cyclopropyl-3-fluoro-5-[2-(3-hydroxy-2,2-dimethylpropyl)-1-oxo-4-(1-piperazin-1-ylethyl)-1,2-dihydroisoquinolin-6-yl]-4-methylbenzamide or a pharmaceutically acceptable salt or N-oxide thereof. In one aspect of this embodiment, the compound is a racemic mixture of R and S enantiomers. In a further aspect, the compound is the S enantiomer, i.e. N-Cyclopropyl-3-fluoro-5-{2-(3-hydroxy-2,2-dimethylpropyl)-1-oxo-4-[(1S)-1-piperazin-1-ylethyl]-1,2-dihydroisoquinolin-6-yl}-4-methylbenzamide. In another aspect, the compound is the R enantiomer, i.e. N-Cyclopropyl-3-fluoro-5-{2-(3-hydroxy-2,2-dimethylpropyl)-1-oxo-4-[(1R)-1-piperazin-1-ylethyl]-1,2-dihydroisoquinolin-6-yl}-4-methylbenzamide.

In one embodiment the present invention provides a compound which is N-Cyclopropyl-3-fluoro-5-[2-(3-hydroxy-2,2-dimethylpropyl)-4-{1-[(3R)-3-(hydroxymethyl)piperazin-1-yl]ethyl}-1-oxo-1,2-dihydroisoquinolin-6-yl]-4-methylbenzamide or a pharmaceutically acceptable salt or N-oxide thereof. In one aspect of this embodiment, the compound is a mixture of the SR and RR diastereomers. In a further aspect, the compound is the SR diastereomer, i.e. N-Cyclopropyl-3-fluoro-5-[2-(3-hydroxy-2,2-dimethylpropyl)-4-{(1S)-1-[(3R)-3-(hydroxymethyl)piperazin-1-yl]ethyl}-1-oxo-1,2-dihydroisoquinolin-6-yl]-4-methylbenzamide. In another aspect, the compound is the RR diastereomer, i.e. N-Cyclopropyl-3-fluoro-5-[2-(3-hydroxy-2,2-dimethylpropyl)-4-{(1R)-1-[(3R)-3-(hydroxymethyl)piperazin-1-yl]ethyl}-1-oxo-1,2-dihydroisoquinolin-6-yl]-4-methylbenzamide In one embodiment, the present invention provides a compound of formula (IA) wherein wherein
R1 is ethyl, propyl or butyl which is optionally substituted with 1, 2, 3 or 4 groups independently selected from methyl, ethyl, methoxy, ethoxy and —OH, and wherein one independent methyl R1 substituent may be fused to another independent methyl R1 substituent to form a cyclopropyl ring;
R3 is $(CH_2)_d$—Y and R3 is independently optionally substituted by one or more groups selected from methyl, methoxy, -methyl-hydroxy, -methyl-methoxy, amino;
d is 0;
Y is S—(O)e-heterocycloalkyl wherein the heterocycloalkyl is an N-linked heterocycle selected from piperazine and homopiperazine; and
e is 2
or a pharmaceutically acceptable salt or N-oxide thereof.

In one embodiment, the present invention provides a compound which is N-Cyclopropyl-3-[4-(1,4-diazepan-1-ylsulfonyl)-2-(3-hydroxy-2,2-dimethylpropyl)-1-oxo-1,2-dihydroisoquinolin-6-yl]-5-fluoro-4-methylbenzamide or a pharmaceutically acceptable salt or N-oxide thereof.

In one embodiment, the present invention provides a compound of formula (IA), wherein
R1 is propyl which is optionally substituted with 1, 2, 3 or 4 groups independently selected from methyl and —OH;
R3 is $(CH_2)_d$—Y and R3 is independently optionally substituted by one or more groups selected from methyl and -methyl-hydroxy;
d is 0; Y is S—$(O)_e$-heterocycloalkyl wherein the heterocycloalkyl is an N-linked piperidine or pyrrolidine, which piperidine or pyrrolidine is further substituted with a substituent selected from amino, —NH($C_1$-$C_3$)alkyl, —N-di-($C_1$-$C_3$)alkyl$_2$, —($C_1$-$C_3$)alkyl-NH$_2$, —($C_1$-$C_3$)alkyl-NH($C_1$-$C_3$)alkyl, —($C_1$-$C_3$)alkyl-N-di-($C_1$-$C_6$)alkyl; and
e is 2;
or a pharmaceutically acceptable salt or N-oxide thereof.

In one embodiment, the present invention provides a compound of formula (IA), wherein
R1 is ethyl, propyl or butyl which is optionally substituted with 1, 2, 3 or 4 groups independently selected from methyl, ethyl, methoxy, ethoxy and —OH, and wherein one independent methyl R1 substituent may be fused to another independent methyl R1 substituent to form a cyclopropyl ring;
R3 is $(CH_2)_d$—Y and R3 is independently optionally substituted by one or more groups selected from methyl, -methyl-hydroxy, amino, —NH($C_1$-$C_3$)alkyl, —N-di-($C_1$-$C_3$)alkyl$_2$, —($C_1$-$C_3$)alkyl-NH$_2$, —($C_1$-$C_3$)alkyl-NH($C_1$-$C_3$)alkyl, —($C_1$-$C_3$)alkyl-N-di-($C_1$-$C_6$)alkyl;
d is 0; Y is S—$(O)_e$-heterocycloalkyl wherein the heterocycloalkyl is a C-linked heterocycloalkyl selected from piperidine and pyrrolidine; and
e is 0, 1 or 2;
or a pharmaceutically acceptable salt or N-oxide thereof.

In one embodiment, the present invention provides a compound of formula (IA), wherein
R1 is propyl which is optionally substituted with 1, 2, 3 or 4 groups independently selected from methyl and —OH;
R3 is $(CH_2)_d$—Y and R3 is independently optionally substituted by one or more groups selected from methyl, -methyl-hydroxy, amino, —NH($C_1$-$C_3$)alkyl, —N-di-($C_1$-$C_3$)alkyl$_2$, —(C₁-C₃)alkyl-NH₂, —(C₁-C₃)alkyl-NH(C₁-C₃)alkyl, —(C₁-C₃)alkyl-N-di-(C₁-C₆)alkyl;

d is 0; Y is S—(O)$_e$-heterocycloalkyl wherein the heterocycloalkyl is a C-linked heterocycloalkyl selected from piperidine and pyrrolidine; and e is 0, 1 or 2;

or a pharmaceutically acceptable salt or N-oxide thereof.

In one embodiment, the present invention provides a compound which is N-Cyclopropyl-3-fluoro-5-[2-(3-hydroxy-2,2-dimethylpropyl)-1-oxo-4-(piperidin-4-ylsulfanyl)-1,2-dihydroisoquinolin-6-yl]-4-methylbenzamide or a pharmaceutically acceptable salt or N-oxide thereof.

In one embodiment, the present invention provides a compound of formula (I) selected from:

N-Cyclopropyl-3-fluoro-5-[2-(3-hydroxy-2,2-dimethylpropyl)-1-oxo-4-(piperazin-1-ylmethyl)-1,2-dihydroisoquinolin-6-yl]-4-methylbenzamide;

N-Cyclopropyl-3-fluoro-5-{2-(3-hydroxy-2,2-dimethylpropyl)-4-[(4-methyl-1,4-diazepan-1-yl)methyl]-1-oxo-1,2-dihydroisoquinolin-6-yl}-4-methylbenzamide;

N-Cyclopropyl-3-fluoro-5-(4-(((3S)-3-(hydroxymethyl)piperazin-1-yl)methyl)-2-(3-hydroxypropyl)-1-oxo-1,2-dihydroisoquinolin-6-yl)-4-methylbenzamide;

N-Cyclopropyl-3-fluoro-5-(2-(3-hydroxypropyl)-4-(((3S)-3-methylpiperazin-1-yl)methyl)-1-oxo-1,2-dihydroisoquinolin-6-yl)-4-methylbenzamide;

N-Cyclopropyl-3-fluoro-5-(2-(2-hydroxyethyl)-1-oxo-4-(piperazin-1-ylmethyl)-1,2-dihydroisoquinolin-6-yl)-4-methylbenzamide;

N-Cyclopropyl-3-fluoro-5-(2-(2-hydroxyethyl)-4-(((3S)-3-methylpiperazin-1-yl)methyl)-1-oxo-1,2-dihydroisoquinolin-6-yl)-4-methylbenzamide;

N-Cyclopropyl-3-fluoro-5-(2-(2-hydroxyethyl)-4-((4-methyl-1,4-diazepan-1-yl)methyl)-1-oxo-1,2-dihydroisoquinolin-6-yl)-4-methylbenzamide;

N-Cyclopropyl-3-fluoro-5-{2-(4-hydroxybutyl)-4-[(4-methyl-1,4-diazepan-1-yl)methyl]-1-oxo-1,2-dihydroisoquinolin-6-yl}-4-methylbenzamide;

N-Cyclopropyl-3-fluoro-5-{2-[(3S)-3-hydroxybutyl]-1-oxo-4-(piperazin-1-ylmethyl)-1,2-dihydroisoquinolin-6-yl}-4-methylbenzamide;

N-Cyclopropyl-3-fluoro-5-[2-(3-hydroxypropyl)-1-oxo-4-(piperazin-1-ylmethyl)-1,2-dihydroisoquinolin-6-yl]-4-methylbenzamide;

N-Cyclopropyl-3-fluoro-5-(2-(3-hydroxy-2,2-dimethylpropyl)-4-(((3R)-3-(hydroxymethyl)piperazin-1-yl)methyl)-1-oxo-1,2-dihydroisoquinolin-6-yl)-4-methylbenzamide;

N-Cyclopropyl-3-fluoro-5-(2-((1-(hydroxymethyl)cyclopropyl)methyl)-4-(((3R)-3-(hydroxymethyl)piperazin-1-yl)methyl)-1-oxo-1,2-dihydroisoquinolin-6-yl)-4-methylbenzamide;

N-Cyclopropyl-3-fluoro-5-(4-((3-(hydroxymethyl)piperazin-1-yl)methyl)-2-(((3R)-3-methoxypropyl)-1-oxo-1,2-dihydroisoquinolin-6-yl)-4-methylbenzamide;

N-Cyclopropyl-3-fluoro-5-(2-(3-hydroxy-3-methylbutyl)-4-(((3R)-3-(hydroxymethyl)piperazin-1-yl)methyl)-1-oxo-1,2-dihydroisoquinolin-6-yl)-4-methylbenzamide;

N-Cyclopropyl-3-fluoro-5-(2-((1-(hydroxymethyl)cyclopropyl)methyl)-4-(((3S)-3-(hydroxymethyl)piperazin-1-yl)methyl)-1-oxo-1,2-dihydroisoquinolin-6-yl)-4-methylbenzamide;

N-Cyclopropyl-3-fluoro-5-(2-((1-(hydroxymethyl)cyclopropyl)methyl)-4-(((2R)-2-(hydroxymethyl)piperazin-1-yl)methyl)-1-oxo-1,2-dihydroisoquinolin-6-yl)-4-methylbenzamide;

N-Cyclopropyl-3-fluoro-5-(2-(3-hydroxy-2,2-dimethylpropyl)-4-(((3S)-3-(hydroxymethyl)piperazin-1-yl)methyl)-1-oxo-1,2-dihydroisoquinolin-6-yl)-4-methylbenzamide;

N-Cyclopropyl-3-fluoro-5-{2-[(2S)-3-hydroxy-2-methylpropyl]-1-oxo-4-(piperazin-1-ylmethyl)-1,2-dihydroisoquinolin-6-yl}-4-methylbenzamide;

N-Cyclopropyl-3-fluoro-5-[2-{1-(hydroxymethyl)cyclopropyl]methyl}-1-oxo-4-(piperazin-1-ylmethyl)-1,2-dihydroisoquinolin-6-yl]-4-methylbenzamide;

N-Cyclopropyl-3-fluoro-5-{2-[(2R)-3-hydroxy-2-methylpropyl]-1-oxo-4-(piperazin-1-ylmethyl)-1,2-dihydroisoquinolin-6-yl}-4-methylbenzamide;

N-Cyclopropyl-3-fluoro-5-[2-(3-hydroxy-2,2-dimethylpropyl)-4-{[(2S)-2-(hydroxymethyl)piperazin-1-yl]methyl}-1-oxo-1,2-dihydroisoquinolin-6-yl]-4-methylbenzamide;

N-Cyclopropyl-3-fluoro-5-[2-(3-hydroxy-2,2-dimethylpropyl)-4-{[(2R)-2-(hydroxymethyl)piperazin-1-yl]methyl}-1-oxo-1,2-dihydroisoquinolin-6-yl]-4-methylbenzamide;

N-Cyclopropyl-3-[4-(1,4-diazepan-1-ylmethyl)-2-(3-hydroxy-2,2-dimethylpropyl)-1-oxo-1,2-dihydroisoquinolin-6-yl]-5-fluoro-4-methylbenzamide;

N-Cyclopropyl-3-fluoro-5-{2-(3-hydroxy-2,2-dimethylpropyl)-4-[(4-methylpiperazin-1-yl)methyl]-1-oxo-1,2-dihydroisoquinolin-6-yl}-4-methylbenzamide;

3-[4-{[(3S)-3-Aminopiperidin-1-yl]methyl}-2-(3-hydroxy-2,2-dimethylpropyl)-1-oxo-1,2-dihydroisoquinolin-6-yl]-N-cyclopropyl-5-fluoro-4-methylbenzamide;

N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide;

N-Cyclopropyl-3-fluoro-5-[2-{[1-(hydroxymethyl)cyclobutyl]methyl}-1-oxo-4-(piperazin-1-ylmethyl)-1,2-dihydroisoquinolin-6-yl]-4-methylbenzamide;

N-Cyclopropyl-3-fluoro-5-[2-(3-hydroxy-2,2-dimethylpropyl)-4-{[(2S)-2-methylpiperazin-1-yl]methyl}-1-oxo-1,2-dihydroisoquinolin-6-yl]-4-methylbenzamide;

N-Cyclopropyl-3-fluoro-5-[2-(3-hydroxy-2,2-dimethylpropyl)-4-{[(3S)-3-methylpiperazin-1-yl]methyl}-1-oxo-1,2-dihydroisoquinolin-6-yl]-4-methylbenzamide hydrochloride;

3-[4-{[(3R)-3-aminopiperidin-1-yl]methyl}-2-(3-hydroxy-2,2-dimethylpropyl)-1-oxo-1,2-dihydroisoquinolin-6-yl]-N-cyclopropyl-5-fluoro-4-methylbenzamide;

3-{4-[(4-amino-4-methylpiperidin-1-yl)methyl]-2-(3-hydroxy-2,2-dimethylpropyl)-1-oxo-1,2-dihydroisoquinolin-6-yl}-N-cyclopropyl-5-fluoro-4-methylbenzamide;

N-Cyclopropyl-3-fluoro-5-[2-(3-hydroxy-2,2-dimethylpropyl)-4-{[4-(3-hydroxypropyl)piperazin-1-yl]methyl}-1-oxo-1,2-dihydroisoquinolin-6-yl]-4-methylbenzamide;

N-Cyclopropyl-3-fluoro-5-(2-{[1-(hydroxymethyl)cyclopropyl]methyl}-4-{[(2R)-2-methylpiperazin-1-yl]methyl}-1-oxo-1,2-dihydroisoquinolin-6-yl)-4-methylbenzamide;

N-Cyclopropyl-3-fluoro-5-(2-{[1-(hydroxymethyl)cyclopropyl]methyl}-4-{[(3S)-3-methylpiperazin-1-yl]methyl}-1-oxo-1,2-dihydroisoquinolin-6-yl)-4-methylbenzamide;

N-Cyclopropyl-3-fluoro-5-(2-[3-hydroxy-2-(hydroxymethyl)propyl]-4-{[(3S)-3-methylpiperazin-1-yl]methyl}-1-oxo-1,2-dihydroisoquinolin-6-yl)-4-methylbenzamide;

N-Cyclopropyl-3-fluoro-5-(2-[3-hydroxy-2-(hydroxymethyl)-2-methylpropyl]-4-{[(3S)-3-methylpiperazin-1-yl]methyl}-1-oxo-1,2-dihydroisoquinolin-6-yl)-4-methylbenzamide;

N-Cyclopropyl-3-fluoro-5-(2-[2-(hydroxymethyl)-2-methylbutyl]-4-{[(3S)-3-methylpiperazin-1-yl]methyl}-1-oxo-1,2-dihydroisoquinolin-6-yl)-4-methylbenzamide;

N-Cyclopropyl-3-fluoro-5-[2-(3-hydroxy-2,2-dimethylpropyl)-1-oxo-4-(1-piperazin-1-ylethyl)-1,2-dihydroisoquinolin-6-yl]-4-methylbenzamide racemate;

N-Cyclopropyl-3-fluoro-5-{2-(3-hydroxy-2,2-dimethylpropyl)-1-oxo-4-[(1S)-1-piperazin-1-ylethyl]-1,2-dihydroisoquinolin-6-yl}-4-methylbenzamide N-Cyclopropyl-3-fluoro-5-{2-(3-hydroxy-2,2-dimethylpropyl)-1-oxo-4-[(1R)-1-piperazin-1-ylethyl]-1,2-dihydroisoquinolin-6-yl}-4-methylbenzamide 3-{4-[1-(4-Amino-4-methylpiperidin-1-yl)ethyl]-2-(3-hydroxy-2,2-dimethylpropyl)-1-oxo-1,2-dihydroisoquinolin-6-yl}-N-cyclopropyl-5-fluoro-4-methylbenzamide 3-[4-{1-[(3R)-3-Aminopiperidin-1-yl]ethyl}-2-(3-hydroxy-2,2-dimethylpropyl)-1-oxo-1,2-dihydroisoquinolin-6-yl]-N-cyclopropyl-5-fluoro-4-methylbenzamide;

N-Cyclopropyl-3-{4-[1-(1,4-diazepan-1-yl)ethyl]-2-(3-hydroxy-2,2-dimethylpropyl)-1-oxo-1,2-dihydroisoquinolin-6-yl}-5-fluoro-4-methylbenzamide;

N-Cyclopropyl-3-fluoro-5-[2-(3-hydroxy-2,2-dimethylpropyl)-4-{(1S)-1-[(3R)-3-(hydroxymethyl)piperazin-1-yl]ethyl}-1-oxo-1,2-dihydroisoquinolin-6-yl]-4-methylbenzamide N-Cyclopropyl-3-fluoro-5-[2-(3-hydroxy-2,2-dimethylpropyl)-4-{(1R)-1-[(3R)-3-(hydroxymethyl)piperazin-1-yl]ethyl}-1-oxo-1,2-dihydroisoquinolin-6-yl]-4-methylbenzamide N-Cyclopropyl-3-[4-(1,4-diazepan-1-ylsulfonyl)-2-(3-hydroxy-2,2-dimethylpropyl)-1-oxo-1,2-dihydroisoquinolin-6-yl]-5-fluoro-4-methylbenzamide;

N-Cyclopropyl-3-[2-(cyclopropylmethyl)-1-oxo-4-(piperazin-1-ylsulfonyl)-1,2-dihydroisoquinolin-6-yl]-5-fluoro-4-methylbenzamide;

N-Cyclopropyl-3-{2-(cyclopropylmethyl)-4-[(4-methylpiperazin-1-yl)-sulfonyl]-1-oxo-1,2-dihydroisoquinolin-6-yl}-5-fluoro-4-methylbenzamide;

N-Cyclopropyl-3-fluoro-5-[2-(3-hydroxy-2,2-dimethylpropyl)-4-{[(3R)-3-(hydroxymethyl)piperazin-1-yl]sulfonyl}-1-oxo-1,2-dihydroisoquinolin-6-yl]-4-methylbenzamide;

3-{4-[(4-Aminopiperidin-1-yl)sulfonyl]-2-(cyclopropylmethyl)-1-oxo-1,2-dihydroisoquinolin-6-yl}-N-cyclopropyl-5-fluoro-4-methylbenzamide;

N-cyclopropyl-3-[2-(cyclopropylmethyl)-4-(1,4-diazepan-1-ylsulfonyl)-1-oxo-1,2-dihydroisoquinolin-6-yl]-5-fluoro-4-methylbenzamide;

N-cyclopropyl-3-[2-(cyclopropylmethyl)-4-{[4-(methylamino)piperidin-1-yl]sulfonyl}-1-oxo-1,2-dihydroisoquinolin-6-yl]-5-fluoro-4-methylbenzamide;

3-[4-{[(3S)-3-Aminopyrrolidin-1-yl]sulfonyl}-2-(3-hydroxy-2,2-dimethylpropyl)-1-oxo-1,2-dihydroisoquinolin-6-yl]-N-cyclopropyl-5-fluoro-4-methylbenzamide;

3-[4-{[(3R)-3-Aminopyrrolidin-1-yl]sulfonyl}-2-(3-hydroxy-2,2-dimethylpropyl)-1-oxo-1,2-dihydroisoquinolin-6-yl]-N-cyclopropyl-5-fluoro-4-methylbenzamide;

3-[4-{[(2R)-2-(aminomethyl)pyrrolidin-1-yl]sulfonyl}-2-(3-hydroxy-2,2-dimethylpropyl)-1-oxo-1,2-dihydroisoquinolin-6-yl]-N-cyclopropyl-5-fluoro-4-methylbenzamide;

N-cyclopropyl-3-[4-{[2-(dimethylamino)ethyl]sulfamoyl}-2-(3-hydroxy-2,2-dimethylpropyl)-1-oxo-1,2-dihydroisoquinolin-6-yl]-5-fluoro-4-methylbenzamide;

N-cyclopropyl-3-[4-(1,4-diazepan-1-ylmethyl)-2-{1-(hydroxymethyl)cyclopropyl]methyl}-1-oxo-1,2-dihydroisoquinolin-6-yl]-5-fluoro-4-methylbenzamide;

N-Cyclopropyl-3-fluoro-5-[2-(3-hydroxy-2,2-dimethylpropyl)-1-oxo-4-(piperidin-4-ylsulfanyl)-1,2-dihydroisoquinolin-6-yl]-4-methylbenzamide;

N-Cyclopropyl-3-fluoro-5-[2-(3-hydroxy-2,2-dimethylpropyl)-1-oxo-4-(piperidin-4-ylsulfinyl)-1,2-dihydroisoquinolin-6-yl]-4-methylbenzamide;

N-Cyclopropyl-3-fluoro-5-[2-(3-hydroxy-2,2-dimethylpropyl)-1-oxo-4-(piperidin-4-ylsulfonyl)-1,2-dihydroisoquinolin-6-yl]-4-methylbenzamide;

N-Cyclopropyl-3-[2-(cyclopropylmethyl)-1-oxo-4-(piperidin-4-ylsulfanyl)-1,2-dihydroisoquinolin-6-yl]-5-fluoro-4-methylbenzamide;

N-Cyclopropyl-3-[2-(cyclopropylmethyl)-1-oxo-4-(piperidin-4-ylsulfonyl)-1,2-dihydroisoquinolin-6-yl]-5-fluoro-4-methylbenzamide;

N-Cyclopropyl-3-fluoro-5-(2-{[1-(hydroxymethyl)cyclopropyl]methyl}-1-oxo-4-{[(3R)-piperidin-3-ylmethyl]sulfanyl}-1,2-dihydroisoquinolin-6-yl)-4-methylbenzamide;

N-Cyclopropyl-3-fluoro-5-[2-{[1-(hydroxymethyl)cyclopropyl]methyl}-1-oxo-4-(piperidin-4-ylsulfanyl)-1,2-dihydroisoquinolin-6-yl]-4-methylbenzamide;

N-Cyclopropyl-3-fluoro-5-{2-(3-hydroxy-2,2-dimethylpropyl)-1-oxo-4-[(3R)-pyrrolidin-3-ylsulfanyl]-1,2-dihydroisoquinolin-6-yl}-4-methylbenzamide;

N-Cyclopropyl-3-fluoro-5-{2-[3-hydroxy-2-(hydroxymethyl)-2-methylpropyl]-1-oxo-4-(piperidin-4-ylsulfanyl)-1,2-dihydroisoquinolin-6-yl}-4-methylbenzamide; and N-Cyclopropyl-3-fluoro-5-[2-(3-hydroxy-2,2-dimethylpropyl)-4-{[(2S,4S)-2-(hydroxymethyl)piperidin-4-yl]sulfanyl}-1-oxo-1,2-dihydroisoquinolin-6-yl]-4-methylbenzamide; or a pharmaceutically acceptable salt or N-oxide thereof.

In the present specification, where a compound is referred to as having a specific stereochemical configuration it will be understood that the stereoisomer referred to may exist as a mixture with one or more of the other stereoisomers that the compound may form.

In a further embodiment, the present invention provides compounds of formula (I) which are optically pure. In the present specification the term optically pure is defined in terms of enantiomeric excess (e.e.), and diastereomeric excess (d.e.), which are calculated from the ratio of the difference between the amounts of the respective enantiomers/diastereomers present and the sum of these amounts, expressed as a percentage. To illustrate, a preparation containing 95% of one enantiomer and 5% of another enantiomer has an enantiomeric excess (e.e.) of 90% [i.e. (95−5)/(95+5)× 100]. Diasteriomeric excess is defined by analogy to enantiomeric excess. Optically pure compounds according to the present invention have an e.e. of at least 90%. In an embodiment of the invention, optically pure compounds have an e.e. of at least 95%. In a further embodiment of the invention, optically pure compounds have an e.e. of at least 98%. Where the compound has diastereomers, optically pure compounds have an e.e. of at least 90% and a diastereomeric excess (d.e.) of at least 90%. In an embodiment of the invention, optically pure compounds have an e.e. of at least 95% and a d.e. of at least 95%. In a further embodiment of the invention, optically pure compounds have an e.e. of at least 98% and a d.e. of at least 98%.

In one embodiment, the present invention provides optically pure N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide or a pharmaceutically acceptable salt or N-oxide thereof.

DEFINITIONS

In the context of the present specification, where it is stated that a group may be optionally substituted by one or more substituents the group may be unsubstituted or substituted; when substituted the group will generally be substituted with 1, 2, 3 or 4 substituents.

Unless otherwise stated, halo is Cl, F, Br or I;

Unless otherwise stated, cycloalkyl is a non-aromatic carbocyclic ring containing the requisite number of carbon atoms, optionally containing, where possible, up to 3 double bonds, and optionally substituted with 1 to 3 substituents selected from $(C_1-C_6)$alkyl, $(C_1-C_6)$alkoxy, —OH, —CN and halo, and wherein each substituent may be the same or different. Examples of suitable cycloalkyl groups include cyclopropyl, cyclobutyl, cyclopentyl, cyclohexyl, cycloheptyl, cyclopentene, cyclopenta-1,3-diene, cyclohexene and cyclohexa-1,4-diene (optionally substituted as stated above).

Examples of suitable heterocycloalkyl groups include oxiranyl, aziridinyl, azetidinyl, tetrahydrofuranyl, pyrrolidinyl, tetrahydropyranyl, piperidinyl, N-methylpiperidinyl, azepinyl, homopiperidinyl, piperazinyl, homopiperazinyl, 1,2,3,6-tetrahydropyridinyl and 1,2,3,4-tetrahydropyridinyl (optionally substituted as stated above).

Unless otherwise stated alkyl and alkoxy groups containing the requisite number of carbon atoms can be branched or unbranched. Examples of suitable alkyl groups include methyl, ethyl, n-propyl, i-propyl, n-butyl, sec-butyl and t-butyl. Examples of suitable alkoxy groups include methoxy (—OCH$_3$), ethoxy (—OCH$_2$CH$_3$), n-propoxy, i-propoxy, n-butoxy, sec-butoxy and t-butoxy.

Unless otherwise stated the alkyl groups within a —N-di-$(C_1-C_6)$alkyl group may be the same or different.

For the avoidance of doubt, the substituents on an R3 group may be either on the Y portion or the $(CH_2)_d$-portion of the R3 group.

The term 'C-linked', such as in 'C-linked heterocycloalkyl', means that the heterocycloalkyl group is joined via a ring carbon atom.

The term 'N-linked', such as in 'N-linked heterocycloalkyl', or 'N-linked 3 to 7 membered non-aromatic cyclic ring' means that the heterocycloalkyl group is joined via a ring nitrogen atom.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, tosylates, benzenesulfonates, maleates, fumarates, xinafoates, p-acetamidobenzoates, succinates, ascorbates, oleates, bisulfates, furoates, propionates, stearates, isethionates and the like.

In one embodiment, pharmaceutically acceptable salts may include salts of pharmaceutically acceptable organic acids, especially carboxylic and sulfonic acids, including, but not limited to, acetate, adipate, alginate, ascorbate, aspartate, benzenesulfonate (besylate), benzoate, butyrate, camphorate, camphorsulfonate, camsylate, citrate, p-chlorobenzenesulfonate, cyclopentate, 2,5-dichlorobesylate, digluconate, edisylate, esylate, fumarate, formate, gluconate, glucoheptanoate, glutamate, glutarate, glycerophosphate, glycolate, heptanoate, hexanoate, hippurate, 2-hydroxyethane sulfonate, lactate, lactobionate, laurate, malate, maleate, malonate, mandelate, methanesulfonate, 2-naphthalenesulfonate, napsylate, nicotinate, orotate, oxalate, pantothenate, pamoate, pamoic, pectinate, 3-phenylpropionate, pivalate, propionate, pivalate, saccharin, salicylate, stearate, succinate, tartrate, trans-cinnamate, trifluoroacetate, xinafoate, xylate (p-xylene-2-sulfonic acid), undecanoate; and of inorganic acids such as hydrobromide (e.g. monohydrobromide and dihydrobromide), hydrochloride (e.g. monohydrochloride and dihydrochloride), hydroiodide, sulphate, bisulfate, phosphate, nitrate, hemisulfate, thiocyanate, persulfate, phosphoric and sulfonic acids.

Salts which are not pharmaceutically acceptable may still be valuable as intermediates. Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in The Practice of Medicinal Chemistry, $2^{nd}$ Ed. pp 561-585 (2003) and in F. J. Leinweber, Drug Metab. Res., 18, 379. (1987).

The compounds of the invention can exist in both unsolvated and solvated forms. The term 'solvate' is used herein to describe a molecular complex comprising the compound of is the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application of adaptation of known methods (e.g. asymmetric synthesis).

The skilled person will recognise that the compounds of the invention may be prepared, in known manner, in a variety of ways. The routes below are merely illustrative of some of the methods that can be employed for the synthesis of compounds of formula (I).

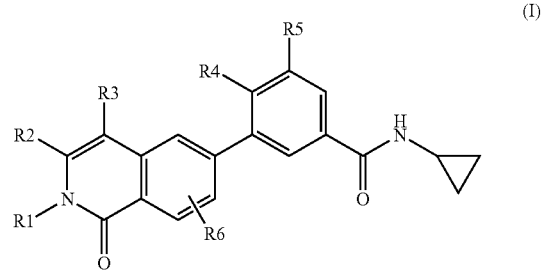

(I)

A compound of formula (I), or a pharmaceutically-acceptable salt thereof, wherein R1, R2, R3, R4, R5 and R6 are as previously defined, may be prepared as shown in Scheme 1 below.

Scheme 1

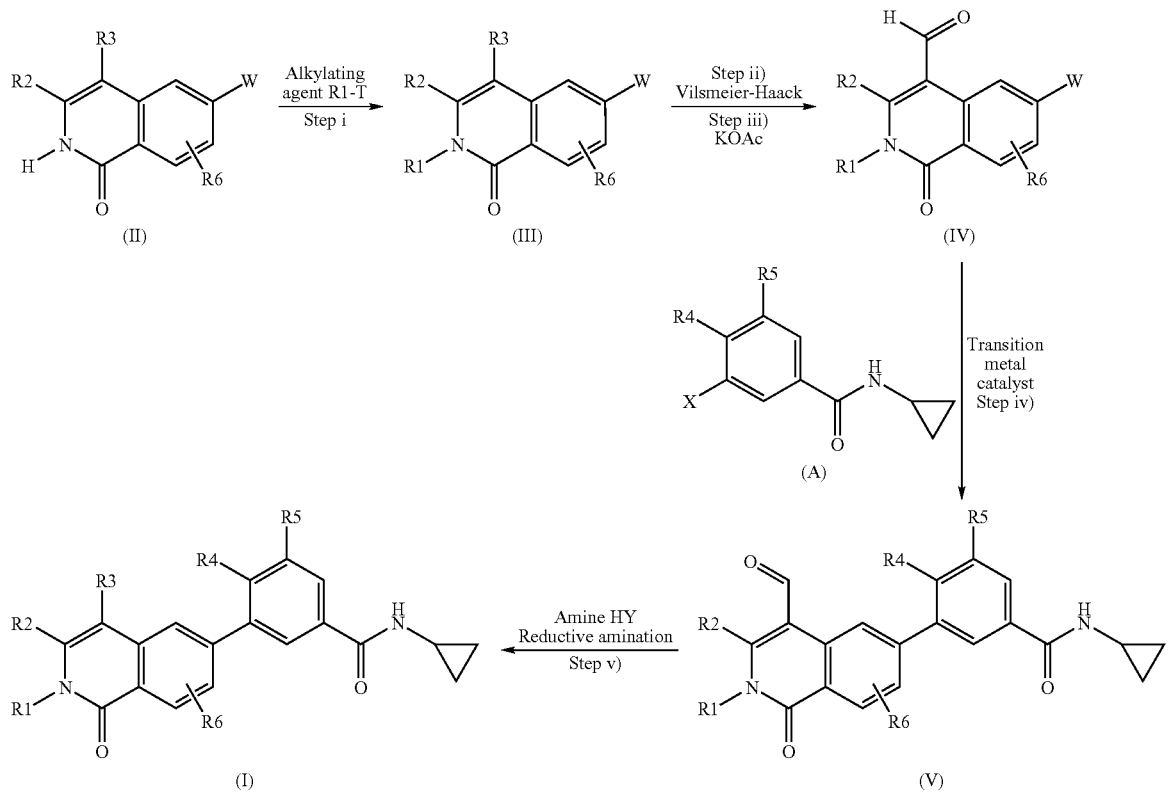

Scheme 1 Step i)

A compound of formula (III), wherein R1, R2, R3 and R6 are as previously defined in formula (I), wherein W is a leaving group such as a halide (for example bromide or iodide) or a sulfonate ester (for example a trifluoromethane sulfonate) or a boronate ester or boronic acid, may be prepared by treating a compound of formula (II) with a compound of formula R1T in an inert solvent in the presence of a base at a temperature of −20° C. to is 150° C.

Typically, the reaction is carried out where T is iodide, bromide, chloride, mesylate or tosylate, W is a leaving group such as a halide, for example bromide or iodide, and the base is sodium hydride, potassium carbonate or cesium carbonate and the reaction is carried out in N,N-dimethylformamide or 1-methyl-2-pyrrolidinone at 100° C.

Scheme 1 Step ii)

A compound of formula (IV) wherein R1, R2 and R6 are as previously defined in formula (I), and W is as described above, may be prepared from a compound of formula (III) where R3 is H by first reacting a formamide such as N,N-dimethylformamide or N-phenyl-N-methylformamide with an activating agent such as phosphorous oxychloride or oxalyl chloride in a solvent at a temperature of −20° C. to 80° C. followed by treatment with a compound of formula (III) at a temperature of 25° C. to 100° C. Preferably the reaction is carried out with N,N-dimethylformamide and phosphorous oxychloride in N,N-dimethyl formamide at 0° C. then heated at 80° C. in the presence of (III). Alternatively the reaction can be carried out using (chloromethylene)dimethylammonium chloride in N,N-dimethyl formamide at 80° C. in the presence of (III).

Scheme 1 Step iii)

It will be recognised by the skilled person that during the preparation of compounds of formula (IV) from compounds of formula (III), concomminant chlorination of hydroxyl and protected hydroxyl substituents (such as tert-butyldimethyl-silyl protected) within R1 can occur. Subsequent treatment of these compounds with, for example, sodium or potassium acetate at a temperature of 25° C. to 150° C. in a solvent such as N,N-dimethylformamide, DMSO or 1-methyl-2-pyrrolidinone will form a protected alcohol within R1 in the form of an O-Acetate. For example, R1=CH$_2$C(Me)$_2$CH$_2$OSiMe$_2$$^t$Bu is transformed in Scheme 1 Step ii) to R1=CH$_2$C(Me)$_2$CH$_2$Cl and thus in Scheme 1 Step iii) this is converted to R1=CH$_2$C(Me)$_2$CH$_2$OAc.

Scheme 1 Step iv)

A compound of formula (V) may be prepared by treating a compound of formula (IV), wherein R1, R2 and R6 are as previously defined in formula (I), and W is a leaving group such as a halide (for example bromide or iodide) or an sulfonate ester (for example a trifluoromethane sulfonate) or a boronate ester or boronic acid, with a compound of formula (A), wherein R4 and R5 are as previously defined in formula (I), and wherein X is a leaving group such as a halide (for example bromide or iodide) or a sulfonate ester (for example a trifluoromethane sulfonate) or a boronate ester or boronic acid. The reaction may be carried out in the presence of a transition metal catalyst such as tetrakis(triphenylphosphine)palladium(0) or 1,1-bis(di-tert-butylphosphino)ferrocene palladium dichloride (Pd-118) in an inert solvent such as N,N-dimethylformamide or 1-methyl-2-pyrrolidinone at a temperature of 0° C. to 150° C. in the presence of a base such as potassium carbonate.

Typically, the reaction is carried out where W is bromide and X is B(OH)$_2$ or 4,4,5,5-tetramethyl-[1,3,2]dioxaborolane and a temperature at 70° C.-80° C. in the presence of 1,1-bis (di-tert-butylphosphino)ferrocene palladium dichloride (Pd-118).

Scheme 1 Step v)

A compound of formula (I) wherein R1, R2, R3, R4, R5 and R6 are as previously defined may be prepared by a reductive amination reaction between compounds of formula (V) and a primary or secondary amine HY. The reductive amination is carried out in the presence of suitable reducing agent such as sodium cyanoborohydride, sodium triacetoxyborohydride or sodium borohydride, either neat or in a solvent such as methanol, ethanol, 1,2-dichloroethane or dichloromethane. The reactions may proceed either alone or in combination with acetic acid or titanium(IV) isopropoxide. Typically the reaction is carried out using sodium triacetoxyborohydride at room temperature.

A compound of formula (I), or a pharmaceutically-acceptable salt thereof, wherein R1, R2, R3, R4, R5 and R6 are as previously defined, may be prepared as shown in Scheme 2.

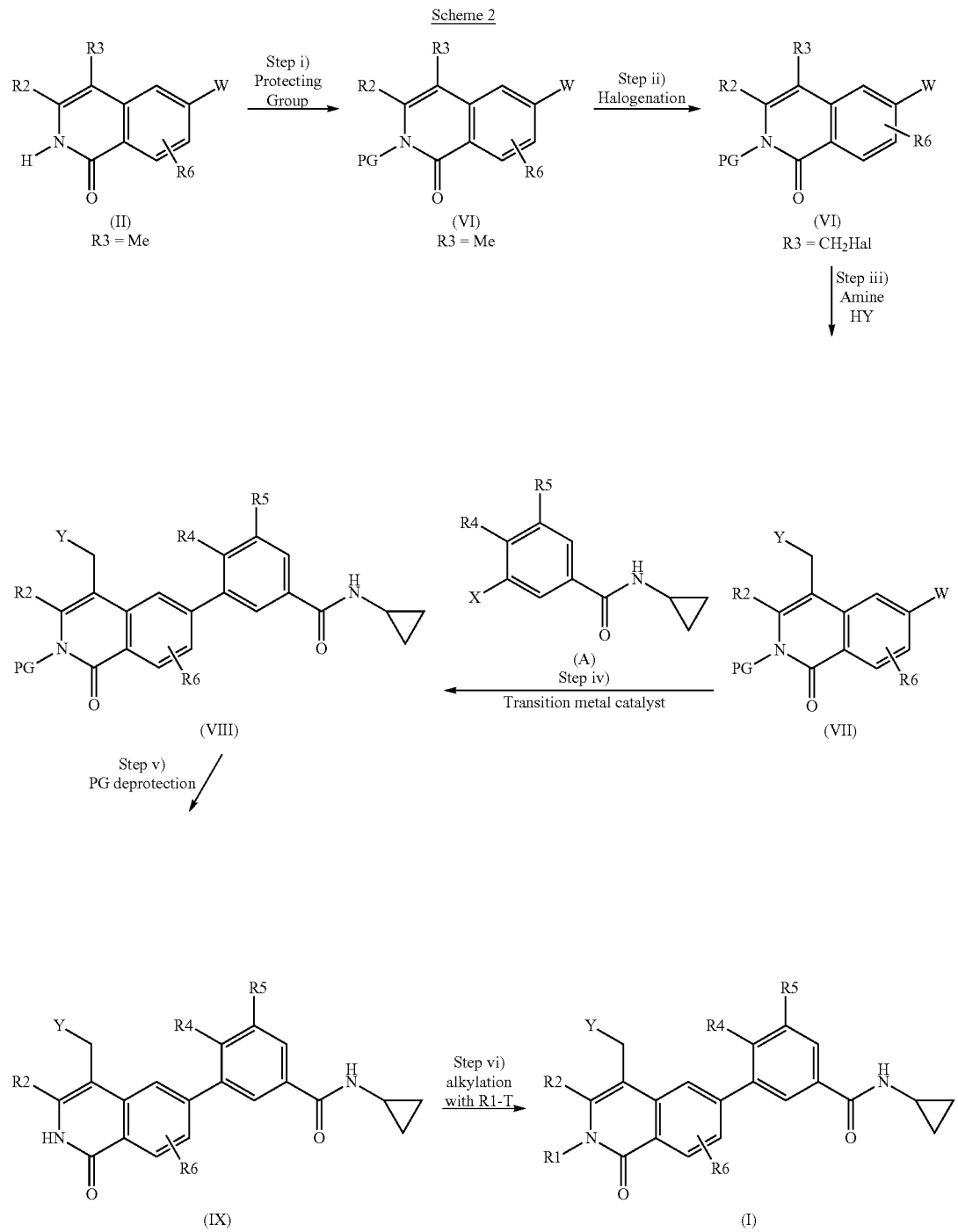

Scheme 2 Step i)

A compound of formula (VI), wherein R2, R3 and R6 are as previously defined in formula (I), W is as previously defined above, and PG is a suitable protecting group, for example phenylsulfonyl, may be prepared by treating a compound of formula (II) with a suitable reagent for introduction of the protecting group, for example $PhSO_2Cl$ in an inert solvent in the presence of a base at a temperature of −20° C. to 150° C. Typically, the reaction is carried out where W is a leaving group such as a halide, for example bromide or iodide, and the base is sodium hydride or N,N-dimethylaminopyridine and $PhSO_2Cl$ is used for the introduction of a PG=$PhSO_2$ and the reaction is carried out in THF, N,N-dimethylformamide or toluene at a temperature between room temperature and 110° C.

Scheme 2 Step ii)

A compound of formula (VI), wherein R2, R3 and R6 are as previously defined in formula (I), and wherein W and PG are as previously defined above, where Hal represents a halogen such as chloro, bromo or iodo, may be prepared by treating a compound of formula (VI), where R3=alkyl, for example methyl, with a halogenating agent such as an N-halosuccinimide, in an inert solvent such as benzene or chloroform in the presence of a catalyst such as dibenzoyl peroxide or zirconium(IV)chloride at a temperature between room temperature and 150° C. Typically the reaction is carried out using N-bromosuccinimide and benzoyl peroxide in benzene at 80° C. for 2-3 h.

Scheme 2 Step iii)

A compound of formula (VII), wherein R2 and R6 are as previously defined in formula (I), and wherein W, PG are as previously defined above may be prepared by treating a compound of formula (VI), where R3=$CH_2Hal$, with an amine HY where Y is a heterocycloalkyl group as previously defined in formula (I). The reaction may be carried out in an inert solvent such as THF at a temperature of 0° C. to 150° C. The reaction may include the presence of an additional base such as Hunig's base ($iPr_2EtN$).

Scheme 2 Step iv)

A compound of formula (VIII) wherein R2, R4, R5, R6 and Y are as previously defined in formula (I), and wherein PG is as previously defined above, may be prepared using a coupling reaction, by treating a compound of formula (VII), wherein W is a leaving group such as a halide (for example bromide or iodide) or an sulfonate ester (for example a trifluoromethane sulfonate) or an boronate ester or boronic acid, with a compound of formula (A), wherein X is a leaving group such as a halide (for example bromide or iodide) or a sulfonate ester (for example a trifluoromethane sulfonate) or a boronate ester or boronic acid. The reaction may be carried out in the presence of a transition metal catalyst such as tetrakis(triphenylphosphine)palladium(0) or 1,1-bis(di-tert-butylphosphino)ferrocene palladium dichloride (Pd-118) in an inert solvent such as N,N-dimethylformamide or 1-methyl-2-pyrrolidinone at a temperature of 0° C. to 150° C. in the presence of a base such as potassium carbonate. Typically, the reaction is carried out where W is bromide and X is $B(OH)_2$ or 4,4,5,5-tetramethyl-[1,3,2]dioxaborolane at a temperature at 80° C. in the presence of 1,1-bis(di-tert-butylphosphino)ferrocene palladium dichloride (Pd-118) and potassium carbonate.

It will be recognized by the skilled person that the conditions utilized for the coupling reaction may lead to partial or full removal of the PG group (particularly where PG=$PhSO_2$, to afford directly a compound of formula (IX) without the need for Scheme 2 Step V).

Scheme 2 Step v)

A compound of formula IX) wherein R2, R4, R5, R6 and Y are as previously defined in formula (I), may be prepared by treating a compound of formula (VIII) with a base such as sodium- or potassium-hydroxide; sodium-, potassium- or cesium-carbonate in a solvent mixture, for example selected from methanol, ethanol, isopropanol, water or THF, at a temperature of 0° C. to 150° C. Typically the reaction is carried out with either sodium hydroxide (1 eq) in aqueous methanol at room temperature or potassium carbonate (1 eq) in methanol at room temperature.

Scheme 2 Step vi)

A compound of formula (I) wherein R1, R2, R3, R4, R5, R6 and Y are as previously defined in formula (I), may be prepared by treating a compound of formula (IX) with a compound of formula R1T in an inert solvent in the presence of a base at a temperature of −20° C. to 150° C. Typically, the reaction is carried out where T is iodide, bromide, chloride, mesylate or tosylate, and the base is sodium hydride, potassium carbonate or cesium carbonate and the reaction is carried out in N,N-dimethylformamide or 1-methyl-2-pyrrolidinone at 100° C.

A compound of formula (I), or a pharmaceutically-acceptable salt thereof, wherein R1, R2, R4, R5, and R6 are as previously defined, may be prepared as shown in Scheme 3.

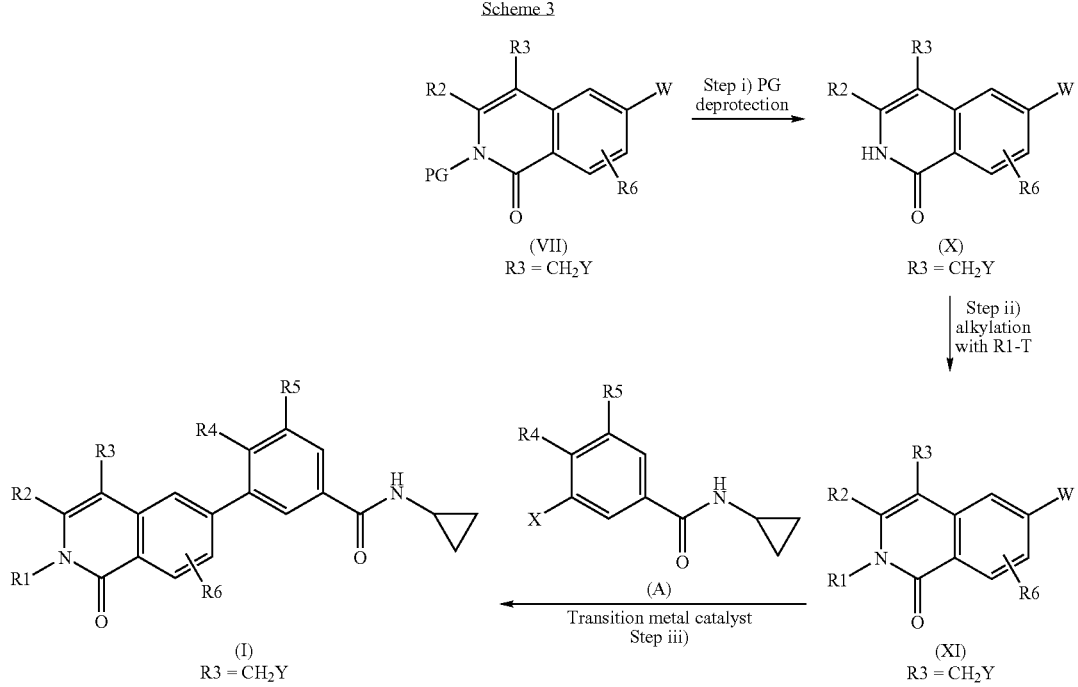

Scheme 3 Step i)

A compound of formula (X) wherein W, R2, R3, and R6 are as previously defined, may be prepared by treating a compound of formula (VII) with a base such as sodium- or potassium-hydroxide; sodium-, potassium- or cesium-carbonate in a solvent mixture, for example selected from methanol, ethanol, isopropanol, water or THF, at a temperature of 0° C. to 150° C. Typically the reaction is carried out with either sodium hydroxide (1 eq) in aqueous methanol at room temperature or using potassium carbonate (1 eq) in methanol at room temperature.

Scheme 3 Step ii)

A compound of formula (XI) wherein R1, R2, R3, and R6 and W are as previously defined above, may be prepared by treating a compound of formula (X) with a compound of formula R1T in an inert solvent in the presence of a base at a temperature of −20° C. to 150° C. Typically, the reaction is carried out where T is iodide, bromide, chloride, mesylate is or tosylate, and the base is sodium hydride, potassium carbonate or cesium carbonate and the reaction is carried out in N,N-dimethylformamide or 1-methyl-2-pyrrolidinone at 100° C.

Scheme 3 Step iii)

A compound of formula (I) wherein R1, R2, R4, R5, and R6 are as previously described may be prepared via a coupling reaction, by treating a compound of formula (XI), wherein W is a leaving group such as a halide (for example bromide or iodide) or a sulfonate ester (for example a trifluoromethane sulfonate) or a boronate ester or boronic acid, with a compound of formula (A), wherein X is a leaving group such as a halide (for example bromide or iodide) or a sulfonate ester (for example a trifluoromethane sulfonate) or a boronate ester or boronic acid. The reaction may be carried out in the presence of a transition metal catalyst such as tetrakis(triphenylphosphine)palladium(0) or 1,1-bis(di-tert-butylphosphino)ferrocene palladium dichloride (Pd-118) in an inert solvent such as N,N-dimethylformamide or 1-methyl-2-pyrrolidinone at a temperature of 0° C. to 150° C. in the presence of a base such as potassium carbonate. Typically, the reaction is carried out where W is bromide and X is B(OH)$_2$ or 4,4,5,5-tetramethyl-[1,3,2]dioxaborolane, at a temperature at 70-80° C. in the presence of 1,1-bis(di-tert-butylphosphino)ferrocene palladium dichloride (Pd-118) and potassium carbonate.

Compounds of formula (A) wherein X is a boronate ester or boronic acid, may be prepared as described in the literature, see for example WO07000339, WO06134382, WO06118256, WO06110173, WO06104889, WO06104915, WO06104917, J. Med. Chem. 2006, 49, 5671, WO05073217, WO05073189, WO05014550 or WO0368747. Compounds of formula R$^1$T and amines HY are commercially available or are prepared by known experimental methods.

A compound of formula (II) may be prepared from a compound of formula (XII) as shown in Scheme 4, wherein R2, R3 and R6 are as previously defined in formula (I) and W is a leaving group such as a halide (for example bromide or iodide).

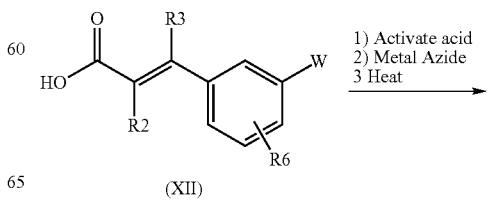

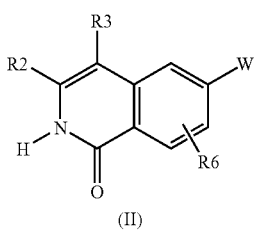

Typically, the acid (XII) is activated by conversion to the acid chloride by treatment with oxalyl chloride in an inert solvent such as dichloromethane. Typically, the acid chloride is then treated with an inorganic azide such as sodium azide in an inert solvent such as tetrahydrofuran/water. Typically, the rearrangement/cyclisation is carried out in an inert solvent such as dichlorobenzene at 190° C.

Compounds of formula (XII) are commercially available or are prepared by known experimental methods.

A compound of formula (I), or a pharmaceutically acceptable salt thereof, wherein R1, R2, R3, R4, R5, and R6 are as previously defined, may be prepared as shown in Schemes 5-7 below.

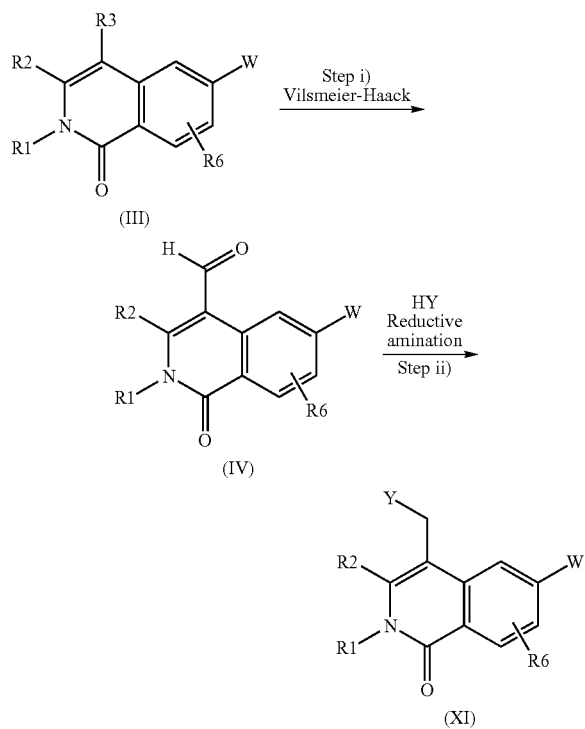

Scheme 5 Step i)

A compound of formula (IV) wherein R1 contains a protected alcohol as the pivalate ester, for example R1=CH$_2$CMe$_2$CH$_2$OC(O)CMe$_3$, R2 and R6 are as previously defined in formula (I), and W is as described above, may be prepared from a compound of formula (III) where R3 is H by a formylation reaction. A formamide such as N,N-dimethylformamide or N-phenyl-N-methylformamide is reacted with an activating agent such as phosphorous oxychloride or oxalyl chloride in a solvent at a temperature of −20° C. to 80° C. followed by reaction of this mixture with a compound of formula (III) at a temperature of 25° C. to 100° C. Preferably the reaction is carried out by addition of a pre-formed mixture of N,N-dimethylformamide and phosphorous oxychloride in N,N-dimethyl formamide to (III) at 0° C. then heating at 75° C. The pivalate ester within R$^1$ is retained during this reaction avoiding undesired chlorination (Scheme 1 step iii).

Compounds of formula (IV) wherein R1 contains an alcohol protected with pivalate ester are valuable synthetic intermediates as it has been found that the pivalate protecting group may be conveniently installed and removed and that it is generally stable in a range of further reactions steps used to prepare compounds of formula (I). In this regard the pivalate protecting group is superior to other alcohol protecting groups such as tert-butyldimethylsilyl. In particular, the pivalate protecting group may be conveniently used in the preparation of compounds of formula (I) wherein R1 is CH$_2$CMe$_2$CH$_2$OH. Accordingly, the present invention further provides a compound of formula (IV), wherein R1 is CH$_2$CMe$_2$CH$_2$OC(O)CMe$_3$; R2 and R6 are as defined in formula (I) and W is a leaving group such as a halide (for example bromide or iodide). In one embodiment, the compound of formula (IV) is 3-(6-bromo-4-formyl-1-oxoisoquinolin-2(1H)-yl)-2,2-dimethylpropyl pivalate.

Scheme 5 Step ii)

A compound of formula (XI) wherein R1, R2, R6 and W are as previously defined may be prepared by a reductive amination reaction between compounds of formula (IV) and an amine HY, wherein Y is a nitrogen-containing group falling within the definition of Y provided herein above and wherein in HY, H is linked to a nitrogen atom. The reductive amination is carried out in the presence of suitable reducing agent such as sodium cyanoborohydride, sodium triacetoxyborohydride or sodium borohydride, either neat or in a solvent such as methanol, ethanol, 1,2-dichloroethane, dichloromethane or 2-methyltetrahydrofuran. Preferably the reaction is carried out in 2-methyltetrahydrofuran in the presence of magnesium sulphate, triethylamine and chlorotrimethylsilane (preferably freshly distilled from K$_2$CO$_3$ and stored under nitrogen).

Preferably, the amine HY is first reacted with chlorotrimethylsilane in the presence of magnesium sulphate and triethylamine at a temperature of 0° C. After warming to room temperature (23° C.), the filtered mixture is added in one portion to a mixture of a compound of formula (IV), triethylamine and magnesium sulphate. Further chlorotrimethylsilane is then added in one portion. After completion of the reaction (~1 h) a reducing agent, preferably sodium triacetoxyborohydride, is added to complete the process. Optionally, sodium borohydride can be added to reduce any unreacted (IV) to aid purification.

A compound of formula (XI) may be transformed into a compound of formula (I), using similar procedures to those in Schemes 1-3.

Scheme 6

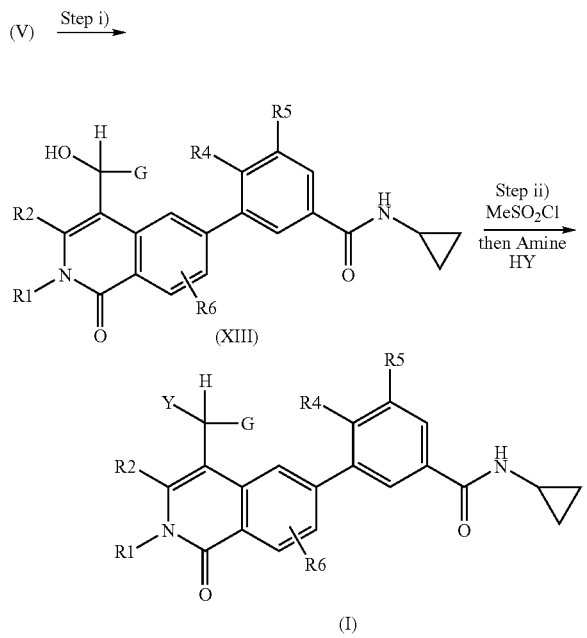

Scheme 6 Step i)

A compound of formula (XIII), wherein R1, R2, R4, R5 and R6, are as previously defined, may be prepared from a compound of formula (V) (Scheme 1) using either a reduction reaction (G=H) or an addition reaction (G=alkyl, for example methyl). Typically the reduction is carried out using sodium borohydride in an alcohol solvent such as ethanol at a temperature of −20° C. to 40° C. Typically, the addition reaction is carried out using a Grignard Reagent (GMgX where X is a halogen and G is an alkyl group for example methylmagnesium chloride) in tetrahydrofuran at 0° C.

Scheme 6 Step ii)

A compound of formula (I) wherein R1, R2, R4, R5, R6 and Y are as previously defined in formula (I), may be prepared by treating a compound of formula (XIII) with a reagent to transform the alcohol within R3 into a leaving group (such as a methanesulfonate ester or halogen) followed by treatment with an amine HY, where Y is a heterocycloalkyl group as previously defined in formula (I).

Typically (XIII) is reacted with methanesulfonyl chloride in an inert solvent such as dichloromethane, in the presence of a base such as triethylamine at a temperature of −20° C. to 40° C. This mixture is then directly treated with an amine HY where Y is a heterocycloalkyl group as previously defined in formula (I). The reaction may be carried out in an inert solvent such as dichloromethane at a temperature of 0° C. to 50° C.

Scheme 7

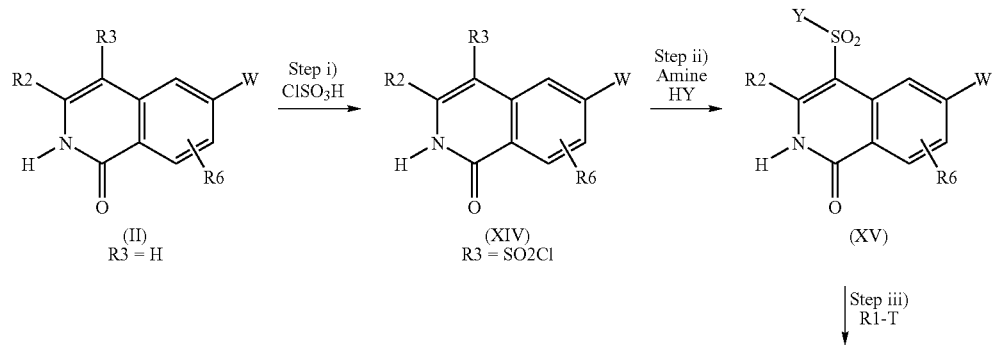

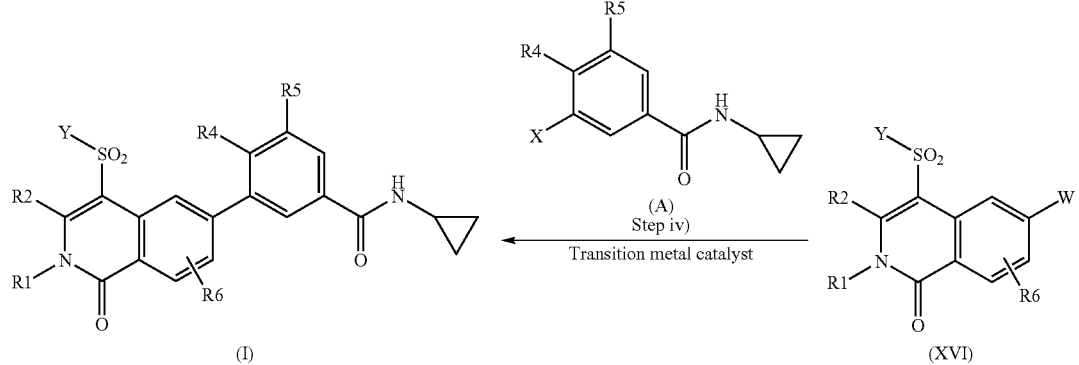

Scheme 7 Step i)

A compound of formula (XIV) wherein R2 and R6 are as previously defined in formula (I), and W is as described above, and R3=SO$_2$Cl may be prepared from a compound of formula (II) where R3=H by a chlorosulfonylation reaction. Typically this is carried out using chlorosulfonic acid at a temperature of 0° C. to 150° C., preferably 90° C.

Scheme 7 Step ii)

A compound of formula (XV) wherein R2, R6 and Y are as previously defined in formula (I), and W is as described above, may be prepared by treating a compound of formula (XIV) with an amine HY, where Y is a heterocycloalkyl group as previously defined in formula (I). Typically the reaction is carried out in an inert solvent such as tetrahydrofuran, in the presence of a base such as triethylamine at a temperature of −20° C. to 40° C.

Scheme 7 Step iii)

A compound of formula (XVI), wherein R1, R2, R6 and Y are as previously defined in formula (I), and W is as described above, may be prepared by treating a compound of formula (XV) with a compound of formula R1T in an inert solvent in the presence of a base at a temperature of −20° C. to 150° C.

Typically, the reaction is carried out where T iodide, bromide, chloride, mesylate or tosylate, W is a leaving group such as a halide, for example bromide or iodide, and the base is potassium carbonate or cesium carbonate and the reaction is carried out in N,N-dimethylformamide or 1-methyl-2-pyrrolidinone at 110° C.

Scheme 7 Step iv)

A compound of formula (I) wherein R1, R2, R4, R5, R6 and Y are as previously described may be prepared via a coupling reaction, by treating a compound of formula (XVI), wherein W is a leaving group such as a halide (for example bromide or iodide) with a compound of formula (A), wherein X is a leaving group such as a boronate ester or boronic acid. Typically, the reaction is carried out in the presence of a transition metal catalyst such as 1,1-bis(di-tert-butylphosphino)ferrocene palladium dichloride (Pd-118) in an inert solvent such as N,N-dimethylformamide at a temperature of 0° C. to 150° C. in the presence of a base such as potassium carbonate. Typically, the reaction is carried out where W is bromide and X is B(OH)$_2$ or 4,4,5,5-tetramethyl-[1,3,2]dioxaborolane, at a temperature at 70-80° C.

It will be appreciated by those skilled in the art that in the processes of the present invention certain functional groups such as hydroxyl, carboxyl, amino or lactam groups in the starting reagents or intermediate compounds may need to be protected by protecting groups. Thus, the preparation of the compounds of formula (I) may involve at a certain stage the removal of one or more protecting groups. The protection and deprotection of functional groups is described in 'Protective Groups in Organic Synthesis', 2nd edition, T. W. Greene and P. G. M. Wuts, Wiley-Interscience (1991) and 'Protecting Groups', P. J. Kocienski, Georg Thieme Verlag (1994).

The compounds of the invention have activity as pharmaceuticals, in particular as p38 kinase inhibitors. Diseases and conditions which may be treated with the compounds include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic is purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Accordingly, the present invention further provides a compound of formula (I) as hereinbefore defined for use in therapy.

In another aspect, the invention provides the use of a compound of formula (I), as hereinbefore defined, in the manufacture of a medicament for use in therapy.

In another aspect, the invention provides a compound of formula (I), as hereinbefore defined, for use as a medicament.

In the context of the present specification, the term "therapy" also includes "prophylaxis" unless there are specific indications to the contrary. The terms "therapeutic" and "therapeutically" should be construed accordingly.

A further aspect of the invention provides a method of treating a disease state in a is mammal suffering from, or at risk of, said disease, which comprises administering to a mammal in need of such treatment a therapeutically effective amount of a compound of formula (I) as hereinbefore defined.

The present invention also provides the use of a compound of formula (I) as hereinbefore defined, in the manufacture of a medicament for use in the treatment of chronic obstructive pulmonary disease (COPD) (such as irreversible COPD).

The present invention also provides the use of a compound of formula (I) as hereinbefore defined, in the manufacture of a medicament for use in the treatment of asthma.

The present invention also provides a compound of formula (I) as hereinbefore defined, for treating chronic obstructive pulmonary disease (COPD) (such as irreversible COPD).

The present invention also provides a compound of formula (I) as hereinbefore defined, for treating asthma.

The present invention further provides a method of treating chronic obstructive pulmonary disease (COPD) (such as irreversible COPD), in a warm-blooded animal, such as man, which comprises administering to a mammal in need of such treatment an effective amount of a compound of formula (I) as hereinbefore defined.

The present invention further provides a method of treating asthma in a warm-blooded animal, such as man, which comprises administering to a mammal in need of such treatment an effective amount of a compound of formula (I) as hereinbefore defined.

In order to use a compound of the invention for the therapeutic treatment of a warm-blooded animal, such as man, said ingredient is normally formulated in accordance with standard pharmaceutical practice as a pharmaceutical composition.

Therefore in another aspect the present invention provides a pharmaceutical composition that comprises a compound of the invention as hereinbefore defined and a pharmaceutically acceptable adjuvant, diluent or carrier. In a further aspect the present invention provides a process for the preparation of said composition, which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule, which contains between 0.1 mg and 1 g of active ingredient.

In another aspect a pharmaceutical composition of the invention is one suitable for intravenous, subcutaneous or intramuscular injection. Each patient may receive, for example, an intravenous, subcutaneous or intramuscular dose of 0.01 mgkg$^{-1}$ to 100 mgkg$^{-1}$ of the compound, for example in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose, which is approximately equivalent to the daily parenteral dose, the composition being administered 1 to 4 times per day Another suitable pharmaceutical composition of this invention is one suitable for inhaled administration, inhalation being a particularly useful method for administering the compounds of the invention when treating respiratory diseases such as chronic obstructive pulmonary disease (COPD) or asthma. When administered by inhalation the compounds of formula (I) may be used effectively at doses in the μg range, for example 0.1 to 500 μg, 0.1 to 50 μg, 0.1 to 40 μg, 0.1 to 30 μg, 0.1 to 20 μg, 0.1 to 10 μg, 5 to 10 μg, 5 to 50 μg, 5 to 40 μg, 5 to 30 μg, 5 to 20 μg, 5 to 10 μg, 10 to 50 μg, 10 to 40 μg 10 to 30 μg, or 10 to 20 μg of active ingredient.

In an embodiment of the invention, there is provided a pharmaceutical composition comprising a compound of the invention as hereinbefore defined, in association with a pharmaceutically acceptable adjuvant, diluent or carrier, which is formulated for inhaled administration.

When administered by inhalation, metered dose inhaler devices may be used to administer the active ingredient, dispersed in a suitable propellant and with or without additional excipients such as ethanol, surfactants, lubricants or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients. Nebulised aqueous suspensions or, preferably, solutions may also be employed, with or without a suitable pH and/or tonicity adjustment, either as a unit-dose or multi-dose formulations.

Dry powder inhalers may be used to administer the active ingredient, alone or in combination with a pharmaceutically acceptable carrier, in the later case either as a finely divided powder or as an ordered mixture. The dry powder inhaler may be single dose or multi-dose and may utilise a dry powder or a powder-containing capsule. Metered dose inhaler, nebuliser and dry powder inhaler devices are well known and a variety of such devices are available.

The invention further relates to combination therapies wherein a compound of the invention or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the is invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumaro-coxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention with a monoclonal antibody targeting B-Lymphocytes (such as CD20 (rituximab), MRA-aIL16R and T-Lymphocytes, CTLA4-Ig, HuMax II-15).

The present invention still further relates to the combination of a compound of the invention with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family.

The present invention further relates to the combination of a compound of the invention with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY×1005.

The present invention further relates to the combination of a compound of the invention and a receptor antagonist for leukotrienes (LT) B4, LTC4, LTD4, and LTE4 selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY× 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a proton pump inhibitor (such as omeprazole) or a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agent including a muscarinic receptor (M1, M2, and M3) antagonist such as atropine, hyoscine, glycopyrrolate, ipratropium bromide, tiotropium bromide, oxitropium bromide, pirenzepine or telenzepine.

The present invention still further relates to the combination of a compound of the invention and a beta-adrenoceptor agonist (including beta receptor subtypes 1-4) such as isoprenaline, salbutamol, formoterol, salmeterol, terbutaline, orciprenaline, bitolterol mesylate, pirbuterol, or indacaterol or a chiral enantiomer thereof.

The present invention further relates to the combination of a compound of the invention and a chromone, such as sodium cromoglycate or nedocromil sodium.

The present invention still further relates to the combination of a compound of the invention with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention is with an agent that modulates a nuclear hormone receptor such as PPARs.

The present invention still further relates to the combination of a compound of the invention together with an immunoglobulin (Ig) or Ig preparation or an antagonist or antibody modulating Ig function such as anti-IgE (for example omalizumab).

The present invention further relates to the combination of a compound of the invention and another systemic or topically-applied anti-inflammatory agent, such as thalidomide or a derivative thereof, a retinoid, dithranol or calcipotriol.

The present invention still further relates to the combination of a compound of the invention and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine is reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B1.- or B2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK1 or NK3 receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; is (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2x7; or (xxvii) inhibitor of transcription factor activation such as NFkB, API, or STATS.

A compound of the invention can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholino propoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a further embodiment the present invention provides a pharmaceutical product comprising, in combination, a first active ingredient which is a compound of formula (I) or a pharmaceutically acceptable salt or N-oxide thereof, as hereinbefore described, and at least one further active ingredient selected from:— a phosphodiesterase inhibitor
a β2. adrenoceptor agonist
a modulator of chemokine receptor function
a protease inhibitor
a steroidal glucocorticoid receptor agonist
an anticholinergic agent, and a
a non-steroidal glucocorticoid receptor agonist.

The pharmaceutical product according to this embodiment may, for example, be a pharmaceutical composition comprising the first and further active ingredients in admixture. Alternatively, the pharmaceutical product may, for example, comprise the first and further active ingredients in separate pharmaceutical preparations suitable for simultaneous, sequential or separate administration to a patient in need thereof.

The pharmaceutical product of this embodiment is of particular use in treating respiratory diseases such as asthma, COPD or rhinitis.

Examples of a phosphodiesterase inhibitor that may be used in the pharmaceutical product according to this embodiment include a PDE4 inhibitor such as an inhibitor of the isoform PDE4D, a PDE3 inhibitor and a PDE5 inhibitor. Examples include the compounds (Z)-3-(3,5-dichloro-4-pyridyl)-2-[4-(2-indanyloxy-5-methoxy-2-pyridyl]propenenitrile, N-[9-amino-4-oxo-1-phenyl-3,4,6,7-tetrahydropyrrolo[3,2, 1-jk][1,4]benzodiazepin-3(R)-yl]pyridine-3-carboxamide (CI-1044),
3-(benzyloxy)-1-(4-fluorobenzyl)-N-[3-(methylsulphonyl) phenyl]-1H-indole-2-carboxamide,
(1S-exo)-5-[3-(bicyclo[2.2.1]hept-2-yloxy)-4-methoxyphenyl]tetrahydro-2(1H)-pyrimidinone (Atizoram),
N-(3,5,dichloro-4-pyridinyl)-2-[1-(4-fluorobenzyl)-5-hydroxy-1H-indol-3-yl]-2-oxoacetamide (AWD-12-281),
β-[3-(cyclopentyloxy)-4-methoxyphenyl]-1,3-dihydro-1,3-dioxo-2H-isoindole-2-propanamide (CDC-801),
N-[9-methyl-4-oxo-1-phenyl-3,4,6,7-tetrahydropyrrolo[3,2, 1-jk][1,4]benzodiazepin-3(R)-yl]pyridine-4-carboxamide (CI-1018),
cis-[4-cyano-4-(3-cyclopentyloxy-4-methoxyphenyl)cyclohexane-1-carboxylic acid (Cilomilast),
8-amino-1,3-bis(cyclopropylmethyl)xanthine (Cipamfylline),
N-(2,5-dichloro-3-pyridinyl)-8-methoxy-5-quinolinecarboxamide (D-4418),
5-(3,5-di-tert-butyl-4-hydroxybenzylidene)-2-iminothiazolidin-4-one (Darbufelone),
2-methyl-1-[2-(1-methylethy)pyrazolo[1,5-a]pyridin-3-yl]-1-propanone (Ibudilast),
2-(2,4-dichlorophenylcarbonyl)-3-ureidobenzofuran-6-yl methanesulphonate (Lirimilast),
(−)-(R)-5-(4-methoxy-3-propoxyphenyl)-5-methyloxazolidin-2-one (Mesopram),
(−)-cis-9-ethoxy-8-methoxy-2-methyl-1,2,3,4,4a,10b-hexahydro-6-(4-diisopropylaminocarbonylphenyl)-benzo [c][1,6]naphthyridine (Pumafentrine),
3-(cyclopropylmethoxy)-N-(3,5-dichloro-4-pyridyl)-4-(difluoromethoxy)benzamide (Roflumilast),
the N-oxide of Roflumilast,
5,6-diethoxybenzo[b]thiophene-2-carboxylic acid (Tibenelast),
2,3,6,7-tetrahydro-2-(mesitylimino)-9,10-dimethoxy-3-methyl-4H-pyrimido[6,1-a]isoquinolin-4-one (trequinsin) and
3-[[3-(cyclopentyloxy)-4-methoxyphenyl]-methyl]-N-ethyl-8-(1-methylethyl)-3H-purine-6-amine (V-11294A).

Examples of a β$_2$-adrenoceptor agonist that may be used in the pharmaceutical product according to this embodiment include metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol or indacaterol. The β$_2$-adrenoceptor agonist of this embodiment may be a long-acting β$_2$-agonists, for example salmeterol (e.g. as xinafoate), formoterol (e.g. as fumarate), bambuterol (e.g. as hydrochloride), carmoterol (TA 2005, chemically identified as 2(1H)-Quinolone, 8-hydroxy-5-[1-hydroxy-2-[[2-(4-methoxy-phenyl)-1-methylethyl]-amino]ethyl]-monohydrochloride, [R-(R*,R*)] also identified by Chemical Abstract Service Registry Number 137888-11-0 and disclosed in U.S. Pat. No. 4,579,854), indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)-benzenesulfonamide as disclosed in WO 2002/76933, benzenesulfonamide derivatives e.g. 3-(4-{[6-({(2R)-2-hydroxy-2-[4-hydroxy-3-(hydroxy-methyl)phenyl]ethyl}aminoyhexyl]oxy}butyl) benzenesulfonamide as disclosed in WO 2002/88167, aryl aniline receptor agonists as disclosed in WO 2003/042164 and WO 2005/025555, indole derivatives as disclosed in WO 2004/032921, in US 2005/222144, compounds GSK 159797, GSK 159802, GSK 597901, GSK 642444 and GSK 678007.

Examples of a modulator of chemokine receptor function that may be used in the pharmaceutical product according to this embodiment include a CCR1 receptor antagonist.

Examples of a protease inhibitor that may be used in the pharmaceutical product according to this embodiment include an inhibitor of neutrophil elastase or an inhibitor of MMP12.

Examples of a steroidal glucocorticoid receptor agonist that may be used in the pharmaceutical product according to this embodiment include budesonide, fluticasone (e.g. as propionate ester), mometasone (e.g. as furoate ester), beclomethasone (e.g. as 17-propionate or 17,21-dipropionate esters), ciclesonide, loteprednol (as e.g. etabonate), etiprednol (as e.g. dicloacetate), triamcinolone (e.g. as acetonide), flunisolide, zoticasone, flumoxonide, rofleponide, butixocort (e.g. as propionate ester), prednisolone, prednisone, tipredane, steroid esters e.g. 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, steroid esters according to DE 4129535, steroids according to WO 2002/00679, WO 2005/041980, or steroids GSK 870086, GSK 685698 and GSK 799943.

Examples of an anticholinergic agent that may be used in the pharmaceutical product according to this embodiment include for example a muscarinic receptor antagonist (for example a M1, M2 or M3 antagonist, such as a M3 antagonist) for example ipratropium (e.g. as bromide), tiotropium (e.g. as bromide), oxitropium (e.g. as bromide), tolterodine, pirenzepine, telenzepine, glycopyrronium bromide (such as R,R-glycopyrronium bromide or a mixture of R,S- and S,R-glycopyrronium bromide); mepensolate (e.g. as bromide), a quinuclidine derivative such as 3(R)-(2-hydroxy-2,2-dithien-2-ylacetoxy)-1-(3-phenoxypropyl)-1-azonia-bicyclo[2.2.2] octane bromide as disclosed in US 2003/0055080, quinuclidine derivatives as disclosed in WO 2003/087096 and WO 2005/115467 and DE 10050995; or GSK 656398 or GSK 961081.

Examples of a modulator of a non-steroidal glucocorticoid receptor agonist that may be used in the pharmaceutical product according to this embodiment include those described in WO2006/046916.

The ability of the compounds of formula (I) to inhibit p38 kinase may be determined using the following biological assay:

p38 Alpha Enzyme Assay

Enzyme assays were performed in polypropylene 96 well plates. The following solutions were added to each well; 10 μL of compound dilutions in assay buffer (20 mM HEPES pH 7.4, containing 20 mM magnesium acetate, 0.005% (w/v) Tween-20, 10 mM DTT) containing 1% (v/v) DMSO or assay buffer containing 1% (v/v) DMSO alone, 70 μL of assay buffer containing 36 nM substrate (biotinylated-ATF2) and 10 μL of an appropriate dilution of human active recombinant p38-6H is tagged. Depending on batch of p38, an appropriate dilution was typically a 5 nM solution to give a final enzyme concentration of 0.5 nM. At this stage, background control wells also received 50 μL of AlphaScreen quench buffer (10 mM HEPES pH 7.4 containing 100 mM EDTA, 0.2% (w/v) bovine serum albumin). The plate was covered, pre-incubated for 4 hours at 37° C. and the enzyme reaction initiated by addition of 10 μL 1 mM ATP. After incubation for a further 45 minutes at 37° C., the reaction was stopped by addition of 50 μL quench reagent and 50 μL of the quenched reaction mixture transferred to an opaque, white 96-well plate. Detection reagent, 25 μL of 10 mM HEPES pH 7.4 containing 100 mM EDTA, 0.2% (w/v) bovine serum albumin, 0.3 nM anti phosphoATF2 antibody and 25 μg/mL of AlphaScreen protein A acceptor and donor beads' (PerkinElmer Inc.), was added to all wells in a darkened room, the plate sealed and left in the dark for at least 5 hours before AlphaScreen readings were taken using a Perkin Elmer EnVision reader. Total, uninhibited activity was determined from assays performed in each assay plate. The mean control in the absence of p38 activity was subtracted from each well. Data were expressed as percent inhibition of total activity using equation 1.

Percent Inhibition=100*(1−Test/Control)    Eq.1

Where . . .
Test=p38 kinase activity in the presence of compound
Control=p38 kinase activity in the absence of compound.

$pIC_{50}$ is defined as the logarithm of the reciprocal of the concentration of compound required for 50% reduction in total p38 kinase activity.

Using this assay, the compounds of the present invention all exhibit a potency, expressed as a $pIC_{50}$, of greater than 8.0. The potency values are given in the Table below.

| Example Number | p38α inhibition Mean $pIC_{50}$ |
|---|---|
| 1 | 9.9 |
| 2 | 9.6 |
| 3 | 9.8 |
| 4 | 9.3 |
| 5 | 9.7 |
| 6 | 9.0 |
| 7 | 9.3 |
| 8 | 9.6 |
| 9 | 8.8 |
| 10 | 10.1 |
| 11 | 9.8 |
| 12 | 9.4 |
| 13 | 9.3 |
| 14 | 9.3 |
| 15 | 9.3 |
| 16 | 9.6 |
| 17 | 9.6 |
| 18 | 9.1 |
| 19 | 9.4 |
| 20 | 9.1 |
| 21 | 9.6 |
| 22 | 9.8 |
| 23 | 9.5 |
| 24 | 9.2 |
| 25 | 8.8 |
| 26 | 9.6 |
| 27 | 9.5 |
| 28 | 9.1 |
| 29 | 9.1 |
| 30 | 9.9 |
| 31 | 9.1 |
| 32 | 9.1 |
| 33 | 9.8 |
| 34 | 9.0 |
| 35 | 8.3 |
| 36 | 8.5 |
| 37 | 9.5 |
| 38 | 9.7 |
| 39 | 9.2 |
| 40 | 10.1 |
| 41 | 9.2 |
| 42 | 9.1 |
| 43 | 9.3 |
| 44 | 8.9 |
| 45 | 9.9 |
| 46 | 9.8 |
| 47 | 9.6 |
| 48 | 9.4 |
| 50 | 9.7 |
| 51 | 10.0 |
| 52 | 9.7 |
| 53 | 9.4 |
| 54 | 9.6 |
| 55 | 8.6 |
| 56 | 9.1 |
| 57 | 9.8 |
| 49 | 9.3 |
| 58 | 9.5 |
| 59 | 9.3 |
| 60 | 9.4 |
| 61 | 10.0 |
| 62 | 9.7 |
| 63 | 9.4 |
| 64 | 10.0 |
| 65 | >10.2 |
| 66 | 9.7 |
| 67 | 9.6 |

The standard deviation of the p38 enzyme inhibition assay is between 0.2 and 0.3 log units. The pIC50 values in the above table are means of replicate determinations which were within 2×SD (95% confidence) of each other.

LPS Challenge Assay

The following is a description of an assay that may be used to evaluate a compounds activity on neutrophil migration into the airway after aerosol challenge with lipopolysaccharide (LPS) in the Han Wistar (HW) rat.

LPS challenge in HW rats caused an influx of inflammatory cells into the lungs. Rats were challenged either with an aerosol of 0.9% w/v saline or 0.5 mg/mL LPS in 0.9% saline for 30 min. Rats were dosed with vehicle or test compound by nose-only inhalation administration at various time points before challenge depending upon the experimental protocol. Test compound groups could either be the same compound at different doses or single doses of different compounds. Test compounds were compared to suitable reference compounds if available, dosed as appropriate, i.e. orally or by inhalation.

The rats were euthanized with 200 mg pentobarbitone sodium at various time points after challenge depending upon the nature of the study, but typically 4 hr after LPS challenge. A tracheotomy was performed and a cannula inserted. The airway was then lavaged using 3 mL sterile Isoton (Beckman Coulter) at room temperature. The Isoton was left in the airway for 10 seconds before being removed and then placed into a 15 mL centrifuge tube on ice. This process was repeated two further times and BAL fluid placed into a second tube. The two BAL lavage tubes from each rat were centrifuged at 1800 rpm for 10 min at 4° C., and the lavage fluid supernatant from the first tube retained and stored at −80° C. for possible cytokine analysis. The lavage fluid supernatant from the second tube was discarded, the two cell pellets combined and resuspended in 1 mL Isoton and made up to a final volume of 5 mL. An aliquot of BAL fluid was removed and counted on the Sysmex XT2000Vet automated cell counter (Sysmex UK, Milton Keynes). The results were expressed in cells/L×$10^9$. Cells were classified as eosinophils, neutrophils or mononuclear cells (mononuclear cells included monocytes, macrophages and lymphocytes) and were expressed as a percentage of the total cell count.

Compounds were scored as active if a statistically significant (i.e. p<0.05) inhibition of the LPS-induced BAL neutrophilia response was observed.

When tested in the LPS Challenge Assay, the compound of Example 26 was active at a nebuliser concentration of <1 mg/mL when dosed 0.5 hour before the LPS challenge.

In Vitro Micronucleus Assay

The following is a description of an assay that may be used to assess the genotoxicity of a compound using mouse lymphoma L5178T cells.

The in vitro micronucleus assay (IVM) detects chemicals that induce chromosomal damage by measuring the formation of small intra cell membrane-bound DNA fragments. At AstraZeneca, L5178Y cells are used as these are the cells of choice for follow on regulatory mammalian cell in vitro genotoxicity screening. The test system is simple to perform and produces rapid results. The IVM is suitable as a preliminary genetic toxicity-screening assay prior to compound selection.

A wide range of test chemical concentrations, up to 1 mmol/L or the chemicals solubility limit, is tested. Quadruplicate solvent control cultures, duplicate positive control cultures and single test chemical cultures are used. Control or test chemical solution is added to the cell cultures at 1% v/v. Treatment exposure is for 3 hours in the presence or absence of an exogenous metabolising system (aroclor induced S9 mix). Where possible, 20 hours after treatment exposure, at least three concentrations giving acceptable levels of toxicity (greater than 10% survival as measured by two day relative suspension growth) are selected for analysis of micronucleated cells. For the selected cultures, microscope slides are prepared by centrifuging $2 \times 10^4$ cells in a Cytospin 3 (Shandon) centrifuge (800 rpm for 8 minutes) and fixed with 90% methanol. Slides are stained with DAPI. Slides are initially scanned to find micronucleated cells using MetaSystems' Metafer 4, comprising of a Zeiss Axioplan Imager Z1. All identified micronuclei are confirmed by eye to be separate and within the cytoplasm, to have intact cytoplasmic membrane and to be less than one third of the diameter of the main nucleus. Where possible, a total of at least 1000 cells per culture are scored.

For any concentration, an increase in the number of micronucleated cells is considered to be significant if the increase is at least 2-fold the concurrent solvent control level, and the number of micronucleated cells is greater than 8 per thousand cells scored.

When tested in the micronucleus assay, the compound of Example 26 was inactive.

The present invention is further illustrated by the non-limiting examples that follow below.

In the examples the NMR spectra were measured on a Varian Unity Inova spectrometer at a proton frequency of either 300 or 400 MHz. Reactions that were heated by microwace irradiation were performed using a CEM Discover Microwave. Examples having chiral centre might appear in NMR as a mixture of rotamers. The MS spectra were measured on either an Agilent 1100 MSD G1946D spectrometer or a Hewlett Packard HP1100 MSD G1946A spectrometer. Preparative HPLC separations were performed using a Waters Symmetry® or Xterra® or Xbridge column or Phenomenex Gemini® using the eluents indicated. Compound names were generated using the chemical naming software package IUPAC Name (ACD) v10.06.

The following abbreviations have been used:—

| | |
|---|---|
| DMF | N,N-dimethylformamide |
| DMSO | dimethylsulphoxide |
| THF | tetrahydrofuran |
| DMA | N,N-dimethylacetamide |
| DCM | dichloromethane |
| HATU | O-(7-Azabenzotriazol-1-yl)-N,N,N',N'-tetramethyluronium hexafluorophosphate |
| Pd-118 | 1,1-bis(di-tert-butylphosphino)ferrocene palladium dichloride |
| Pd(dppf)$_2$Cl$_2$ | [1,1'-Bis(diphenylphosphino)ferrocene]dichloropalladium(II) complex with CH$_2$Cl$_2$ |

EXAMPLE 1

N-Cyclopropyl-3-fluoro-5-[2-(3-hydroxy-2,2-dimethylpropyl)-1-oxo-4-(piperazin-1-ylmethyl)-1,2-dihydroisoquinolin-6-yl]-4-methylbenzamide

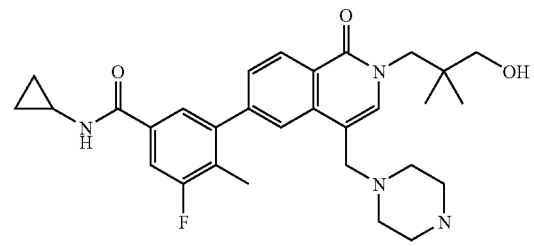

a) 4-Bromo-2-[(E)-2-(dimethylamino)ethenyl]benzonitrile

A solution of 4-bromo-2-methylbenzonitrile (1.0 g) dissolved in 1-tert-butoxy-N,N,N',N'-tetramethylmethanediamine (2.11 ml) was stirred at 140° C. for 2 h (flask open to evaporate t-butanol). The reaction mixture was diluted with water (250 mL), and extracted with ethyl acetate (350 mL). The organic was dried (MgSO$_4$), filtered and evaporated to afford the crude product. The crude product was triturated with isohexane overnight to afford the subtitle compound (0.75 g) as a solid.

$^1$H NMR δ(CDCl$_3$) 7.50 (s, 1H), 7.34 (s, 1H), 7.05-6.96 (m, 2H), 5.29 (d, 1H), 2.94 (s, 6H).

b) 6-Bromoisoquinolin-1(2H)-one

A solution of 4-bromo-2-[(E)-2-(dimethylamino)ethenyl] benzonitrile (Example 1a, 1.0 g) in 33% Hydrobromic acid in acetic acid (10 mL) under nitrogen was stirred at 80° C. for 4 h. The reaction mixture was diluted with water (250 mL), and the brown solid was filtered off, washed with diethyl ether and dried to afford the subtitle compound (0.70 g) as a solid.

$^1$H NMR δ(DMSO-d$_6$) 11.43 (s, 1H), 8.12-8.03 (m, 1H), 7.98-7.88 (m, 1H), 7.62 (d, 1H), 7.27-7.18 (m, 1H), 6.57-6.47 (m, 1H).

c) 6-Bromo-2-(3-{[tert-butyl(dimethyl)silyl]oxy}-2,2-dimethylpropyl)isoquinolin-1(2H)-one A solution of 6-bromoisoquinolin-1(2H)-one (Example 1b, 1.5 g) dissolved in NMP (15 mL) was treated with potassium carbonate (1.48 g) and (3-bromo-2,2-dimethylpropoxy)(tert-butyl)dimethylsilane (2.26 g) under nitrogen. The resulting mixture was stirred at 70° C. for 10 h (low conversion), heating was continued at 100° C. for 10 h. The reaction mixture was diluted with water (250 mL), and extracted with ethyl acetate (300 mL). The organic was dried (MgSO₄), filtered and evaporated to afford crude product. The crude product was purified (SiO₂ chromatography, elution with 20% diethyl ether in isohexane) to afford the subtitle compound (1.30 g) as an oil.

MS: APCI(+ve) 424/6 (M+H)⁺.

d) 6-Bromo-2-(3-chloro-2,2-dimethylpropyl)-1-oxo-1,2-dihydroisoquinoline-4-carbaldehyde Phosphorus oxychloride (2.57 mL) was added to a cooled solution of DMF (10 mL) and the reaction stirred at room temperature for 2 h before being treated with 6-bromo-2-(3-{[tert-butyl(dimethyl)silyl]oxy}-2,2-dimethylpropyl)isoquinolin-1(2H)-one (Example 1c, 1.3 g) in DMF (10 mL) under nitrogen. The resulting solution was stirred at 70° C. for 10 h. The reaction mixture was diluted with water (300 mL), and extracted with ethyl acetate (300 mL). The organic was dried (MgSO₄), filtered and evaporated to afford crude product. The crude product was purified (SiO₂ chromatography, elution 50% diethyl ether in isohexane) to afford the subtitle compound (0.45 g) as a solid.

¹H NMR δ (CDCl₃) 9.77 (s, 1H), 9.26 (s, 1H), 8.26 (d, 1H), 7.84 (s, 1H), 7.69 (d, 1H), 4.18 (s, 2H), 3.47 (s, 2H), 1.16 (s, 6H).

e) 3-(6-Bromo-4-formyl-1-oxoisoquinolin-2(1H)-yl)-2,2-dimethylpropyl acetate

A solution of 6-bromo-2-(3-chloro-2,2-dimethylpropyl)-1-oxo-1,2-dihydroisoquinoline-4-carbaldehyde (Example 1d, 0.45 g) in dimethylsulfoxide (10 mL) was treated with sodium acetate (0.343 g) under nitrogen. The resulting mixture was stirred at 100° C. for 10 h. Sodium iodide (1 eq) was added and the reaction heated at 120° C. for 30 h. The reaction mixture was diluted with water (250 mL) and the solid filtered off and dried to afford the subtitle compound (0.25 g) as a solid.

¹H NMR δ(CDCl₃) 9.81 (s, 1H), 9.28 (s, 1H), 8.29 (d, 1H), 7.73-7.66 (m, 2H), 4.04 (s, 2H), 3.20 (s, 2H), 1.07 (s, 6H).

f) N-Cyclopropyl-3-fluoro-5-(4-formyl-2-(3-hydroxy-2,2-dimethylpropyl)-1-oxo-1,2-dihydroisoquinolin-6-yl)-4-methylbenzamide A solution of 3-(6-bromo-4-formyl-1-oxoisoquinolin-2 (1H)-yl)-2,2-dimethylpropyl acetate (Example 1e, 0.25 g) in DMF (10 mL) was treated with N-cyclopropyl-3-fluoro-4-methyl-5-(4,4,5,5-tetramethyl-1,3,2-dioxaborolan-2-yl)benzamide (0.28 g), Pd-118 (0.024 g) and potassium carbonate (0.31 g) under nitrogen. The resulting mixture was stirred at 70° C. for 6 h. Methanol (10 mL) was added and stirred at room temperature for 1 h. The reaction mixture was diluted with water (250 mL), and extracted with ethyl acetate (300 mL). The organic was dried (MgSO₄), filtered and evaporated to afford crude product. The crude product was purified (SiO₂ chromatography, elution with 100% ethyl acetate) to afford the subtitle compound (0.30 g) as an oil.

MS: APCI(+ve) 451 (M+H)⁺.

g) N-Cyclopropyl-3-fluoro-5-(2-(3-hydroxy-2,2-dimethylpropyl)-1-oxo-4-(piperazin-1-ylmethyl)-1,2-dihydroisoquinolin-6-yl)-4-methylbenzamide A solution of N-cyclopropyl-3-fluoro-5-(4-formyl-2-(3-hydroxy-2,2-dimethylpropyl)-1-oxo-1,2-dihydroisoquinolin-6-yl)-4-methylbenzamide (Example 1f, 0.15 g) in DCE (5 mL) was treated with 1-Boc-piperazine (0.19 g) and titanium (IV) isopropoxide (0.30 mL) under nitrogen. The resulting mixture was stirred at 20° C. for 16 h before adding sodium triacetoxyborohydride (0.28 g). The mixture was stirred at room temperature for 2 h before adding TFA (5 mL). The mixture stirred at room temperature for 2 h and evaporated to dryness. The mixture was quenched with 10% aq ammonia (5 mL) and extracted with ethyl acetate. The organic was dried (MgSO₄), filtered and evaporated to afford crude product. The crude product was purified by preparative HPLC (Phenomenex Gemini column using a 95-5% gradient of aqueous 0.2% ammonia in acetonitrile as eluent) to afford the title compound (0.065 g) as a white solid.

MS: APCI(+ve) 521 (M+H)⁺.

¹H NMR δ(DMSO-d₆) 8.54 (d, 1H), 8.35 (d, 1H), 7.99 (s, 1H), 7.70-7.63 (m, 2H), 7.55 (d, 1H), 7.39 (s, 1H), 4.90-4.84 (m, 1H), 3.93 (s, 2H), 3.50 (s, 2H), 3.15-3.08 (m, 2H), 2.89-2.83 (m, 1H), 2.68-2.59 (m, 4H), 2.38-2.22 (m, 7H), 0.84 (s, 6H), 0.74-0.66 (m, 2H), 0.61-0.53 (m, 2H).

EXAMPLE 2

N-Cyclopropyl-3-fluoro-5-{2-(3-hydroxy-2,2-dimethylpropyl)-4-[(4-methyl-1,4-diazepan-1-yl)methyl]-1-oxo-1,2-dihydroisoquinolin-6-yl}-4-methylbenzamide

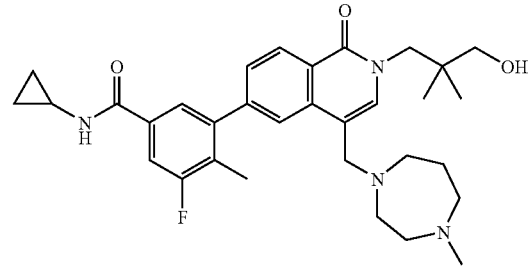

a) 6-Bromo-2-(3-hydroxy-2,2-dimethylpropyl)isoquinolin-1(2H)-one

A solution of 6-bromoisoquinolin-1(2H)-one (Example 1b, 2.5 g) dissolved in NMP (20 mL) was treated with cesium carbonate (7.27 g) and 3-bromo-2,2-dimethylpropan-1-ol (2.75 mL) under nitrogen. The resulting mixture was stirred at 100° C. for 8 h. Further cesium carbonate (1 eq), 3-bromo-2,2-dimethylpropan-1-ol (1 eq) and water (5 mL) were added and the resulting mixture was stirred at 130° C. for 10 h. The incomplete reaction was diluted with water and extracted with ethyl acetate. The organic was dried (MgSO₄), filtered and evaporated to afford crude product. The crude product was dissolved in NMP (20 mL) was treated with cesium carbonate (7.27 g) and 3-bromo-2,2-dimethylpropan-1-ol (2.75 mL) and sodium iodide (0.167 g) under nitrogen and heated at 130° C. for 10 h. The reaction mixture was diluted with water (250 mL), and extracted with ethyl acetate (300 mL). The organic was dried (MgSO₄), filtered and evaporated to afford crude product. The crude product was purified by (SiO₂ chromatography, elution 60% diethyl ether in isohexane) to afford the subtitle compound (0.93 g) as a solid.

¹H NMR δ(CDCl₃) 8.30 (d, 1H), 7.75-7.68 (m, 1H), 7.60 (d, 1H), 7.05 (d, 1H), 6.46 (d, 1H), 4.66 (t, 1H), 3.91 (s, 2H), 3.09 (d, 2H), 1.02 (s, 6H).

b) 6-Bromo-2-(3-chloro-2,2-dimethylpropyl)-1-oxo-1,2-dihydroisoquinoline-4-carbaldehyde A solution of 6-bromo-2-(3-hydroxy-2,2-dimethylpropyl)isoquinolin-1(2H)-one (Example 2a, 0.92 g) dissolved in DMF (5 ml) was treated with (chloromethylene)dimethylammonium chloride (1.90 g) in a sealed tube. The resulting mixture was stirred at 80° C. for 20 h. The reaction mixture was diluted with water (200 mL), and extracted with ethyl acetate (300 mL). The organic was dried (MgSO₄), filtered and evaporated to afford crude product. The crude product was purified (SiO₂ chromatography, elution with 50% diethyl ether in isohexane) to afford the subtitle compound (0.50 g) as a solid.

¹H NMR δ(DMSO-d₆) 9.78 (s, 1H), 9.28 (s, 1H), 8.26 (d, 1H), 7.85 (s, 1H), 7.70 (d, 1H), 4.19 (s, 2H), 3.45 (s, 2H), 1.16 (s, 6H).

c) N-Cyclopropyl-3-fluoro-5-(4-formyl-2-(3-hydroxy-2,2-dimethylpropyl)-1-oxo-1,2-dihydroisoquinolin-6-yl)-4-methylbenzamide A solution of 6-bromo-2-(3-chloro-2,2-dimethylpropyl)-1-oxo-1,2-dihydroisoquinoline-4-carbaldehyde (Example 2b, 0.50 g) dissolved in NMP (5 mL) was treated with potassium acetate (0.17 g) under nitrogen. The resulting mixture was stirred at 130° C. for 20 h. The mixture was then treated with N-cyclopropyl-3-fluoro-4-methyl-5-(4,4,5,5-tetramethyl-1,3,2-dioxaborolan-2-yl)benzamide (0.63 g), Pd-118 (0.046 g) and potassium carbonate (0.43 g) under nitrogen and stirred at 80° C. for 4 h. After cooling to room temperature methanol (10 mL) was added and the mixture stirred for 1 h. The reaction mixture was diluted with water (250 mL), and extracted with ethyl acetate (250 mL). The organic was dried (MgSO₄), filtered and evaporated to afford crude product. The crude product was purified (SiO₂ chromatography, elution with 100% ethyl acetate) to afford the subtitle compound (0.55 g) as an oil.

¹H NMR δ(CDCl₃) 9.84 (s, 1H), 9.02 (s, 1H), 8.51 (d, 1H), 7.76 (s, 1H), 7.56-7.38 (m, 3H), 6.39-6.29 (m, 1H), 4.09 (s, 2H), 3.94-3.86 (m, 1H), 3.22-3.16 (m, 2H), 2.93-2.87 (m, 1H), 2.25-2.19 (m, 3H), 1.09 (s, 6H), 0.91-0.83 (m, 2H), 0.67-0.59 (m, 2H).

d) N-Cyclopropyl-3-fluoro-5-{2-(3-hydroxy-2,2-dimethylpropyl)-4-[(4-methyl-1,4-diazepan-1-yl)methyl]-1-oxo-1,2-dihydroisoquinolin-6-yl}-4-methylbenzamide To a mixture of N-cyclopropyl-3-fluoro-5-(4-formyl-2-(3-hydroxy-2,2-dimethylpropyl)-1-oxo-1,2-dihydroisoquinolin-6-yl)-4-methylbenzamide (Example 2c, 0.20 g) and titanium(IV) isopropoxide (2 mL) was added 1-methyl-1,4-diazepane (0.17 mL) under nitrogen. The resulting mixture was stirred at 20° C. for 2 h before adding sodium triacetoxyborohydride (0.38 g). The mixture was stirred at room temperature for 2 h. TFA (5 mL) was added and the mixture stirred at room temperature for 72 h and then evaporated to dryness. The mixture was quenched with 10% aq ammonia (5 ml) and extracted with ethyl acetate. The organic was dried (MgSO₄), filtered and evaporated to afford crude product. The crude product was purified by preparative HPLC (Phenomenex Gemini column using a 95-5% gradient of aqueous 0.2% ammonia in acetonitrile as eluent) to afford the title compound (0.055 g) as a white solid.

MS: APCI(+ve) 549 (M+H)⁺.

¹H NMR δ (DMSO-d₆) 8.58 (s, 1H), 8.33 (d, 1H), 7.97 (s, 1H), 7.70-7.62 (m, 2H), 7.58-7.50 (m, 1H), 7.41 (s, 1H), 4.93-4.79 (m, 1H), 3.95 (s, 2H), 3.70 (s, 2H), 3.15 (s, 2H), 3.02-2.52 (m, 12H), 2.17 (s, 3H), 1.87-1.79 (m, 2H), 0.81 (s, 6H), 0.71-0.64 (m, 2H), 0.58-0.51 (m, 2H).

The following Examples 3 to 9 (Table 1) were prepared from 6-bromoisoquinolin-1(2H)-one (Example 1b), using a suitable alkylating agent (for R1) and a suitable (protected) amine (for Y) using similar methods to those described for Examples 1 and 2:

EXAMPLE 3

N-Cyclopropyl-3-fluoro-5-(4-(((3S)-3-(hydroxymethyl)piperazin-1-yl)methyl)-2-(3-hydroxypropyl)-1-oxo-1,2-dihydroisoquinolin-6-yl)-4-methylbenzamide

EXAMPLE 4

N-Cyclopropyl-3-fluoro-5-(2-(3-hydroxypropyl)-4-(((3S)-3-methylpiperazin-1-yl)methyl)-1-oxo-1,2-dihydroisoquinolin-6-yl)-4-methylbenzamide

EXAMPLE 5

N-Cyclopropyl-3-fluoro-5-(2-(2-hydroxyethyl)-1-oxo-4-(piperazin-1-ylmethyl)-1,2-dihydroisoquinolin-6-yl)-4-methylbenzamide

EXAMPLE 6

N-Cyclopropyl-3-fluoro-5-(2-(2-hydroxyethyl)-4-M3S)-3-methylpiperazin-1-yl)methyl)-1-oxo-1,2-dihydroisoquinolin-6-yl)-4-methylbenzamide

EXAMPLE 7

N-Cyclopropyl-3-fluoro-5-(2-(2-hydroxyethyl)-4-((4-methyl-1,4-diazepan-1-yl)methyl)-1-oxo-1,2-dihydroisoquinolin-6-yl)-4-methylbenzamide

EXAMPLE 8

N-Cyclopropyl-3-fluoro-5-{2-(4-hydroxybutyl)-4-[(4-methyl-1,4-diazepan-1-yl)methyl]-1-oxo-1,2-dihydroisoquinolin-6-yl}-4-methylbenzamide

EXAMPLE 9

N-Cyclopropyl-3-fluoro-5-{2-[(3S)-3-hydroxybutyl]-1-oxo-4-(piperazin-1-ylmethyl)-1,2-dihydroisoquinolin-6-yl}-4-methylbenzamide

TABLE 1

[Structure: cyclopropyl-NH-C(O)-phenyl(with F and methyl substituents)-isoquinolin-1(2H)-one with N-R1 and CH2-Y substituent]

| Example | R1 | Y | MS [M+H]+ m/z | ¹H NMR δ (DMSO-d₆) |
|---|---|---|---|---|
| 3 | ~~~(CH₂)₃OH | piperazinyl with (R)-CH₂OH substituent | 523 | 8.59-8.49(m, 1H), 8.34(d, 1H), 8.01(s, 1H), 7.70-7.63(m, 2H), 7.54(d, 1H), 7.45(s, 1H), 4.65(s, 1H), 4.53(s, 1H), 4.12-3.95(m, 2H), 3.52-3.40(m, 4H), 3.29-3.18(m, 2H), 2.89-2.77(m, 3H), 2.74-2.54(m, 3H), 2.21(s, 3H), 2.03-1.78(m, 4H), 0.74-0.65(m, 2H), 0.62-0.53(m, 2H) |
| 4 | ~~~(CH₂)₃OH | (S)-3-methylpiperazinyl | 507 | 8.56-8.50(m, 1H), 8.33(d, 1H), 7.94(s, 1H), 7.70-7.64(m, 2H), 7.54(d, 1H), 7.48(s, 1H), 4.65-4.56(m, 1H), 4.03(t, 2H), 3.59-3.42(m, 4H), 3.13-2.72(m, 5H), 2.25(s, 3H), 1.84(t, 2H), 1.06(d, 3H), 0.72-0.67(m, 2H), 0.60-0.54(m, 2H) |
| 5 | ~~~(CH₂)₂OH | piperazinyl | 479 | 8.54(d, 1H), 8.33(d, 1H), 7.98(s, 1H), 7.70-7.62(m, 2H), 7.53(d, 1H), 7.32(s, 1H), 4.97-4.77(m, 1H), 4.03(t, 2H), 3.69(t, 2H), 3.42(s, 2H), 2.90-2.83(m, 1H), 2.67-2.60(m, 4H), 2.37-2.30(m, 4H), 2.21(s, 3H), 0.73-0.66(m, 2H), 0.61-0.54(m, 2H) |
| 6 | ~~~(CH₂)₂OH | (R)-3-methylpiperazinyl | 493 | 8.50(d, 1H), 8.31(d, 1H), 7.96(s, 1H), 7.66-7.60(m, 2H), 7.50(d, 1H), 7.37(s, 1H), 4.91-4.80(m, 1H), 4.01(t, 2H), 3.67(t, 2H), 3.46(s, 2H), 2.87-2.80(m, 1H), 2.77-2.51(m, 4H), 2.24(s, 3H), 1.84(t, 2H), 1.51(t, 1H), 0.85(d, 3H), 0.70-0.63(m, 2H), 0.57-0.49(m, 2H) |
| 7 | ~~~(CH₂)₂OH | 4-methyl-1,4-diazepan-1-yl | 507 | 8.56(d, 1H), 8.33(d, 1H), 7.95(s, 1H), 7.71-7.66(m, 2H), 7.53(d, 1H), 7.39(s, 1H), 4.94-4.84(m, 1H), 4.10-3.99(m, 2H), 3.73-3.64(m, 4H), 3.04-2.65(m, 9H), 2.55(s, 3H), 2.19(s, 3H), 1.86-1.80(m, 2H), 0.73-0.66(m, 2H), 0.60-0.54(m, 2H) |

TABLE 1-continued

| Example | R1 | Y | MS [M+H]+ m/z | $^1$H NMR δ (DMSO-$d_6$) |
|---|---|---|---|---|
| 8 | ~~~~OH (4-carbon chain with OH) | N-(1,4-diazepane)-N-Me | 535 | 8.54(d, 1H), 8.33(d, 1H), 7.98 (s, 1H), 7.67-7.64(m, 2H), 7.53 (d, 1H), 7.44(s, 1H), 4.44(s, 1H), 3.98(t, 2H), 3.62(s, 2H), 3.42(s, 2H), 2.88-2.82(m, 1H), 2.67-2.44(m, 8H), 2.21(s, 3H), 2.19(s, 3H), 1.75-1.66(m, 4H), 1.48-1.39(m, 2H), 0.72-0.66 (m, 2H), 0.59-0.54(m, 2H) |
| 9 | ~~~~CH(Me)OH | piperazine-NH | 507 | 8.54(d, 1H), 8.33(d, 1H), 7.96(s, 1H), 7.69-7.64(m, 2H), 7.54(d, 1H), 7.41(s, 1H), 4.67-4.62(m, 1H), 4.13-3.91(m, 2H), 3.39-3.27(m, 4H), 2.89-2.81(m, 1H), 2.69-2.63(m, 3H), 2.55-2.46 (m, 3H), 2.41-2.30(m, 3H), 2.25 (s, 3H), 1.84-1.65(m, 2H), 1.12-1.06(m, 2H), 0.73-0.67(m, 2H), 0.59-0.55(m, 2H) |

EXAMPLE 10

N-Cyclopropyl-3-fluoro-5-[2-(3-hydroxypropyl)-1-oxo-4-(piperazin-1-ylmethyl)-1,2-dihydroisoquinolin-6-yl]-4-methylbenzamide

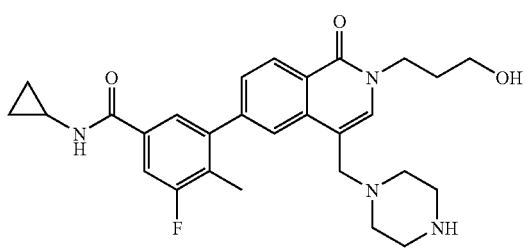

a) 6-Bromo-2-(3-chloropropyl)isoquinolin-1(2H)-one

A solution of 6-bromoisoquinolin-1(2H)-one (Example 1b) (2 g) dissolved in NMP (20 mL) was treated with potassium carbonate (1.974 g) and 1-bromo-3-chloropropane (8.83 ml) under nitrogen. The resulting mixture was stirred at 70° C. for 10 h. The cooled reaction mixture was diluted with water, and extracted with ethyl acetate. The organic layer was dried (MgSO$_4$), and evaporated. The residue was purified (SiO$_2$ chromatography, elution with a mixture of DCM and isohexane) to give the subtitle compound (1.70 g).

$^1$H NMR δ(DMSO-$d_6$) 8.12 (1H, d), 7.95 (1H, d), 7.64 (1H, dd), 7.51 (1H, d), 6.62 (1H, d), 4.10-4.03 (2H, m), 3.67 (1H, t), 3.54 (1H, t), 2.30-2.08 (2H, m).

b) 6-Bromo-2-(3-chloropropyl)-1-oxo-1,2-dihydroisoquinoline-4-carbaldehyde

Phosphorousoxychloride (2.37 mL) was added dropwise to DMF (10 mL) stirring at 0° C. The resulting mixture was warmed to room temperature over 2 h before being treated with a solution of 6-bromo-2-(3-chloropropyl)isoquinolin-1 (2H)-one (Example 10a, 0.85 g) in DMF (10 mL). The resulting solution was heated at 80° C. for 10 h. The cooled reaction was quenched with iced water and extracted with ethyl acetate. The organics were washed with brine, dried (MgSO$_4$) and concentrated in vacuo to give the subtitle compound (0.91 g).

$^1$H NMR δ(CDCl$_3$) d 9.74 (s, 1H), 9.27-9.22 (m, 1H), 8.26 (d, 1H), 7.74 (s, 1H), 7.69 (d, 1H), 4.29 (t, 2H), 3.61 (t, 2H), 2.40-2.28 (m, 2H).

c) 3-(6-Bromo-4-formyl-1-oxoisoquinolin-2(1H)-yl) propyl acetate

A solution of 6-bromo-2-(3-chloropropyl)-1-oxo-1,2-dihydroisoquinoline-4-carbaldehyde (Example 10b, 0.90 g) in DMSO (10 mL) was treated with sodium acetate (0.45 g) under nitrogen. The resulting mixture was stirred at 70° C. for 10 h. The cooled reaction mixture was diluted with water (250 mL), and extracted with ethyl acetate (250 mL). The organic was dried (MgSO$_4$), filtered and evaporated to afford subtitle compound. (0.91 g).

¹H NMR δ(CDCl₃) 9.80 (s, 1H), 9.27 (s, 1H), 8.27 (d, 1H), 7.74-7.67 (m, 2H), 4.22-4.15 (m, 4H), 2.23-2.16 (m, 2H), 2.08 (s, 3H).

d) 3-{6-[5-(Cyclopropylcarbamoyl)-3-fluoro-2-methylphenyl]-4-formyl-1-oxoisoquinolin-2(1H)-yl}propyl acetate 3-(6-Bromo-4-formyl-1-oxoisoquinolin-2(1H)-yl)propyl acetate (Example 10c, 0.90 g), potassium carbonate (1.06 g), N-cyclopropyl-3-fluoro-4-methyl-5-(4,4,5,5-tetramethyl-1,3,2-dioxaborolan-2-yl)benzamide (0.82 g) and Pd-118 (0.050 g) in DMF (10 ml) were heated under nitrogen at 70° C. for 12 h. The cooled reaction mixture was diluted with water and extracted with ethyl acetate. The organic layer was dried (MgSO₄), filtered and evaporated. The residue was purified (SiO₂ chromatography, elution with ethyl acetate) to afford the subtitle compound.

¹H NMR δ(DMSO-d₆) 9.78 (s, 1H), 8.91 (s, 1H), 8.55 (s, 2H), 8.38 (d, 1H), 7.72-7.64 (m, 3H), 4.23-4.02 (m, 4H), 2.88-2.82 (m, 1H), 2.17-2.09 (m, 5H), 1.93 (s, 3H), 0.73-0.67 (m, 2H), 0.59-0.54 (m, 2H).

e) N-Cyclopropyl-3-fluoro-5-[4-formyl-2-(3-hydroxypropyl)-1-oxo-1,2-dihydroisoquinolin-6-yl]-4-methylbenzamide 3-(6-(5-(Cyclopropylcarbamoyl)-3-fluoro-2-methylphenyl)-4-formyl-1-oxoisoquinolin-2(1H)-yl)propyl acetate (Example 10d, 0.75 g) was treated with methanol (15 mL) and potassium carbonate (0.25 g) and the resulting mixture was stirred at room temperature for 30 min, diluted with water and extracted with ethyl acetate. The organic layer was dried (MgSO₄), filtered and evaporated to afford the subtitle compound (0.67 g).

¹H NMR δ(DMSO-d₆) 9.78 (s, 1H), 8.91 (s, 1H), 8.55-8.51 (m, 2H), 8.38 (d, 1H), 7.72-7.63 (m, 3H), 4.65 (t, 1H), 4.18 (t, 2H), 3.50 (q, 2H), 2.89-2.82 (m, 1H), 2.16 (s, 3H), 1.93 (t, 2H), 0.73-0.66 (m, 2H), 0.59-0.54 (m, 2H).

f) N-Cyclopropyl-3-fluoro-5-[2-(3-hydroxypropyl)-1-oxo-4-(piperazin-1-ylmethyl)-1,2-dihydroisoquinolin-6-yl]-4-methylbenzamide N-Cyclopropyl-3-fluoro-5-(4-formyl-2-(3-hydroxypropyl)-1-oxo-1,2-dihydroisoquinolin-6-yl)-4-methylbenzamide (Example 10e, 0.34 g) and 1-Boc-piperazine (0.30 g) were stirred together in DCE (10 ml) the overall pH of the reaction was adjusted to pH 6 by dropwise addition of glacial acetic acid. The mixture was stirred for 24 h, sodium triacetoxyborohydride (0.51 g) was added, and the resulting mixture was stirred at room temperature for 24 h. A solution of HCl in dioxan (5 mL of 4M) was added and the reaction mixture stirred for 2 h, evaporated to dryness and the residue purified by reverse phase preparative HPLC (Phenomenex column using a gradient of aqueous 0.2% ammonia in acetonitrile as eluent) to give the title compound (0.11 g).

MS: APCI(+ve) 493 (M+H)⁺.

¹H NMR δ(DMSO-d₆) 8.53 (d, 1H), 8.33 (d, 1H), 8.00 (s, 1H), 7.69-7.61 (m, 2H), 7.54 (d, 1H), 7.45 (s, 1H), 4.64-4.56 (m, 1H), 4.02 (t, 2H), 3.49-3.41 (m, 4H), 2.89-2.81 (m, 1H), 2.67-2.59 (m, 4H), 2.36-2.28 (m, 4H), 2.28 (s, 3H), 1.88-1.81 (m, 2H), 0.73-0.65 (m, 2H), 0.61-0.52 (m, 2H).

EXAMPLE 11

N-Cyclopropyl-3-fluoro-5-(2-(3-hydroxy-2,2-dimethylpropyl)-4-(((3R)-3-(hydroxymethyl)piperazin-1-yl)methyl)-1-oxo-1,2-dihydroisoquinolin-6-yl)-4-methylbenzamide

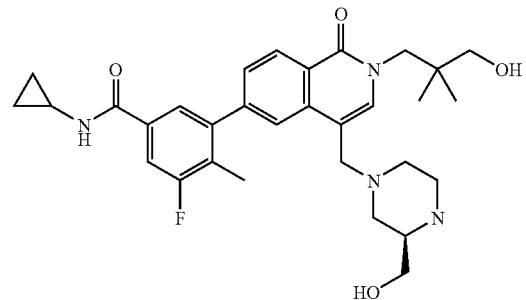

a) (E)-3-(3-Bromophenyl)but-2-enoic acid

To a stirred mixture of 60% sodium hydride (2.01 g) in dry THF (100 mL) was added triethyl phosphonoacetate (10.1 mL) at 0° C. under nitrogen. The resulting mixture was added dropwise to a solution of 1-(3-bromophenyl)ethanone (10.0 g) in THF (100 mL) at reflux and the reaction heated at reflux overnight. The reaction mixture was diluted with water (300 mL), and extracted with dichloromethane (350 mL). The organic was dried (MgSO₄), filtered and evaporated to afford a yellow oil. The oil was dissolved in methanol (100 mL), sodium hydroxide (6.03 g) and water (50 mL) added and the mixture was heated at 50° C. for 2 h. The reaction mixture was evaporated to leave an aqueous solution which was extracted twice with diethyl ether and the organic extracts were discarded. The aqueous solution was acidified with aqueous 2M HCl and then extracted with ethyl acetate (300 mL). The organic was dried (MgSO₄), filtered and evaporated to afford the subtitle compound (11.70 g) as a solid.

¹H NMR δ(DMSO-d₆) 12.38 (s, 1H), 7.75-7.14 (m, 4H), 6.03 (s, 1H), 2.41 (s, 3H).

b) 6-Bromo-4-methylisoquinolin-1(2H)-one

To a suspension of (E)-3-(3-bromophenyl)but-2-enoic acid (Example 11a, 11.70 g) in DCM (100 mL) and DMF (a few drops), cooled to 0° C., was added slowly a solution of oxalyl chloride (6.77 mL) in DCM (100 mL) and the reaction mixture was allowed to warm to room temperature and stirred overnight. The reaction mixture was evaporated and the residue taken up in dioxane (50 mL). After cooling to 0° C. a solution of sodium azide (9.47 g) in water (30 mL) was added dropwise. The resulting suspension was allowed to warm to room temperature and stirred for 2 h. The reaction was diluted with water (300 ml) and extracted with ethyl acetate (2×300 ml) and the combined organics were washed with saturated sodium bicarbonate solution (300 ml) and water (300 ml) and dried (MgSO₄).

The organic solution was filtered, 1,2-dichlorobenzene (50 mL) added and the solution was concentrated to constant volume under vacuum [CAUTION—never concentrate to complete dryness]. The acyl azide solution in 1,2-dichlorobenzene (~50 mL) was added dropwise over 30 min to a solution of iodine (0.90 g) in 1,2-dichlorobenzene (50 mL) at 120° C. (internal temperature). After addition was complete, the dark solution was heated at 190° C. for 24 h. The reaction mixture was allowed to cool and then isohexane (500 mL) was added and the mixture stirred for 1 h. The resulting precipitate was collected by filtration, washed with diethyl ether and dried in vacuo to give the subtitle compound (5.50 g) as a beige solid.

$^1$H NMR δ (DMSO-$d_6$) 11.30 (s, 1H), 8.14 (d, 1H), 7.74-7.58 (m, 1H), 7.47-7.31 (m, 1H), 7.07 (d, 1H), 2.26 (s, 3H).

c) 6-Bromo-4-methyl-2-(phenylsulfonyl)isoquinolin-1(2H)-one

A solution of 6-bromo-4-methylisoquinolin-1(2H)-one (Example 11b, 5.4 g) dissolved in THF (10 mL) was treated with 60% sodium hydride (1.00 g) and stirred for 1 h before evaporating to dryness. The residue was dissolved in THF (10 mL) before adding benzenesulfonyl chloride (3.22 mL) under nitrogen. The resulting mixture was stirred at room temperature for 16 h. The reaction mixture was diluted with ethyl acetate and washed with water. The organic layer was dried (MgSO$_4$), filtered and evaporated to afford the crude product. The crude product was purified (SiO$_2$ chromatography, elution with 50% DCM in isohexane). Pure fractions were evaporated to dryness to afford the subtitle compound (4.65 g) as a yellow solid.

$^1$H NMR δ(CDCl$_3$) 8.18-8.03 (m, 3H), 7.79-7.42 (m, 6H), 2.33 (s, 3H).

d) 6-Bromo-4-(bromomethyl)-2-(phenylsulfonyl)isoquinolin-1(2H)-one

A solution of 6-bromo-4-methyl-2-(phenylsulfonyl)isoquinolin-1(2H)-one (Example 11c, 4.55 g) in benzene (40 mL) was treated with N-bromosuccinimide (3.00 g) and benzoyl peroxide (0.291 g) under nitrogen. The resulting solution was heated at 80° C. for 3 h. The cooled reaction mixture was evaporated to dryness. Purification (SiO$_2$ chromatography, elution with 60% DCM in isohexane) afforded the subtitle compound (3.40 g) as a white solid.

$^1$H NMR δ(CDCl$_3$) 7.29-7.19 (m, 4H), 7.95 (s, 1H), 7.74-7.54 (m, 4H), 4.61 (s, 2H).

e) tert-Butyl-(2R)-4-((6-bromo-1-oxo-2-(phenylsulfonyl)-1,2-dihydroisoquinolin-4-yl)methyl)-2-(hydroxymethyl)piperazine-1-carboxylate A solution of 6-bromo-4-(bromomethyl)-2-(phenylsulfonyl)isoquinolin-1(2H)-one (Example 11d, 1.75 g) in THF (20 mL) was treated with (R)-tert-butyl ethyl(1-hydroxy-3-(methylamino)propan-2-yl)carbamate (0.98 g) and N,N-diisopropylethylamine (0.80 mL) under nitrogen. The resulting solution was stirred at 50° C. for 1 h. The reaction mixture was diluted with water (300 mL), and extracted with ethyl acetate (250 mL×2). The combined organics were dried (MgSO$_4$), filtered and evaporated. Triturated with diethyl ether/isohexane (1:1) afforded the subtitle compound (2.30 g) as a solid.

$^1$H NMR δ(CDCl$_3$) 8.16-8.10 (m, 3H), 8.06 (s, 1H), 7.90 (s, 1H), 7.71-7.65 (m, 1H), 7.60-7.54 (m, 3H), 4.23-4.16 (m, 1H), 3.84 (d, 2H), 3.59-3.45 (m, 2H), 3.21-3.02 (m, 2H), 2.89-2.79 (m, 1H), 2.33-2.09 (m, 3H), 1.51 (s, 9H).

f) tert-Butyl-(2R)-4-((6-(5-(cyclopropylcarbamoyl)-3-fluoro-2-methylphenyl)-1-oxo-1,2-dihydroisoquinolin-4-yl)methyl)-2-(hydroxymethyl)piperazine-1-carboxylate A solution of tert-butyl-(2R)-4-((6-bromo-1-oxo-2-(phenylsulfonyl)-1,2-dihydroisoquinolin-4-yl)methyl)-2-(hydroxymethyl)piperazine-1-carboxylate (Example 11e, 2.3 g) in DMF (20 mL) was treated with N-cyclopropyl-3-fluoro-4-methyl-5-(4,4,5,5-tetramethyl-1,3,2-dioxaborolan-2-yl)benzamide (1.24 g), Pd-118 (0.08 g) and potassium carbonate (0.86 g) under nitrogen. The resulting mixture was heated at 80° C. for 10 h. The reaction mixture was diluted with water (300 mL), acidified with acetic acid (to pH 5) and extracted with ethyl acetate (300 mL). The organic was dried (MgSO$_4$), filtered and evaporated to afford crude product. Purification (SiO$_2$ chromatography, elution with 1% AcOH in ethyl acetate) afforded the subtitle compound (0.60 g) as a solid.

MS: APCI(+ve) 565 (M+H)$^+$.

g) N-Cyclopropyl-3-fluoro-5-(2-(3-hydroxy-2,2-dimethylpropyl)-4-(((3R)-3-(hydroxymethyl)piperazin-1-yl)methyl)-1-oxo-1,2-dihydroisoquinolin-6-yl)-4-methylbenzamide A solution of (R)-tert-butyl 4-((6-(5-(cyclopropylcarbamoyl)-3-fluoro-2-methylphenyl)-1-oxo-1,2-dihydroisoquinolin-4-yl)methyl)-2-(hydroxymethyl)piperazine-1-carboxylate (Example 11f, 0.15 g) dissolved in NMP (3 mL) was treated with cesium carbonate (0.43 g) and 3-bromo-2,2-dimethylpropan-1-ol (0.22 g) under nitrogen and the reaction heated at 100° C. for 8 h. The reaction mixture was diluted with water (200 mL), and extracted with ethyl acetate (200 mL). The organic was dried (MgSO$_4$), filtered and evaporated. The crude product was treated with DCM:TFA (1:1, 5 mL) and stirred at room temperature for 1 h before evaporating to dryness. The crude material was dissolved in methanol (5 mL), acidified with acetic acid (1 mL) and loaded onto an 10 g SCX cartridge. The cartridge was eluted with methanol (50 mL) (discarded) and then with 20% 880 ammonia in methanol (50 mL) to afford after evaporation of relevant fractions the subtitle product. Purification by preparative HPLC (Phenomenex Gemini column using a 95-5% gradient of aqueous 0.2% ammonia in acetonitrile as eluent) afforded the title compound (0.055 g) as a white solid.

MS: APCI(+ve) 551 (M+H)$^+$.

$^1$H NMR δ (DMSO-$d_6$) 8.53 (d, 1H), 8.35 (d, 1H), 8.01 (s, 1H), 7.72-7.62 (m, 2H), 7.55 (d, 1H), 7.39 (s, 1H), 4.87 (t, 1H), 4.47 (t, 1H), 3.99-3.85 (m, 2H), 3.55-3.41 (m, 2H), 3.27-3.19 (m, 2H), 3.12 (d, 2H), 2.92-2.53 (m, 4H), 2.22 (s, 3H), 1.95-1.89 (m, 1H), 1.65-1.58 (t, 1H), 0.82 (s, 6H), 0.74-0.65 (m, 2H), 0.61-0.52 (m, 2H).

The following Examples 12 to 25 (Table 2) were prepared using 6-bromo-4-(bromomethyl)-2-(phenylsulfonyl)isoquinolin-1(2H)-one (Example 11d), a suitable amine (for Y), followed by a suitable alkylating agent (for R1) using a similar method to that described in Example 11.

EXAMPLE 12

N-Cyclopropyl-3-fluoro-5-(2-((1-(hydroxymethyl)cyclopropyl)methyl)-4-(((3R)-3-(hydroxymethyl)piperazin-1-yl)methyl)-1-oxo-1,2-dihydroisoquinolin-6-yl)-4-methylbenzamide

EXAMPLE 13

N-Cyclopropyl-3-fluoro-5-(4-((3-(hydroxymethyl)piperazin-1-yl)methyl)-2-(((3R)-3-methoxypropyl)-1-oxo-1,2-dihydroisoquinolin-6-yl)-4-methylbenzamide

EXAMPLE 14

N-Cyclopropyl-3-fluoro-5-(2-(3-hydroxy-3-methylbutyl)-4-(((3R)-3-(hydroxymethyl)piperazin-1-yl)methyl)-1-oxo-1,2-dihydroisoquinolin-6-yl)-4-methylbenzamide

EXAMPLE 15

N-Cyclopropyl-3-fluoro-5-(2-((1-(hydroxymethyl)cyclopropyl)methyl)-4-(((3S)-3-(hydroxymethyl)piperazin-1-yl)methyl)-1-oxo-1,2-dihydroisoquinolin-6-yl)-4-methylbenzamide

EXAMPLE 16

N-Cyclopropyl-3-fluoro-5-(2-((1-(hydroxymethyl)cyclopropyl)methyl)-4-(((2R)-2-(hydroxymethyl)piperazin-1-yl)methyl)-1-oxo-1,2-dihydroisoquinolin-6-yl)-4-methylbenzamide

EXAMPLE 17

N-Cyclopropyl-3-fluoro-5-(2-(3-hydroxy-2,2-dimethylpropyl)-4-(((3S)-3-(hydroxymethyl)piperazin-1-yl)methyl)-1-oxo-1,2-dihydroisoquinolin-6-yl)-4-methylbenzamide

EXAMPLE 18

N-Cyclopropyl-3-fluoro-5-{2-[(2S)-3-hydroxy-2-methylpropyl]-1-oxo-4-(piperazin-1-ylmethyl)-1,2-dihydroisoquinolin-6-yl}-4-methylbenzamide

EXAMPLE 19

N-Cyclopropyl-3-fluoro-5-[2-{[1-(hydroxymethyl)cyclopropyl]methyl}-1-oxo-4-(piperazin-1-ylmethyl)-1,2-dihydroisoquinolin-6-yl]-4-methylbenzamide

EXAMPLE 20

N-Cyclopropyl-3-fluoro-5-{2-[(2R)-3-hydroxy-2-methylpropyl]-1-oxo-4-(piperazin-1-ylmethyl)-1,2-dihydroisoquinolin-6-yl}-4-methylbenzamide

EXAMPLE 21

N-Cyclopropyl-3-fluoro-5-[2-(3-hydroxy-2,2-dimethylpropyl)-4-{[(2S)-2-(hydroxymethyl)piperazin-1-yl]methyl}-1-oxo-1,2-dihydroisoquinolin-6-yl]-4-methylbenzamide

EXAMPLE 22

N-Cyclopropyl-3-fluoro-5-[2-(3-hydroxy-2,2-dimethylpropyl)-4-{[(2R)-2-(hydroxymethyl)piperazin-1-yl]methyl}-1-oxo-1,2-dihydroisoquinolin-6-yl]-4-methylbenzamide

EXAMPLE 23

N-Cyclopropyl-3-[4-(1,4-diazepan-1-ylmethyl)-2-(3-hydroxy-2,2-dimethylpropyl)-1-oxo-1,2-dihydroisoquinolin-6-yl]-5-fluoro-4-methylbenzamide

EXAMPLE 24

N-Cyclopropyl-3-fluoro-5-{2-(3-hydroxy-2,2-dimethylpropyl)-4-[(4-methylpiperazin-1-yl)methyl]-1-oxo-1,2-dihydroisoquinolin-6-yl}-4-methylbenzamide

EXAMPLE 25

3-[4-{[(3S)-3-Aminopiperidin-1-yl]methyl}-2-(3-hydroxy-2,2-dimethylpropyl)-1-oxo-1,2-dihydroisoquinolin-6-yl]-N-cyclopropyl-5-fluoro-4-methylbenzamide

TABLE 2

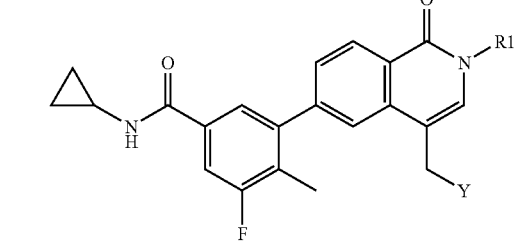

| Example | R1 | Y | MS [M + H]+ m/z | 1H NMR δ (DMSO-d6) unless indicated |
|---|---|---|---|---|
| 12 | (1-(hydroxymethyl)cyclopropyl)methyl | (3-(hydroxymethyl)piperazin-1-yl)methyl | 549 | 8.54(d, 1H), 8.34(d, 1H), 8.01 (s, 1H), 7.73-7.62(m, 2H), 7.54 (d, 1H), 7.47(s, 1H), 4.75-4.65 (m, 1H), 4.54-4.44(m, 1H), 4.03 (q, 2H), 3.55-3.45(m, 2H), 3.27-3.17(m ,5H), 2.92-2.54(m, 7H), 2.19(s, 3H), 0.75-0.64(m, 4H), 0.62-0.51(m, 2H), 0.47-0.36(m, 2H) |

TABLE 2-continued

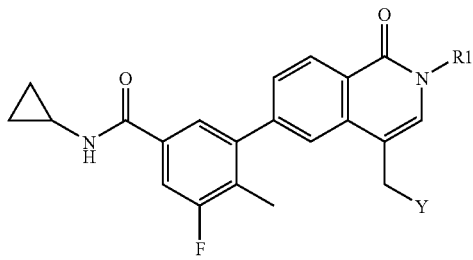

| Example | R1 | Y | MS [M + H]+ m/z | 1H NMR δ (DMSO-d6) unless indicated |
|---|---|---|---|---|
| 13 | ~~~~O~~~ | ~~~N(piperazine-CH2OH)~~~ | 537 | 8.55(s, 1H), 8.31(d, 1H), 7.97 (s, 1H), 7.66-7.61(m, 2H), 7.52 (d, 1H), 7.38(s, 1H), 4.46-4.40 (m, 1H), 3.99(t, 2H), 3.50-3.39 (m, 2H), 3.16(s, 6H), 2.86-2.51 (m, 7H), 2.20(s, 3H), 1.95-1.84 (m, 4H), 0.71-0.64(m, 2H), 0.58-0.51(m, 2H) |
| 14 | ~~~C(CH3)2OH~~~ | ~~~N(piperazine-CH2OH)~~~ | 551 | 8.55(d, 1H), 8.33(d, 1H), 8.00 (s, 1H), 7.69-7.63(m, 2H), 7.54 (d, 1H), 7.44(s, 1H), 4.51-4.39 (m, 2H), 4.10-3.98(m, 2H), 3.54-3.42(m, 2H), 3.27-3.18(m, 2H), 2.91-2.54(m, 6H), 2.28(s, 3H), 2.04-1.72(m, 4H), 1.22(s, 6H), 0.74-0.65(m, 2H), 0.60-0.53(m, 2H) |
| 15 | ~~~cyclopropyl-CH2OH~~~ | ~~~N(piperazine-CH2OH)~~~ | 549 | 8.53(d, 1H), 8.34(d, 1H), 7.98 (s, 1H), 7.69-7.65(m, 2H), 7.54 (d, 1H), 7.44(s, 1H), 4.74(m, 1H), 4.50-4.42(m, 1H), 4.04(q, 2H), 3.54-3.44(m, 2H), 3.26-3.18(m, 5H), 2.89-2.78(m, 2H), 2.73-2.54(m, 2H), 2.27(s, 3H), 2.02-1.89(m, 2H), 1.63(t, 1H), 0.73-0.65(m, 4H), 0.59-0.54 (m, 2H), 0.45-0.40(m, 2H) |
| 16 | ~~~cyclopropyl-CH2OH~~~ | ~~~N(piperazine-CH2OH)~~~ | 549 | 8.52(d, 1H), 8.33(d, 1H), 8.14 (s, 1H), 7.69-7.62(m, 2H), 7.54 (d, 1H), 7.46(s, 1H), 4.73-4.68 (m, 1H), 4.59-4.52(m, 1H), 4.24 (d, 1H), 4.00(s, 2H), 3.71-3.51 (m, 2H), 3.25-3.16(m, 5H), 2.90-2.77(m, 2H), 2.68-2.54(m, 2H), 2.23(s, 3H), 2.08-2.01(m, 2H), 0.73-0.65(m, 4H), 0.59-0.53(m, 2H), 0.45-0.39(m, 2H) |
| 17 | ~~~C(CH3)2CH2OH~~~ | ~~~N(piperazine-CH2OH)~~~ | 551 | 8.53(d, 1H), 8.35(d, 1H), 7.99 (s, 1H), 7.68-7.63(m, 2H), 7.59-7.54(m, 1H), 7.39-7.33(m, 1H), 4.86(t, 1H), 4.46(t, 1H), 3.92(t, 2H), 3.53-3.44(m, 2H), 3.25-3.09(m, 5H), 2.89-2.77 (m, 4H), 2.72-2.54(m, 2H), 2.29 (s, 3H), 1.92(t, 1H), 1.62(t, 1H), 0.90(s, 6H), 0.72-0.65(m, 2H), 0.60-0.53(m, 2H) |

TABLE 2-continued
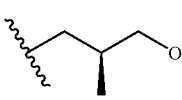
| Example | R1 | Y | MS [M + H]+ m/z | 1H NMR δ (DMSO-d6) unless indicated |
|---|---|---|---|---|
| 18 | 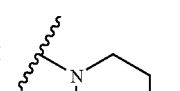 |  | 507 | 8.35(d, 1H), 8.28-8.24(m, 1H), 7.87(s, 1H), 7.65-7.63(m, 2H), 7.51(d, 1H), 7.41(s, 1H), 4.05-3.85(m, 4H), 3.36-3.35(m, 1H), 3.08-3.01(m, 2H), 2.89-2.85 (m, 1H), 2.67-2.65(m, 2H), 2.49-2.47(m, 6H), 2.32-2.30(m, 3H), 2.22(s, 3H), 0.89(d, 2H), 0.72-0.67(m, 2H), 0.60-0.56 (m, 2H) |
| 19 | 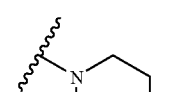 | 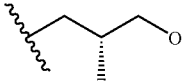 | 519 | 8.54(d, 1H), 8.34(d, 1H), 7.97 (s, 1H), 7.68-7.65(m, 2H), 7.55 (d, 1H), 7.42(s, 1H), 4.73-4.69 (m, 1H), 4.04(s, 2H), 3.52-3.44 (m, 2H), 3.23-3.21(m, 2H), 2.89-2.81(m, 1H), 2.68-2.56(m, 3H), 2.51-2.49(m, 3H), 2.37-2.29(m, 3H), 2.26(s, 3H), 0.73-0.64(m, 4H), 0.62-0.54(m, 2H), 0.44-0.41(m, 2H) |
| 20 | 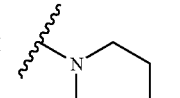 |  | 507 | 8.55(d, 1H), 8.33(d, 1H), 7.97 (s, 1H), 7.68-7.65(m, 2H), 7.55 (d, 1H), 7.38(s, 1H), 4.67-4.57 (m, 1H), 3.98-3.81(m, 2H), 3.47-3.17(m, 4H), 2.89-2.83(m, 1H), 2.63(s, 2H), 2.54-2.47(m, 6H), 2.34-2.28(m, 3H), 2.26(s, 3H), 1.29-1.19(m, 2H), 0.86(d, 2H), 0.73-0.64(m, 1H), 0.59-0.54(m, 1H) |
| 21 | 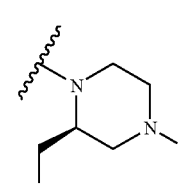 |  | 551 | 8.57-8.50(m, 1H), 8.38-8.31 (m, 1H), 7.98-7.89(m, 1H), 7.70-7.61(m, 2H), 7.57-7.49(m, 1H), 7.39(s, 1H), 3.98-3.85(m, 2H), 3.54-3.44(m, 2H), 3.26-3.08(m, 7H), 2.90-2.66(m, 3H), 2.22(s, 3H), 1.64-1.50(m, 2H), 0.85(s, 6H), 0.72-0.64(m, 2H), 0.61-0.52(m, 2H) |
| 22 | 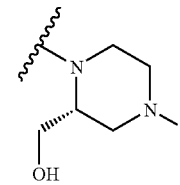 |  | 551 | 8.68-8.58(m, 1H), 8.34(d, 1H), 8.08(s, 1H), 7.70-7.64(m, 2H), 7.57-7.51(m, 1H), 7.43(s, 1H), 3.99-3.84(m, 2H), 3.54-3.44 (m, 2H), 3.24-3.06(m, 9H), 2.91-2.62(m, 3H), 2.30(s, 3H), 1.65-1.50(m, 2H), 0.90(s, 6H), 0.70-0.65(m, 2H), 0.61-0.56(m, 2H) |
| 23 | 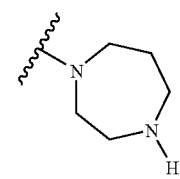 |  | 535 | 8.52(d, 1H), 8.35(d, 1H), 8.00-7.96(m, 1H), 7.68-7.64(m, 2H), 7.55(d, 1H), 7.39(s, 1H), 4.90 (s, 1H), 3.95(s, 2H), 3.69(s, 2H), 3.15(s, 2H), 2.89-2.59(m, 9H), 2.26(s, 3H), 1.68-1.62(m, 2H), 091(s, 6H), 0.72-0.66(m, 2H), 0.59-0.53(m, 2H) |

TABLE 2-continued

| Example | R1 | Y | MS [M + H]+ m/z | 1H NMR δ (DMSO-d6) unless indicated |
|---|---|---|---|---|
| 24 | (2,2-dimethyl-3-hydroxypropyl) | 4-methylpiperazin-1-yl | 535 | (CD3OD) 8.38(d, 1H), 7.97(d, 1H), 7.60(s, 1H), 7.52(d, 1H), 7.48(d, 1H), 7.33(s, 1H), 3.96 (s, 2H), 3.57(s, 2H), 3.29 (quintet, 1H), 3.18(s, 2H), 2.82 (dquintet, 1H), 2.67-2.27(m, 8H), 2.24-2.22(m, 6H), 0.95(s, 6H), 0.80-0.73(m, 2H), 0.64-0.58(m, 2H) |
| 25 | (2,2-dimethyl-3-hydroxypropyl) | (3R)-3-aminopiperidin-1-yl | 535 | (CD3OD) 8.38(d, 1H), 7.97(d, 1H), 7.60(d, 1H), 7.54(dd, 1H), 7.49(dd, 1H), 7.32(s, 1H), 3.97 (dd, 2H), 3.55(s, 2H), 3.19(s, 2H), 2.82(dq, 2H), 2.79-2.71 (m, 1H), 2.70-2.62(m, 1H), 2.22 (d, 3H), 2.15-2.04(m, 1H), 1.97-1.87(m, 1H), 1.85-1.76(m, 1H), 1.72-1.63(m, 1H), 1.55-1.41(m, 1H), 1.22-1.09(m, 1H), 0.96(s, 6H), 0.77(td, 2H), 0.64-0.58(m, 2H) |

EXAMPLE 26

N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide

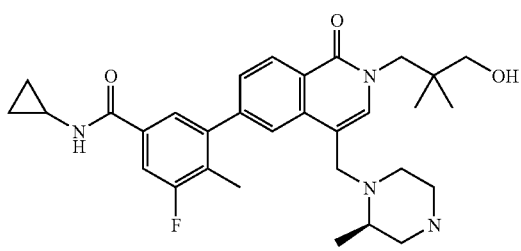

a) 6-Bromoisoquinolin-1(2H)-one

A solution of 4-bromo-2-methylbenzonitrile (26 g) dissolved in 1-tert-butoxy-N,N,N',N'-tetramethylmethanediamine (47.9 mL) was stirred at 140° C. for 2 h (flask open to evaporate t-butanol). The reaction mixture was cooled to room temperature, diluted with water (600 mL), and extracted with ethyl acetate (500 mL). The aqueous was further extracted with ethyl acetate (250 mL), the combined organics were washed with water (500 mL), brine (150 mL), dried (MgSO4) filtered and evaporated. The residual oil was dissolved in ethanol (250 mL) at 80° C. and treated with 37% hydrochloric acid (250 mL) at such a rate as to maintain a solution. The reaction mixture was stirred at 110° C. for 3 h, cooled to room temperature, diluted with water (600 mL) and the resulting suspension stirred for 2 h and filtered. The filtered solid was slurried in diethyl ether (400 mL) for 2 h, filtered and dried to give the subtitle compound (26.4 g) as a solid.

1H NMR δ(DMSO-d6) 11.43 (s, 1H), 8.12-8.03 (m, 1H), 7.98-7.88 (m, 1H), 7.62 (d, 1H), 7.27-7.18 (m, 1H), 6.57-6.47 (m, 1H).

b) 6-Bromo-2-(3-{[tert-butyl(dimethyl)silyl]oxy}-2,2-dimethylpropyl)isoquinolin-1(2H)-one Cesium carbonate (53.3 g) and (3-bromo-2,2-dimethylpropoxy)(tert-butyl)dimethylsilane (27.62 g) were added to a solution of 6-bromoisoquinolin-1(2H)-one (Example 26a, 18.33 g) in DMF (125 mL) with stirring at room temperature under nitrogen. The resulting mixture was stirred at 100° C. for 6 h, diluted with water (300 mL), and extracted with diethyl ether (300 mL×3). The combined organic extracts were dried (MgSO4), filtered and evaporated.

The residue was purified (SiO2 chromatography, elution with 0-8% ethyl acetate/isohexane) to give the subtitle compound (24.8 g) as a solid.

MS: APCI(+ve) 424/6 (M+H)+.

1H NMR δ(CDCl3) 8.20 (d, 1H), 7.58 (d, 1H), 7.47 (dd, 1H), 7.19 (d, 1H), 6.25 (d, 1H), 3.90 (s, 2H), 3.23 (s, 2H), 0.88 (s, 9H), 0.86 (s, 6H), 0.02 (s, 6H).

c) 6-Bromo-2-(3-chloro-2,2-dimethylpropyl)-1-oxo-1,2-dihydroisoquinoline-4-carbaldehyde Phosphorus oxychloride (104 mL) was added to an ice cooled solution of DMF (180 mL) over 1 h and the resulting mixture stirred at room temperature for 1.5 h before adding dropwise to a solution of 6-bromo-2-(3-{[tert-butyl(dimethyl)silyl]oxy}-2,2-dimethylpropyl)isoquinolin-1(2H)-one (Example 26b, 31.7 g) in DMF (70 mL) under nitrogen. The resulting solution was stirred at 85° C. for 20 h. The cooled reaction mixture was poured onto ice/water (2 L) and stirred for 1 h.

The supernatant was decanted off and the residual solid was dissolved in DCM (1 L) the organic layer was separated from residual water and dried ($Na_2SO_4$), filtered and evaporated. The residue was triturated with diethyl ether (200 mL) for 1 h, filtered and dried to give the subtitle compound (22.7 g) as a solid.

$^1$H NMR δ($CDCl_3$) 9.77 (s, 1H), 9.26 (s, 1H), 8.26 (d, 1H), 7.84 (s, 1H), 7.69 (d, 1H), 4.18 (s, 2H), 3.47 (s, 2H), 1.16 (s, 6H).

d) 6-Bromo-2-(3-hydroxy-2,2-dimethylpropyl)-1-oxo-1,2-dihydroisoquinoline-4-carbaldehyde A solution of 6-bromo-2-(3-chloro-2,2-dimethylpropyl)-1-oxo-1,2-dihydroisoquinoline-4-carbaldehyde (Example 26c, 20 g) in DMSO (140 mL) was treated with sodium acetate (55 g) under nitrogen. The resulting mixture was stirred at 135° C. for 48 h during which more sodium acetate was added after 6 h (55 g), 24 h (55 g) then 30 h (22.5 g).

The reaction mixture was cooled to 100° C. and poured onto water (2 L), and extracted into DCM (3×600 mL). The combined organics were washed with water, dried ($Na_2SO_4$), filtered and evaporated. The residue was suspended in methanol (120 mL), treated with potassium carbonate (7.7 g). After stirring for 1 h at room temperature this mixture was treated with silica (30 g) and evaporated to dryness. This residue was purified ($SiO_2$ chromatography, elution with 0 to 8% methanol in DCM) to give the subtitle compound (12.7 g) as a solid.

$^1$H NMR δ(DMSO-$d_6$) 9.73 (s, 1H), 9.12 (d, 1H), 8.35 (s, 1H), 8.20 (d, 1H), 7.80 (dd, 1H), 4.89 (t, 1H), 4.02 (s, 2H), 3.18 (d, 2H), 0.87 (s, 6H).

e) N-Cyclopropyl-3-fluoro-5-[4-formyl-2-(3-hydroxy-2,2-dimethylpropyl)-1-oxo-1,2-dihydroisoquinolin-6-yl]-4-methylbenzamide 6-Bromo-2-(3-hydroxy-2,2-dimethylpropyl)-1-oxo-1,2-dihydroisoquinoline-4-carbaldehyde (Example 26d 16.8 g), N-cyclopropyl-3-fluoro-4-methyl-5-(4,4,5,5-tetramethyl-1,3,2-dioxaborolan-2-yl)benzamide (20.61 g), Pd-118 (1.619 g) and potassium carbonate (17.16 g) in DMF (140 mL) was heated to 70° C. for 4 h under nitrogen. The mixture was cooled, diluted with water (250 mL), and extracted with ethyl acetate (300 mL). The separated organic layer was dried ($MgSO_4$), filtered and evaporated. The residue was purified ($SiO_2$ chromatography, elution with 50 to 100% ethyl acetate in DCM) to give a solid, which was triturated with isohexane 1:1 diethyl ether (200 mL) for 1 h. The suspension was filtered and dried to give the subtitle compound (14.5 g) as a solid.

$^1$H NMR δ(DMSO-$d_6$) 9.81 (s, 1H), 8.94 (s, 1H), 8.56 (s, 1H), 8.41-8.34 (m, 2H), 7.72-7.62 (m, 3H), 4.94-4.87 (m, 1H), 4.11 (s, 2H), 3.24-3.17 (m, 2H), 2.89-2.82 (m, 1H), 2.22 (s, 3H), 0.94 (s, 6H), 0.73-0.65 (m, 2H), 0.60-0.53 (m, 2H).

f) 3-[2-(3-{[tert-Butyl(dimethyl)silyl]oxy}-2,2-dimethylpropyl)-4-formyl-1-oxo-1,2-dihydroisoquinolin-6-yl]-N-cyclopropyl-5-fluoro-4-methylbenzamide A solution of N-cyclopropyl-3-fluoro-5-[4-formyl-2-(3-hydroxy-2,2-dimethylpropyl)-1-oxo-1,2-dihydroisoquinolin-6-yl]-4-methylbenzamide (Example 26e, 14.54 g) in DMF (120 mL) was treated with tert-butyldimethylchlorosilane (4.86 g) and imidazole (2.19 g) under nitrogen. The resulting mixture was stirred at room temperature for 1 h. More tert-butyldimethylchlorosilane (1.2 g) was added and the reaction mixture stirred at room temperature for 30 min, diluted with water (300 mL) and extracted with DCM (250 mL×2). The organics were dried ($MgSO_4$), filtered and evaporated. The residue was purified ($SiO_2$ chromatography, elution with 100% diethyl ether) to give the subtitle compound (15.20 g) as a gum.

MS: APCI(+ve) 565 (M+H)$^+$.

$^1$H NMR δ($CDCl_3$) 9.75 (s, 1H), 9.00 (s, 1H), 8.47 (d, 1H), 7.98 (s, 1H), 7.55-7.45 (m, 2H), 7.43 (s, 1H), 6.34 (s, 1H), 4.16 (s, 2H), 3.38 (s, 2H), 2.93-2.87 (m, 1H), 2.24 (s, 3H), 1.01 (s, 9H), 0.95 (s, 6H), 0.89 (s, 2H), 0.66-0.60 (m, 2H), 0.11 (d, 6H).

g) 3-[2-(3-{[tert-Butyl(dimethyl)silyl]oxy}-2,2-dimethylpropyl)-4-(hydroxymethyl)-1-oxo-1,2-dihydroisoquinolin-6-yl]-N-cyclopropyl-5-fluoro-4-methylbenzamide Sodium borohydride (0.804 g) was added to a stirred solution of 3-[2-(3-{[tert-butyl(dimethyl)silyl]oxy}-2,2-dimethylpropyl)-4-formyl-1-oxo-1,2-dihydroisoquinolin-6-yl]-N-cyclopropyl-5-fluoro-4-methylbenzamide (Example 26f, 8 g) in ethanol (80 mL) at room temperature under nitrogen. After 5 min, saturated aqueous $NaHCO_3$ (40 mL) was added and the mixture extracted with ethyl acetate (100 mL). The organic layer was washed with water (40 mL), dried ($Na_2SO_4$), filtered and evaporated. The residue was purified ($SiO_2$ chromatography, elution with 5-50% ethyl acetate in isohexane) to give the subtitle compound (5.72 g) as a solid.

$^1$H NMR δ(DMSO-$d_6$) 8.52 (d, 1H), 8.34 (d, 1H), 7.78 (d, 1H), 7.69-7.65 (m, 2H), 7.53 (dd, 1H), 7.35 (s, 1H), 5.12 (t, 1H), 4.57 (d, 2H), 3.93 (s, 2H), 3.35 (s, 2H), 2.90-2.81 (m, 1H), 2.19 (d, 3H), 0.92 (s, 9H), 0.88 (s, 6H), 0.72-0.66 (m, 2H), 0.59-0.54 (m, 2H), 0.08 (s, 6H).

h) N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide Methanesulfonyl chloride (0.55 mL) was added to a solution of 3-[2-(3-{[tert-butyl(dimethyl)silyl]oxy}-2,2-dimethylpropyl)-4-(hydroxymethyl)-1-oxo-1,2-dihydroisoquinolin-6-yl]-N-cyclopropyl-5-fluoro-4-methylbenzamide (Example 26 g, 3.65 g) and triethylamine (1.79 mL) in DCM (10 mL) at −20° C. After 30 min the solution was warmed to 0° C. and tert-butyl (3R)-3-methylpiperazine-1-carboxylate (2.58 g) was added. The reaction was stirred for 18 h at room temperature, evaporated and the residue purified ($SiO_2$ chromatography, elution with 20 to 80% ethyl acetate in isohexane). Fractions containing product were evaporated, dissolved in THF (100 mL) and treated with 4 M HCl in dioxane (5 mL), stirred at room temperature for 60 h, evaporated to dryness and the residue purified ($SiO_2$ chromatography, elution with 5 to 10% 7N $NH_3$/methanol in DCM) to give the title compound (1.53 g) as a solid.

MS: APCI(+ve) 535 (M+H)⁺.

¹H NMR δ(DMSO-d₆) 8.52 (d, 1H), 8.35 (d, 1H), 8.05 (d, 1H), 7.71-7.63 (m, 2H), 7.56 (dd, 1H), 7.38 (s, 1H), 4.86 (t, 1H), 4.15 (d, 1H), 3.92 (q, 2H), 3.12 (d, 2H), 3.02 (d, 1H), 2.93-2.80 (m, 1H), 2.79-2.59 (m, 2H), 2.59-2.44 (m, 2H), 2.40-2.31 (m, 2H), 2.27 (d, 3H), 2.04-1.89 (m, 1H), 1.09-1.05 (m, 3H), 0.87 (s, 6H), 0.74-0.65 (m, 2H), 0.60-0.52 (m, 2H).

EXAMPLE 27

N-Cyclopropyl-3-fluoro-5-[2-{[1-(hydroxymethyl)cyclobutyl]methyl}-1-oxo-4-(piperazin-1-ylmethyl)-1,2-dihydroisoquinolin-6-yl]-4-methylbenzamide

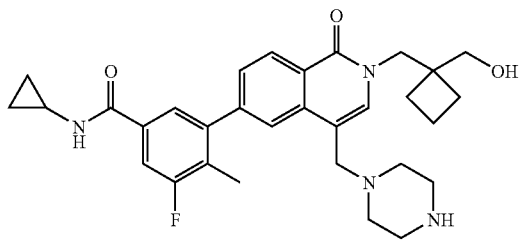

a) tert-Butyl 4-{[6-bromo-1-oxo-2-(phenylsulfonyl)-1,2-dihydroisoquinolin-4-yl]methyl}piperazine-1-carboxylate The subtitle compound was made from 6-bromo-4-(bromomethyl)-2-(phenylsulfonyl)isoquinolin-1(2H)-one (Example 11d) and tert-butyl piperazine-1-carboxylate using the method of Example 11d.

MS: APCI(+ve) 563 (M+H)⁺.

¹H NMR δ (CDCl₃) 8.15-8.11 (m, 4H), 7.87-7.86 (m, 1H), 7.71-7.66 (m, 1H), 7.60-7.55 (m, 3H), 3.53 (s, 2H), 3.48-3.42 (m, 4H), 2.50-2.43 (m, 4H), 1.47 (s, 9H).

b) tert-Butyl 4-[(6-bromo-1-oxo-1,2-dihydroisoquinolin-4-yl)methyl]piperazine-1-carboxylate To a solution of tert-butyl 4-{[6-bromo-1-oxo-2-(phenylsulfonyl)-1,2-dihydroisoquinolin-4-yl]methyl}piperazine-1-carboxylate (Example 27a, 1.35 g) in THF (10 mL) was added sodium hydroxide (0.29 g) in water (5 mL). The reaction was stirred at room temperature for 2 h. The reaction was then heated to 50° C. for 2 h. The volatiles were removed under reduced pressure, and the residue partitioned between ethyl acetate (100 mL) and water (100 mL). The aqueous was extracted further with ethyl acetate (2×100 mL), and the combined organics dried (MgSO₄), filtered, and concentrated under reduced pressure. The residue was triturated with ethyl acetate to afford the subtitle compound as a white solid (0.29 g).

¹H NMR δ (DMSO) 11.36 (d, 1H), 8.13-8.09 (m, 2H), 7.65 (dd, 1H), 7.15-7.12 (m, 1H), 3.49 (s, 2H), 3.30-3.25 (m, 4H), 2.35 (t, 4H), 1.39 (s, 9H).

c) tert-Butyl 4-[(6-bromo-2-{[1-({[tert-butyl(dimethyl)silyl]oxy}methyl)cyclobutyl]methyl}-1-oxo-1,2-dihydroisoquinolin-4-yl)methyl]piperazine-1-carboxylate A solution of tert-butyl 4-[(6-bromo-1-oxo-1,2-dihydroisoquinolin-4-yl)methyl]piperazine-1-carboxylate (Example 27b, 0.171 g) dissolved in DMF (5 mL) was treated with cesium carbonate (0.264 g) and [1-({[tert-butyl(dimethyl)silyl]oxy}methyl)cyclobutyl]methyl methanesulfonate [Archiv der Pharmazie (Weinheim, Germany), 2005, 338 (11), 522-7] (0.187 g) under nitrogen. The resulting mixture was stirred at 70° C. for 7 h. The reaction was diluted with water (300 mL), and extracted with diethyl ether (300 mL×3). The organic was dried (MgSO₄), filtered and evaporated to afford crude product. The crude product was purified (SiO₂ chromatography, elution with 6-12% ethyl acetate/isohexane) to afford the subtitle compound (0.153 g).

¹H NMR δ(CDCl₃) 8.18 (d, 1H), 8.02 (d, 1H), 7.45 (dd, 1H), 7.06 (s, 1H), 4.04 (s, 2H), 3.46 (s, 2H), 3.35-3.29 (m, 6H), 2.33-2.26 (m, 4H), 2.00-1.91 (m, 2H), 1.91-1.68 (m, 2H), 1.63-1.54 (m, 2H), 1.36 (s, 9H), 0.85 (s, 9H), 0.00 (s, 6H).

d) tert-Butyl 4-[(2-{[1-({[tert-butyl(dimethyl)silyl]oxy}methyl)cyclobutyl]methyl}-6-[5-(cyclopropylcarbamoyl)-3-fluoro-2-methylphenyl]-1-oxo-1,2-dihydroisoquinolin-4-yl)methyl]piperazine-1-carboxylate A solution of tert-butyl 4-[(6-bromo-2-{[1-({[tert-butyl(dimethyl)silyl]oxy}methyl)cyclobutyl]methyl}-1-oxo-1,2-dihydroisoquinolin-4-yl)methyl]piperazine-1-carboxylate (Example 27c, 0.153 g) in DMF (4 mL) was treated with N-cyclopropyl-3-fluoro-4-methyl-5-(4,4,5,5-tetramethyl-1,3,2-dioxaborolan-2-yl)benzamide (0.077 g), Pd-118 (4.71 mg) and potassium carbonate (0.067 g) under nitrogen. The resulting mixture was stirred at 75° C. for 8 h. The reaction was partitioned between ethyl acetate and water. The aqueous was extracted with ethyl acetate (2×100 mL) before washing the organics with water (3×100 mL) and brine (3×100 mL). The organic was dried (MgSO₄), filtered, and evaporated under reduced pressure to afford the crude product. The crude product was purified (SiO₂ chromatography, elution with 30% ethyl acetate/isohexane) to afford the subtitle compound (0.099 g) as an oil.

MS: APCI(+ve) 747 (M+H)⁺.

¹H NMR δ (CDCl₃) 8.51 (d, 1H), 7.88 (d, 1H), 7.49 (dd, 1H), 7.43-7.40 (m, 2H), 7.20-7.18 (m, 1H), 4.19 (s, 2H), 3.59 (s, 2H), 3.47 (s, 2H), 3.39-3.34 (m, 4H), 2.94-2.83 (m, 1H), 2.42-2.36 (m, 4H), 2.25 (d, 3H), 2.13-2.02 (m, 2H), 2.03-1.81 (m, 2H), 1.75-1.67 (m, 2H), 1.46 (s, 9H), 0.95 (s, 9H), 0.91-0.84 (m, 2H), 0.63-0.58 (m, 2H), 0.11 (s, 6H).

e) N-Cyclopropyl-3-fluoro-5-[2-{[1-(hydroxymethyl)cyclobutyl]methyl}-1-oxo-4-(piperazin-1-ylmethyl)-1,2-dihydroisoquinolin-6-yl]-4-methylbenzamide Trifluoroacetic Acid (3 mL, 38.94 mmol) was added to a solution of tert-butyl 4-[(2-{[1-({[tert-butyl(dimethyl)silyl]oxy}methyl)cyclobutyl]methyl}-6-[5-(cyclopropylcarbamoyl)-3-fluoro-2-methylphenyl]-1-oxo-1,2-dihydroisoquinolin-4-yl)methyl]piperazine-1-carboxylate (Example 27d 0.099 g) in DCM (9 mL) at room temperature. The reaction was stirred for 30 min before azeotroping with toluene (3×10 mL). The residue was passed through SCX resin, eluting with methanol to remove impurities, and then ~0.7 N methanolic ammonia to elute product, which was then purified by preparative HPLC (Sunfire column using a 95-30% gradient of 0.3% aqueous ammonia in acetonitrile as eluent). The solvents were removed and the residue triturated with diethyl ether to leave the title compound (0.022 g) as a white solid.

MS: APCI(+ve) 533 (M+H)⁺.

¹H NMR δ (CD₃OD) 8.42 (d, 1H), 8.01 (s, 1H), 7.62 (s, 1H), 7.55 (t, 2H), 7.40 (s, 1H), 4.20 (s, 2H), 3.57 (s, 2H), 3.47 (s, 2H), 2.87-2.80 (m, 1H), 2.80-2.73 (m, 4H), 2.50-2.41 (m, 4H), 2.26 (s, 3H), 2.12-2.01 (m, 2H), 1.99-1.88 (m, 2H), 1.83-1.73 (m, 2H), 0.82-0.75 (m, 2H), 0.64-0.58 (m, 2H).

EXAMPLE 28

N-Cyclopropyl-3-fluoro-5-[2-(3-hydroxy-2,2-dimethylpropyl)-4-{[(2S)-2-methylpiperazin-1-yl]methyl}-1-oxo-1,2-dihydroisoquinolin-6-yl]-4-methylbenzamide

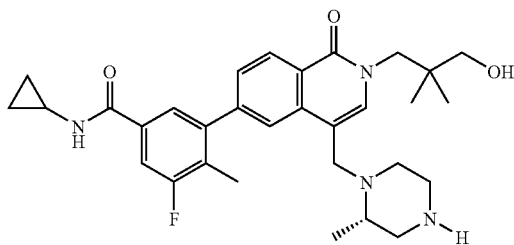

The title compound was synthesised by a similar method to Example 26 h using 3-[2-(3-{[tert-butyl(dimethyl)silyl]oxy}-2,2-dimethylpropyl)-4-(hydroxymethyl)-1-oxo-1,2-dihydroisoquinolin-6-yl]-N-cyclopropyl-5-fluoro-4-methylbenzamide (0.54 g), and tert-butyl (3S)-3-methylpiperazine-1-carboxylate (0.191 g). Purified by preparative HPLC (Waters Xbridge column using a 95-5% gradient of aqueous 0.2% ammonia in acetonitrile as eluent) to give the title compound (0.072 g) as a solid.

MS: APCI(+ve) 535 (M+H)⁺.

¹H NMR δ(DMSO-d₆) 8.54 (d, 1H), 8.35 (d, 1H), 8.05 (s, 1H), 7.72-7.54 (m, 2H), 7.39 (s, 1H), 4.88 (s, 1H), 4.22-3.76 (m, 4H), 3.24-2.59 (m, 6H), 2.40-2.30 (m, 2H), 2.27 (s, 3H), 2.05-1.91 (m, 1H), 1.15-1.01 (m, 6H), 0.88 (s, 6H), 0.73-0.65 (m, 2H), 0.59-0.53 (m, 2H).

EXAMPLE 29

N-Cyclopropyl-3-fluoro-5-[2-(3-hydroxy-2,2-dimethylpropyl)-4-{[(3S)-3-methylpiperazin-1-yl]methyl}-1-oxo-1,2-dihydroisoquinolin-6-yl]-4-methylbenzamide hydrochloride

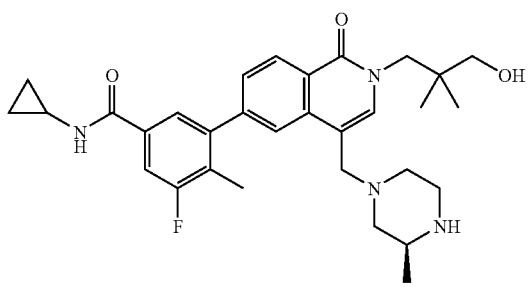

The subtitle product was made from 3-[2-(3-{[tert-butyl(dimethyl)silyl]oxy}-2,2-dimethylpropyl)-4-(hydroxymethyl)-1-oxo-1,2-dihydroisoquinolin-6-yl]-N-cyclopropyl-5-fluoro-4-methylbenzamide (Example 26 g, 190 mg) by sequential reaction with methanesulfonyl chloride (57 μL) and tert-butyl (2S)-2-methylpiperazine-1-carboxylate (240 mg) using a similar method to Example 26 h, to afford the title compound (58 mg) as a white solid.

MS: APCI(+ve) 535 (M+H)⁺.

¹H NMR δ(DMSO-d₆) 8.61 (s, 1H), 8.37 (d, 1H), 8.09-7.78 (m, 2H), 7.67 (d, 1H), 7.59 (d, 1H), 3.97 (d, 2H), 3.88-3.42 (m, 8H), 3.17 (s, 2H), 2.92-2.85 (m, 2H), 2.22 (d, 3H), 1.25 (d, 3H), 0.89 (s, 6H), 0.73-0.59 (m, 4H).

EXAMPLE 30

3-[4-{[(3R)-3-Aminopiperidin-1-yl]methyl}-2-(3-hydroxy-2,2-dimethylpropyl)-1-oxo-1,2-dihydroisoquinolin-6-yl]-N-cyclopropyl-5-fluoro-4-methylbenzamide

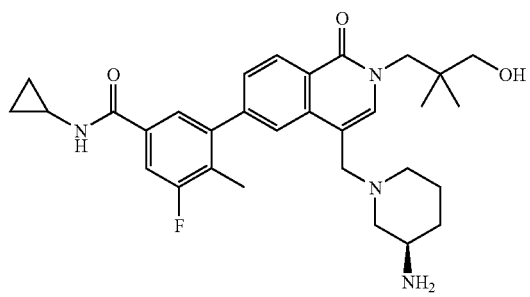

A solution of 3-[2-(3-{[tert-butyl(dimethyl)silyl]oxy}-2,2-dimethylpropyl)-4-(hydroxymethyl)-1-oxo-1,2-dihydroisoquinolin-6-yl]-N-cyclopropyl-5-fluoro-4-methylbenzamide (Example 26 g, 390 mg) and triethylamine (0.192 mL) in DCM (15 mL) was treated with methanesulfonyl chloride (0.059 mL) at 0° C. under nitrogen. After 30 min, water (15 mL) was added and the mixture was stirred vigorously and warmed to room temperature. The layers were separated and the organic layer was dried by passage through a plug of solid Na₂SO₄ and evaporated. The residue was dissolved in acetonitrile (5 mL) and aliquots of this were used directly without further purification to prepare examples 30 and 31.

tert-Butyl (3R)-piperidin-3-ylcarbamate (200 mg) was treated with the above stock solution (2 mL) at room temperature under nitrogen. The mixture was stirred for 18 h and then evaporated. The residue was dissolved in DCM (3 mL) and treated with 4 M hydrochloric acid in dioxane (1.9 mL). Methanol (3 mL) was added to give a solution. After 10 min the solution was evaporated and the residue partitioned between saturated aqueous NaHCO₃ (20 mL) and DCM (30 mL). The layers were separated and the aqueous washed with DCM (2×30 mL). The combined organics were dried (Na₂SO₄), filtered and evaporated and the crude product was purified (SiO₂ chromatography, elution with 0-7% 7 N NH₃/methanol in DCM) to afford the title compound (63 mg) as a white solid.

MS: APCI(+ve) 535 (M+H)⁺.

¹H NMR δ (CDCl₃) 8.51 (d, 1H), 7.90 (d, 1H), 7.56-7.52 (m, 1H), 7.48-7.44 (m, 2H), 7.00 (s, 1H), 6.75 (s, 1H), 3.91 (s, 2H), 3.57 (d, 1H), 3.44 (d, 1H), 3.13 (s, 2H), 2.93-2.86 (m, 2H), 2.74-2.67 (m, 1H), 2.57-2.44 (m, 1H), 2.24 (d, 3H), 2.32-2.06 (m, 1H), 1.83-1.19 (m, 5H), 1.03 (s, 3H), 1.01 (s, 3H), 0.90-0.83 (m, 2H), 0.64-0.59 (m, 2H).

EXAMPLE 31

3-{4-[(4-Amino-4-methylpiperidin-1-yl)methyl]-2-(3-hydroxy-2,2-dimethylpropyl)-1-oxo-1,2-dihydroisoquinolin-6-yl}-N-cyclopropyl-5-fluoro-4-methylbenzamide

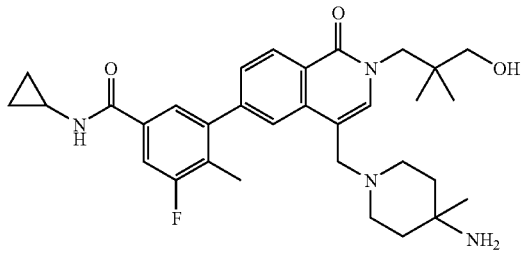

tert-Butyl (4-methylpiperidin-4-yl)carbamate (107 mg) was treated with was treated with an aliquot (2 mL) of the stock solution described in Example 30 at room temperature under nitrogen. The mixture was stirred for 18 h and then evaporated. The residue (240 mg) was dissolved in DCM (3 mL) and was treated with 4 M hydrochloric acid in dioxane (1.9 mL). Methanol (3 mL) was added to give a solution. After 10 min the solution was evaporated and the residue partitioned between saturated aqueous NaHCO₃ (20 mL) and DCM (30 mL). The layers were separated and the aqueous washed with DCM (2×30 mL). The combined organics were dried (Na₂SO₄), filtered and evaporated to give crude product. The crude product was purified (SiO₂ chromatography, elution with 0-7% 7 N NH₃/MeOH in DCM) to afford the title compound (86 mg) as a white solid.

MS: APCI(+ve) 550 (M+H)⁺.

¹H NMR δ (CDCl₃) 8.52 (d, 1H), 7.91 (d, 1H), 7.50-7.44 (m, 3H), 7.02 (s, 1H), 6.23 (s, 1H), 4.83 (s, 1H), 3.90 (s, 2H), 3.54 (s, 2H), 3.12 (s, 2H), 2.90 (octet, 1H), 2.52-2.39 (m, 4H), 2.25 (d, 3H), 1.65-1.39 (m, 4H), 1.13 (s, 3H), 1.02 (s, 6H), 0.91-0.85 (m, 2H), 0.64-0.59 (m, 2H).

EXAMPLE 32

N-Cyclopropyl-3-fluoro-5-[2-(3-hydroxy-2,2-dimethylpropyl)-4-{[4-(3-hydroxypropyl)piperazin-1-yl]methyl}-1-oxo-1,2-dihydroisoquinolin-6-yl]-4-methylbenzamide

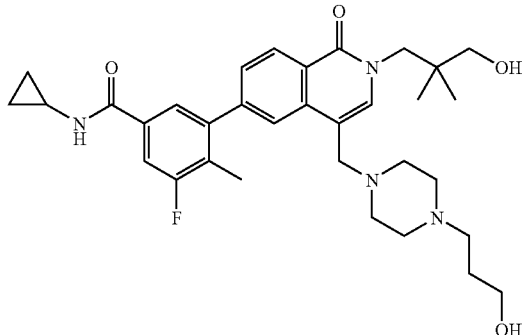

a) 6-Bromo-2-(3-{[tert-butyl(dimethyl)silyl]oxy}-2,2-dimethylpropyl)-4-{[4-(3-hydroxypropyl)piperazin-1-yl]methyl}isoquinolin-1(2H)-one 6-Bromo-4-(bromomethyl)-2-(phenylsulfonyl)isoquinolin-1(2H)-one (Example 11d, 1.0 g), 3-piperazin-1-ylpropan-1-ol (0.315 g) and triethylamine (0.305 mL) were stirred together in THF (20 mL) at room temperature for 3 h, 2 M NaOH (3 mL) was added and the reaction mixture stirred at room temperature for 16 h, acidified (2 M HCl) and extracted into ethyl acetate, the aqueous layer was basified (saturated aqueous NaHCO₃) and extracted into ethyl acetate (3×20 mL) combined organics were dried (MgSO₄) filtered and evaporated. The residue was dissolved in DMF (10 mL), treated with cesium carbonate (0.49 g) and (3-bromo-2,2-dimethylpropoxy)(tert-butyl)dimethylsilane (0.269 g). The resulting mixture was stirred at 80° C. under nitrogen for 72 h, cooled, diluted with saturated brine (30 mL) and extracted into ethyl acetate (3×30 mL), the combined extracts were washed with brine (3×30 mL), dried (MgSO₄) filtered and evaporated to give the subtitle compound (0.3 g).

MS: APCI(+ve) 580/581 (M+H)⁺.

¹H NMR δ(DMSO-d₆) 8.14 (d, 1H), 8.12 (d, 1H), 7.65 (dd, 1H), 7.26 (s, 1H), 3.88 (s, 2H), 3.47-3.34 (m, 8H), 2.43-2.25 (m, 6H), 1.60-1.49 (m, 2H), 0.93 (s, 3H), 0.91 (s, 3H), 0.88 (s, 9H), 0.85 (s, 2H), 0.05 (s, 6H).

b) N-Cyclopropyl-3-fluoro-5-[2-(3-hydroxy-2,2-dimethylpropyl)-4-{[4-(3-hydroxypropyl)piperazin-1-yl]methyl}-1-oxo-1,2-dihydroisoquinolin-6-yl]-4-methylbenzamide A solution of 6-bromo-2-(3-{[tert-butyl(dimethyl)silyl]oxy}-2,2-dimethylpropyl)-4-{[4-(3-hydroxypropyl)piperazin-1-yl]methyl}isoquinolin-1(2H)-one (Example 32a, 1.0 g), N-cyclopropyl-3-fluoro-4-methyl-5-(4,4,5,5-tetramethyl-1,3,2-dioxaborolan-2-yl)benzamide (0.165 g), potassium carbonate (0.143 g) and Pd-118 (0.034 g) was stirred in DMF (10 mL) at 80° C. under nitrogen for 2 h. The reaction was cooled, diluted with saturated brine and extracted into ethyl acetate (3×30 mL), the combined extracts were washed with brine (3×30 mL), dried, (MgSO₄) filtered and evaporated. The residue was dissolved in DCM (20 mL), treated with trifluoroacetic acid (3 mL) and stirred at room temperature for 3 h, evaporated and purified by preparative HPLC (Waters Xbridge column using a 95-5% gradient of aqueous 0.2% ammonia in acetonitrile as eluent) to give the title compound (0.052 g) as a solid.

MS: APCI(+ve) 579 (M+H)⁺.

¹H NMR δ(DMSO-d₆) 8.54 (d, 1H), 8.35 (d, 1H), 7.96 (d, 1H), 7.68-7.64 (m, 2H), 7.56 (dd, 1H), 7.37 (s, 1H), 4.98-4.79 (m, 1H), 4.53-4.38 (m, 1H), 3.92 (s, 2H), 3.51 (s, 2H), 3.42 (t, 2H), 3.12 (s, 2H), 2.92-2.79 (m, 1H), 2.48-2.35 (m, 7H), 2.30 (t, 2H), 2.26 (d, 3H), 1.59-1.50 (m, 2H), 0.88 (s, 6H), 0.73-0.67 (m, 2H), 0.60-0.54 (m, 2H).

EXAMPLE 33

N-Cyclopropyl-3-fluoro-5-(2-{[1-(hydroxymethyl)cyclopropyl]methyl}-4-{[(2R)-2-methylpiperazin-1-yl]methyl}-1-oxo-1,2-dihydroisoquinolin-6-yl)-4-methylbenzamide

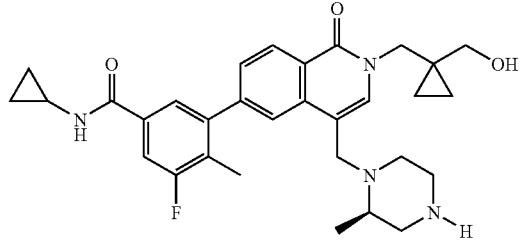

a) tert-Butyl (3R)-4-[(6-bromo-1-oxo-1,2-dihydroisoquinolin-4-yl)methyl]-3-methylpiperazine-1-carboxylate 6-Bromo-4-(bromomethyl)-2-(phenylsulfonyl)isoquinolin-1(2H)-one (Example 11d, 2.0 g), tert-butyl (3R)-3-methylpiperazine-1-carboxylate (0.946 g) and N,N-diisopropylethylamine (1.143 mL) were dissolved in THF (10 mL) and stirred at room temperature under nitrogen for 16 h. The reaction mixture was diluted with methanol (10 mL) and treated with sodium hydroxide (0.35 g), after stirring at room temperature for 1 h, water (200 mL) was added and the reaction mixture extracted into ethyl acetate (250 mL). The separated organic layer was dried (MgSO₄) filtered and evaporated, the residue was purified (SiO₂ chromatography, elution with ethyl acetate) to give the subtitle compound (0.75 g) as a solid.

$^1$H NMR δ(DMSO-d$_6$) 11.35 (d, 1H), 8.16 (s, 1H), 8.11 (dd, 1H), 7.67-7.62 (m, 1H), 7.16 (d, 1H), 4.01 (d, 1H), 3.50 (d, 1H), 3.45-2.97 (m, 5H), 2.25-1.97 (m, 2H), 1.39 (s, 9H), 1.14 (d, 3H).

b) N-Cyclopropyl-3-fluoro-5-(2-{[1-(hydroxymethyl)cyclopropyl]methyl}-4-{[(2R)-2-methylpiperazin-1-yl]methyl}-1-oxo-1,2-dihydroisoquinolin-6-yl)-4-methylbenzamide tert-Butyl (3R)-4-[(6-bromo-1-oxo-1,2-dihydroisoquinolin-4-yl)methyl]-3-methylpiperazine-1-carboxylate (Example 33a, 0.75 g), [1-({[tert-butyl(dimethyl)silyl]oxy}methyl)cyclopropyl]methyl methanesulfonate (0.56 g) and cesium carbonate (1.68 g) were stirred together in DMF (15 mL) at 80° C. for 2 h under nitrogen, cooled, diluted with water (100 mL) and extracted into ethyl acetate (3×20 mL), and the combined organics washed with saturated brine (3×20 mL), dried (MgSO$_4$) filtered and evaporated. The residue was dissolved in DMF (10 mL), treated with N-cyclopropyl-3-fluoro-4-methyl-5-(4,4,5,5-tetramethyl-1,3,2-dioxaborolan-2-yl)benzamide (0.165 g), potassium carbonate (0.143 g) and Pd-118 (0.034 g) and the resulting mixture was stirred together at 80° C. under nitrogen for 2 h, cooled, diluted with saturated brine and extracted into ethyl acetate (3×30 mL), and the combined extracts were washed with brine (3×30 mL), dried (MgSO$_4$) filtered, and evaporated. The residue was dissolved in DCM (20 mL), treated with trifluoroacetic acid (3 mL), stirred at room temperature for 3 h, evaporated and purified by preparative HPLC (Waters Xbridge column using a 95-5% gradient of aqueous 0.2% ammonia in acetonitrile as eluent) to give the title compound (0.057 g) as a solid.

MS: APCI(+ve) 533 (M+H)$^+$.

$^1$H NMR δ(DMSO-d$_6$) 8.53 (d, 1H), 8.35 (d, 1H), 8.04 (s, 1H), 7.71-7.53 (m, 3H), 7.45 (s, 1H), 4.70 (t, 1H), 4.15 (d, 1H), 4.04 (s, 2H), 3.26-3.13 (m, 4H), 3.04 (d, 1H), 2.91-2.59 (m, 2H), 2.39-2.30 (m, 2H), 2.26 (s, 3H), 2.08-1.93 (m, 2H), 1.07 (d, 3H), 0.90-0.79 (m, 1H), 0.76-0.62 (m, 4H), 0.59-0.53 (m, 2H), 0.46-0.38 (m, 2H).

EXAMPLE 34

N-Cyclopropyl-3-fluoro-5-(2-{[1-(hydroxymethyl)cyclopropyl]methyl}-4-{[(3S)-3-methylpiperazin-1-yl]methyl}-1-oxo-1,2-dihydroisoquinolin-6-yl)-4-methylbenzamide

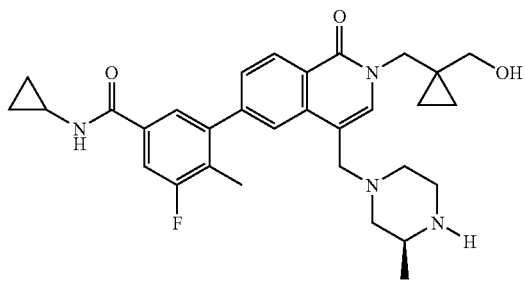

a) tert-Butyl (2S)-4-{[6-bromo-1-oxo-2-(phenylsulfonyl)-1,2-dihydroisoquinolin-4-yl]methyl}-2-methylpiperazine-1-carboxylate The subtitle compound was prepared by the method of Example 11e using (S)-tert-butyl 2-methylpiperazine-1-carboxylate and 6-bromo-4-(bromomethyl)-2-(phenylsulfonyl)isoquinolin-1(2H)-one (Example 11d)

$^1$H NMR δ(CDCl$_3$) 10.03-9.90 (m, 1H), 8.37 (s, 1H), 7.68-7.48 (m, 2H), 7.08-7.00 (m, 1H), 4.28-4.19 (m, 1H), 3.80 (d, 1H), 3.60-3.36 (m, 2H), 3.11-2.97 (m, 1H), 2.86-2.62 (m, 2H), 2.30-2.18 (m, 1H), 2.03-1.91 (m, 1H), 1.51 (s, 9H), 1.21 (d, 3H).

b) tert-Butyl (2S)-4-[(6-bromo-1-oxo-1,2-dihydroisoquinolin-4-yl)methyl]-2-methylpiperazine-1-carboxylate A solution of tert-butyl (2S)-4-{[6-bromo-1-oxo-2-(phenylsulfonyl)-1,2-dihydroisoquinolin-4-yl]methyl}-2-methylpiperazine-1-carboxylate (Example 34a, 3.2 g) dissolved in DMF (20 mL) was treated with sodium hydroxide (0.444 g) in water (20 mL) under nitrogen. The resulting mixture was stirred at 20° C. for 2 h. The reaction mixture was diluted with water (20 mL), and extracted with ethyl acetate (25 mL). The organics were dried (MgSO$_4$), filtered and evaporated to afford crude product. The crude product was purified (SiO$_2$ chromatography, elution 100% diethyl ether). Pure fractions were evaporated to dryness to afford the subtitle compound (0.780 g) as a solid.

MS: APCI(+ve) 438 (M+H)$^+$.

c) [1-({[tert-Butyl(dimethyl)silyl]oxy}methyl)cyclopropyl]methanol

A solution of cyclopropane-1,1-diyldimethanol (3.7 g) dissolved in ethylene glycol dimethyl ether (50 mL) was treated with 60% sodium hydride (1.449 g) at 0° C. under nitrogen. The resulting mixture was stirred at 20° C. for 1 h, treated with tert-butylchlorodimethylsilane (5.46 g) and stirred at room temperature overnight. The reaction mixture was diluted with water (250 mL), and extracted with ethyl acetate (2×250 mL). The organic was dried (MgSO$_4$), filtered and evaporated to afford crude product. The crude product was purified (SiO$_2$ chromatography, elution 100% DCM). Pure fractions were evaporated to dryness to afford the subtitle compound (5.50 g) as an oil.

$^1$H NMR δ(CDCl$_3$) 3.65-3.51 (m, 4H), 2.79-2.65 (m, 1H), 0.96-0.82 (m, 9H), 0.54-0.40 (m, 4H), 0.14-0.03 (m, 6H).

d) [1-({[tert-Butyl(dimethyl)silyl]oxy}methyl)cyclopropyl]methyl methanesulfonate A solution of [1-({[tert-butyl(dimethyl)silyl]oxy}methyl)cyclopropyl]methanol (Example 34c, 5.37 g) dissolved in DCM (20 mL) was treated with triethylamine (6.92 mL) at 0° C. before adding methanesulfonyl chloride (2.321 mL) under nitrogen. The resulting mixture was stirred at 0° C. for 30 min. The reaction mixture was diluted with water (100 mL), and extracted with DCM (250 mL). The organics were dried (MgSO$_4$), filtered and evaporated. The crude product was purified (SiO$_2$ chromatography, elution 50% isohexane in diethyl ether). Pure fractions were evaporated to dryness to afford the subtitle compound (5.37 g) as an oil.

$^1$H NMR δ(CDCl$_3$) 4.18-4.10 (m, 2H), 3.74 (s, 3H), 3.21 (s, 3H), 2.86-2.73 (m, 3H), 1.76-1.63 (m, 4H), 1.43 (s, 9H).

e) N-Cyclopropyl-3-fluoro-5-(2-{[1-(hydroxymethyl)cyclopropyl]methyl}-4-{[(3S)-3-methylpiperazin-1-yl]methyl}-1-oxo-1,2-dihydroisoquinolin-6-yl)-4-methylbenzamide A solution of tert-butyl (2S)-4-[(6-bromo-1-oxo-1,2-dihydroisoquinolin-4-yl)methyl]-2-methylpiperazine-1-carboxylate (Example 34b, 0.26 g) dissolved in DMF (5 mL) was treated with [1-({[tert-butyl(dimethyl)silyl]oxy}methyl)cyclopropyl]methyl methanesulfonate (example 34d, 0.351 g) and cesium carbonate (0.582 g) under nitrogen. The resulting mixture was stirred at 75° C. for 3 h. The mixture was treated with N-cyclopropyl-3-fluoro-4-methyl-5-(4,4,5,5-tetramethyl-1,3,2-dioxaborolan-2-yl)benzamide (0.266 g) and Pd-118 (0.019 g) before heating at 80° C. for 1 h. The reaction mixture was diluted with water (250 mL), and extracted with ethyl acetate (250 mL). The organic was dried (MgSO$_4$), filtered and evaporated. The crude product was purified (SiO$_2$ chromatography, elution 100% ethyl acetate). Pure fractions of [tert-butyl (2S)-4-[(6-[5-(cyclopropylcarbamoyl)-3-fluoro-2-methylphenyl]-2-{[1-(hydroxymethyl)cyclopropyl]methyl}-1-oxo-1,2-dihydroisoquinolin-4-yl)methyl]-2-methylpiperazine-1-carboxylate] were evaporated to dryness. The mixture was treated with trifluoroacetic acid/DCM (1:1, 10 mL) and stirred for 1 h at room temperature. The mixture was evaporated to dryness and the crude material was dissolved in acetonitrile (25 mL) and loaded on to a 10 g SCX cartridge. The impurities were washed through with acetonitrile (50 mL) and discarded. The product was eluted with 1 N methanolic ammonia (100 mL) and evaporated in vacuo. The product was purified by preparative HPLC (XBridge column using a 95-40% gradient of aqueous 0.1% ammonia in acetonitrile as eluent). The fractions were evaporated to afford the title compound (0.050 g).

MS: APCI(+ve) 533 (M+H)$^+$.

$^1$H NMR δ (DMSO-d$_6$) 8.11 (d, 1H), 7.93 (d, 1H), 7.56 (s, 1H), 7.27-7.22 (m, 2H), 7.13 (d, 1H), 7.03 (s, 1H), 4.32-4.25 (m, 1H), 3.67-3.58 (m, 2H), 3.10-3.00 (m, 2H), 2.83-2.76 (m, 2H), 2.48-2.12 (m, 5H), 1.85 (s, 3H), 1.52-1.43 (m, 2H), 1.14 (t, 1H), 0.47 (d, 3H), 0.31-0.24 (m, 4H), 0.18-0.11 (m, 2H), 0.05-0.02 (m, 2H).

The following Examples 35 to 37 (Table 3) were prepared using 6-bromo-4-(bromomethyl)-2-(phenylsulfonyl)isoquinolin-1(2H)-one (Example 11d), a suitable amine (for Y), followed by a suitable alkylating agent (for R1) using a similar method to that described in Example 34.

EXAMPLE 35

N-Cyclopropyl-3-fluoro-5-(2-[3-hydroxy-2-(hydroxymethyl)propyl]-4-{[(3S)-3-methylpiperazin-1-yl]methyl}-1-oxo-1,2-dihydroisoquinolin-6-yl)-4-methylbenzamide

EXAMPLE 36

N-Cyclopropyl-3-fluoro-5-(2-[3-hydroxy-2-(hydroxymethyl)-2-methylpropyl]-4-{[(3S)-3-methylpiperazin-1-yl]methyl}-1-oxo-1,2-dihydroisoquinolin-6-yl)-4-methylbenzamide

EXAMPLE 37

N-Cyclopropyl-3-fluoro-5-(2-[2-(hydroxymethyl)-2-methylbutyl]-4-{[(3S)-3-methylpiperazin-1-yl]methyl}-1-oxo-1,2-dihydroisoquinolin-6-yl)-4-methylbenzamide

TABLE 3

| Example | R1 | Y | MS [M + H]$^+$ m/z | $^1$H NMR δ (DMSO-d$_6$) unless indicated |
|---|---|---|---|---|
| 35 | CH$_2$CH(CH$_2$OH)$_2$ | (3S)-3-methylpiperazin-1-yl | 537 | 8.57(s, 1H), 8.34(d, 1H), 8.00 (s, 1H), 7.70-7.62(m, 2H), 7.54 (d, 1H), 7.42(s, 1H), 4.58-4.51 (m, 2H), 4.04-3.91(m, 2H), 3.49-3.39(m, 6H), 2.89-2.53(m, 5H), 2.21(s, 3H), 2.09-1.99(m, 1H), 1.92-1.83(m, 2H), 1.55(t, 1H), 0.88(d, 3H), 0.74-0.65(m, 2H), 0.61-0.52(m, 2H) |
| 36 | CH$_2$C(CH$_3$)(CH$_2$OH)$_2$ | (3S)-3-methylpiperazin-1-yl | 551 | 8.56-8.49(m, 1H), 8.37(d, 1H), 7.98(s, 1H), 7.71-7.63(m, 2H), 7.57(d, 1H), 7.44(s, 1H), 4.78-4.69(m, 2H), 4.00-3.91(m, 2H), 3.56-3.47(m, 2H), 3.29-3.15 (m, 5H), 3.01-2.66(m, 5H), 2.28 (s, 3H), 0.99(d, 3H), 0.86-0.80 (m, 6H), 0.73-0.66(m, 2H), 0.60-0.53(m, 2H) |

TABLE 3-continued

| Example | R1 | Y | MS [M + H]+ m/z | 1H NMR δ (DMSO-d6) unless indicated |
|---|---|---|---|---|
| 37 | (2,2-dimethyl-3-hydroxypropyl) | (piperazin-1-yl) | 535 | 8.56-8.49(m, 1H), 8.35(d, 1H), 7.98(s, 1H), 7.69-7.64(m, 2H), 7.56(d, 1H), 7.40(s, 1H), 4.83(t, 1H), 3.96-3.88(m, 2H), 3.50(s, 2H), 3.15(s, 2H), 2.90-2.82(m, 1H), 2.69-2.62(m, 4H), 2.38-2.30(m, 4H), 2.28(s, 3H), 1.40-1.20(m, 2H), 0.87(t, 3H), 0.79 (s, 3H), 0.72-0.66(m, 2H), 0.59-0.54(m, 2H) |

EXAMPLE 38

N-Cyclopropyl-3-fluoro-5-[2-(3-hydroxy-2,2-dimethylpropyl)-1-oxo-4-(1-piperazin-1-ylethyl)-1,2-dihydroisoquinolin-6-yl]-4-methylbenzamide racemate

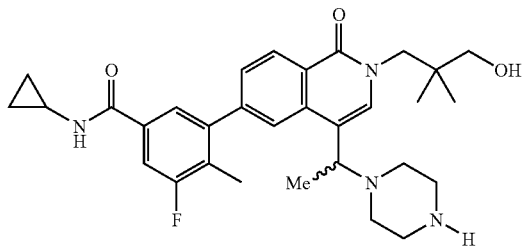

a) 6-Bromo-2-(3-{[tert-butyl(dimethyl)silyl]oxy}-2,2-dimethylpropyl)-4-(1-hydroxyethyl)isoquinolin-1(2H)-one Methylmagnesium chloride (3 M in THF) (0.89 mL) was added dropwise to a solution of 6-bromo-2-(3-hydroxy-2,2-dimethylpropyl)-1-oxo-1,2-dihydroisoquinoline-4-carbaldehyde (Example 26d, 1.10 g) in THF (15 mL) at 0° C. The reaction was removed from the cooling bath and allowed to stir for 1 h. The reaction was quenched with saturated ammonium chloride solution (10 mL) and partitioned between ethyl acetate (30 mL) and water (30 mL). The organics were separated, dried (MgSO4), filtered and evaporated to afford the subtitle product (1.10 g) as a yellow solid.

1H NMR δ(DMSO-d6) 8.12 (d, 1H), 8.06 (d, 1H), 7.59 (dd, 1H), 7.27 (s, 1H), 5.22-5.17 (m, 1H), 4.90 (quintet, 1H), 3.89-3.80 (m, 2H), 3.27 (s, 2H), 1.37 (d, 3H), 0.85 (s, 9H), 0.79 (d, 6H), 0.00 (s, 6H).

b) 6-Bromo-2-(3-{[tert-butyl(dimethyl)silyl]oxy}-2,2-dimethylpropyl)-4-(1-hydroxyethyl)isoquinolin-1(2H)-one Methanesulfonyl chloride (0.22 mL) was added to a solution of 6-bromo-2-(3-{[tert-butyl(dimethyl)silyl]oxy}-2,2-dimethylpropyl)-4-(1-hydroxyethyl)isoquinolin-1(2H)-one (Example 38a, 1.10 g) and triethylamine (0.82 mL) in DCM (15 mL) at 0° C. The solution was stirred for 10 min at 0° C. and then 1 h at room temperature before tert-butyl piperazine-1-carboxylate (0.88 g) was added and the reaction stirred for 3 h before the volatiles were removed under reduced pressure. The crude product was purified (SiO2 chromatography, elution with 10 to 20% ethyl acetate in isohexane) to afford the subtitle product (0.51 g) as a white solid.

1H NMR δ(DMSO-d6) 8.37 (s, 1H), 8.30 (d, 1H), 7.55 (dd, 1H), 7.17 (s, 1H), 3.96 (d, 2H), 3.57 (q, 1H), 3.42-3.34 (m, 4H), 3.30 (s, 2H), 2.58-2.45 (m, 2H), 2.42-2.35 (m, 2H), 1.45 (s, 9H), 1.39 (d, 3H), 0.95 (s, 9H), 0.91 (d, 6H), 0.09 (s, 6H).

c) tert-Butyl 4-(1-{2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}ethyl)piperazine-1-carboxylate 6-Bromo-2-(3-{[tert-butyl(dimethyl)silyl]oxy}-2,2-dimethylpropyl)-4-(1-hydroxyethyl)isoquinolin-1(2H)-one (Example 38b, 0.50 g) was reacted with N-cyclopropyl-3-fluoro-4-methyl-5-(4,4,5,5-tetramethyl-1,3,2-dioxaborolan-2-yl)benzamide (0.301 g) by the method of Example 26e to afford the subtitle compound (0.30 g) as a yellow oil.

1H NMR δ(CDCl3) 8.52 (d, 1H), 8.10 (s, 1H), 7.49 (dd, 1H), 7.39 (d, 2H), 7.22 (s, 1H), 6.21 (s, 1H), 4.01 (s, 2H), 3.61-3.55 (m, 1H), 3.38-3.32 (m, 4H), 2.94-2.86 (m, 1H), 2.55-2.48 (m, 2H), 2.41-2.34 (m, 2H), 2.24 (d, 2H), 1.57 (s, 3H), 1.44 (s, 9H), 1.41 (d, 3H), 0.97 (d, 9H), 0.95 (d, 6H), 0.87 (td, 2H), 0.63-0.58 (m, 2H), 0.10 (t, 6H).

d) N-Cyclopropyl-3-fluoro-5-[2-(3-hydroxy-2,2-dimethylpropyl)-1-oxo-4-(1-piperazin-1-ylethyl)-1,2-dihydroisoquinolin-6-yl]-4-methylbenzamide racemate A solution of tert-butyl 4-(1-{2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}ethyl)piperazine-1-carboxylate (Example 38c, 80 mg) in 4 M HCl in dioxane (1 mL) and ethanol (3 mL) was stirred overnight at room temperature before the volatiles were removed in vacuo. The crude material was dissolved in methanol (2 mL) and loaded onto a 10 g SCX cartridge. The impurities were washed through with methanol (50 mL) and discarded. The product was eluted with 1 N methanolic ammonia (50 mL) and evaporated in vacuo to afford the title product (58 mg).

MS: APCI(+ve) 535 (M+H)$^+$.

$^1$H NMR δ(DMSO-d$_6$) 8.52 (d, 1H), 8.37 (d, 1H), 8.17 (s, 1H), 7.66 (t, 2H), 7.53 (dd, 1H), 7.35 (s, 1H), 4.87 (t, 1H), 4.08 (q, 1H), 3.93 (d, 2H), 3.75 (d, 1H), 3.34-3.28 (m, 2H), 3.17 (d, 2H), 3.11 (d, 2H), 2.89-2.82 (m, 1H), 2.65-2.56 (m, 2H), 2.47-2.38 (m, 2H), 2.24 (d, 3H), 1.32 (d, 3H), 0.87 (s, 6H), 0.72-0.66 (m, 2H), 0.59-0.54 (m, 2H).

EXAMPLE 39 AND EXAMPLE 40

N-Cyclopropyl-3-fluoro-5-[2-(3-hydroxy-2,2-dimethylpropyl)-1-oxo-4-(1-piperazin-1-ylethyl)-1,2-dihydroisoquinolin-6-yl]-4-methylbenzamide—Enantiomer 1 and Enantiomer 2

Enantiomer 1

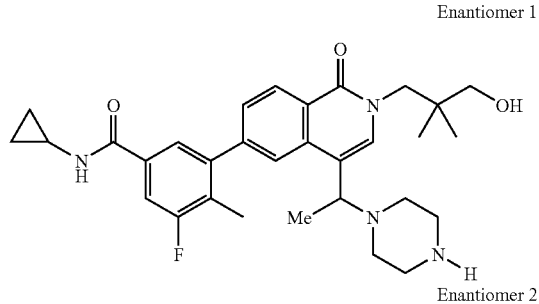

Enantiomer 2

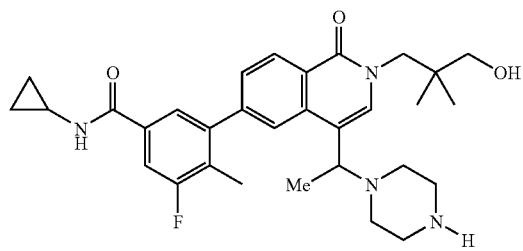

N-Cyclopropyl-3-fluoro-5-[2-(3-hydroxy-2,2-dimethylpropyl)-1-oxo-4-(1-piperazin-1-ylethyl)-1,2-dihydroisoquinolin-6-yl]-4-methylbenzamide racemate (Example 38, 49 mg) was separated by supercritical fluid chromatography (SFC) (250×20 mm Chiralpak IA column at 40° C. using 40% isopropanol in supercritical CO$_2$: 0.1% diethylamine at 50 mL/minute (135 bar) with a 14 minute run time) to afford the separated title compounds enantiomer 1 (10 mg) and enantiomer 2 (10 mg) each as a white solid.

Isomer 1:
MS: APCI(+ve) 535 (M+H)$^+$.
$^1$H NMR δ(DMSO-d$_6$) 8.52 (d, 1H), 8.37 (d, 1H), 8.16 (s, 1H), 7.66 (t, 2H), 7.53 (dd, 1H), 7.35 (s, 1H), 4.88 (t, 1H), 4.11-4.06 (m, 1H), 3.93 (dd, 2H), 3.79-3.73 (m, 1H), 3.14 (dd, 2H), 2.85 (dsextet, 1H), 2.70-2.58 (m, 4H), 2.47-2.30 (m, 4H), 2.24 (d, 3H), 1.32 (d, 3H), 0.87 (s, 6H), 0.69 (td, 2H), 0.59-0.54 (m, 2H).

Isomer 2:
MS: APCI(+ve) 535 (M+H)$^+$.
$^1$H NMR δ(DMSO-d$_6$) 8.52 (d, 1H), 8.37 (d, 1H), 8.16 (s, 1H), 7.66 (t, 2H), 7.53 (dd, 1H), 7.35 (s, 1H), 4.88 (t, 1H), 3.93 (dd, 2H), 3.76 (q, 1H), 3.14 (dd, 2H), 2.85 (dq, 1H), 2.70-2.30 (m, 8H), 2.24 (d, 3H), 1.32 (d, 3H), 0.87 (s, 6H), 0.69 (td, 2H), 0.58-0.54 (m, 2H).

EXAMPLE 41

3-{4-[1-(4-Amino-4-methylpiperidin-1-yl)ethyl]-2-(3-hydroxy-2,2-dimethylpropyl)-1-oxo-1,2-dihydroisoquinolin-6-yl}-N-cyclopropyl-5-fluoro-4-methylbenzamide

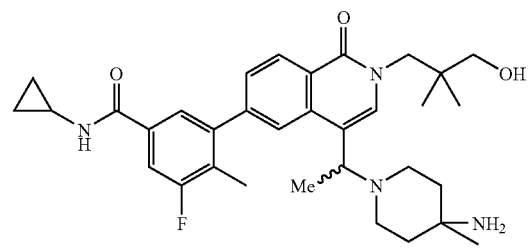

a) 3-[2-(3-{[tert-Butyl(dimethyl)silyl]oxy}-2,2-dimethylpropyl)-4-(1-hydroxyethyl)-1-oxo-1,2-dihydroisoquinolin-6-yl]-N-cyclopropyl-5-fluoro-4-methylbenzamide 3-[2-(3-{[tert-butyl(dimethyl)silyl]oxy}-2,2-dimethylpropyl)-4-formyl-1-oxo-1,2-dihydroisoquinolin-6-yl]-N-cyclopropyl-5-fluoro-4-methylbenzamide (Example 26f, 1.10 g) was reacted with methylmagnesium chloride (3 M in THF) (1.62 mL) by the method of Example 38a to afford the subtitle compound (1.10 g) as a yellow solid.

MS: APCI(+ve) 581 (M+H)$^+$.

b) 3-{4-[1-(4-Amino-4-methylpiperidin-1-yl)ethyl]-2-(3-hydroxy-2,2-dimethylpropyl)-1-oxo-1,2-dihydroisoquinolin-6-yl}-N-cyclopropyl-5-fluoro-4-methylbenzamide Methanesulfonyl chloride (0.18 mL) was added to a solution of 3-[2-(3-{[tert-butyl(dimethyl)silyl]oxy}-2,2-dimethylpropyl)-4-(1-hydroxyethyl)-1-oxo-1,2-dihydroisoquinolin-6-yl]-N-cyclopropyl-5-fluoro-4-methylbenzamide (Example 41a, 1.1 g) and triethylamine (0.66 mL) in DCM (9 mL) at 0° C. The solution (total volume 11 mL) was stirred for 10 min and then 1 h at room temperature to afford a stock solution (11 mL). Aliquots of this were used directly without further purification to prepare examples 41-45.

A solution of tert-butyl (4-methylpiperidin-4-yl)carbamate (74 mg) in DCM (1 mL) was added to a 1 mL aliquot of the above stock solution and the reaction stirred for 20 h. 4 M HCl in dioxane (1 mL) was added and the reaction allowed to stir for a further 20 h. The volatiles were removed in vacuo and the crude material was dissolved in methanol (2 mL) and loaded onto a 10 g SCX cartridge. The impurities were washed through with methanol (75 mL) and discarded. The product was eluted with 1 N methanolic ammonia (75 mL) and evaporated in vacuo. Purification by preparative HPLC (Gemini-NX C18 column using a 95-5% gradient of aqueous 0.1% ammonia in methanol as eluent) afforded the title product (10 mg) as a solid.

MS: APCI(+ve) 563 (M+H)⁺.

$^1$H NMR δ(DMSO-d$_6$) 8.52 (d, 1H), 8.36 (d, 1H), 8.17 (s, 1H), 7.68-7.64 (m, 2H), 7.53 (dd, 1H), 7.34 (s, 1H), 4.89 (t, 1H), 4.10 (s, 1H), 3.94 (dd, 2H), 3.84 (q, 1H), 3.32 (s, 4H), 3.17 (s, 1H), 3.11 (d, 2H), 2.85 (sextet, 1H), 2.60-2.32 (m, 4H), 2.23 (d, 3H), 1.33 (d, 3H), 0.98 (s, 3H), 0.87 (s, 6H), 0.69 (td, 2H), 0.58-0.54 (m, 2H).

EXAMPLE 42

3-[4-{1-[(3R)-3-Aminopiperidin-1-yl]ethyl}-2-(3-hydroxy-2,2-dimethylpropyl)-1-oxo-1,2-dihydroisoquinolin-6-yl]-N-cyclopropyl-5-fluoro-4-methylbenzamide

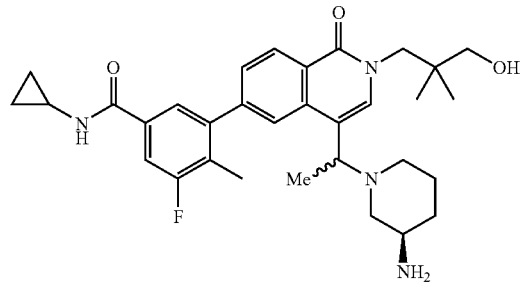

The title compound was prepared from tert-butyl (3R)-piperidin-3-ylcarbamate (69 mg) and a 1 mL aliquot of the stock solution (Example 41b), by the method of Example 41b to afford the title product (7 mg) as a solid.

MS: APCI(+ve) 549 (M+H)⁺.

$^1$H NMR δ(DMSO-d$_6$) 8.53 (t, 1H), 8.36 (dd, 1H), 8.11 (d, 1H), 7.68-7.63 (m, 2H), 7.52 (dd, 1H), 7.33 (d, 1H), 4.90 (s, 1H), 4.10 (s, 1H), 4.00-3.90 (m, 2H), 3.85 (q, 1H), 3.32 (s, 2H), 3.17 (s, 1H), 3.12 (s, 1H), 2.89-2.82 (m, 1H), 2.76 (d, 1H), 2.71-2.64 (m, 1H), 2.61-2.54 (m, 1H), 2.22 (t, 3H), 2.15 (t, 1H), 1.98 (t, 1H), 1.89 (t, 1H), 1.75-1.63 (m, 1H), 1.61-1.50 (m, 1H), 1.30 (d, 3H), 0.88 (s, 6H), 0.72-0.67 (m, 2H), 0.58-0.54 (m, 2H).

EXAMPLE 43

N-Cyclopropyl-3-{4-[1-(1,4-diazepan-1-yl)ethyl]-2-(3-hydroxy-2,2-dimethylpropyl)-1-oxo-1,2-dihydroisoquinolin-6-yl}-5-fluoro-4-methylbenzamide

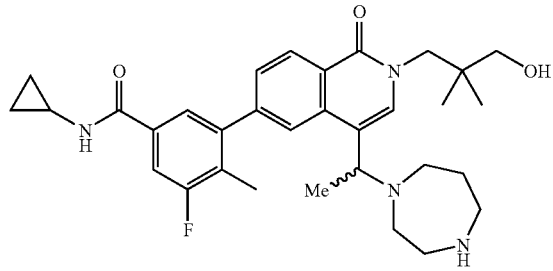

The title compound was prepared from tert-butyl 1,4-diazepane-1-carboxylate (69 mg) and a 1 mL aliquot of the stock solution (Example 41b), by the method of Example 41b, to afford the title product (13 mg) as a solid.

MS: APCI(+ve) 549 (M+H)⁺.

$^1$H NMR δ(DMSO-d$_6$) 8.53 (d, 1H), 8.34 (d, 1H), 8.11 (d, 1H), 7.65 (t, 2H), 7.51 (dd, 1H), 7.32 (s, 1H), 4.90 (s, 1H), 4.19 (q, 1H), 3.96 (d, 2H), 3.30 (s, 2H), 3.17 (s, 2H), 3.11 (s, 2H), 2.89-2.82 (m, 1H), 2.72-2.57 (m, 5H), 2.21 (d, 3H), 1.59-1.49 (m, 1H), 1.44-1.34 (m, 1H), 1.29 (d, 3H), 0.88 (d, 6H), 0.71-0.66 (m, 2H), 0.58-0.54 (m, 2H)

EXAMPLE 44 (DIASTERIOMER 1) AND 45 (DIASTERIOMER 2)

N-Cyclopropyl-3-fluoro-5-[2-(3-hydroxy-2,2-dimethylpropyl)-4-{1-[(3R)-3-(hydroxymethyl)piperazin-1-yl]ethyl}-1-oxo-1,2-dihydroisoquinolin-6-yl]-4-methylbenzamide

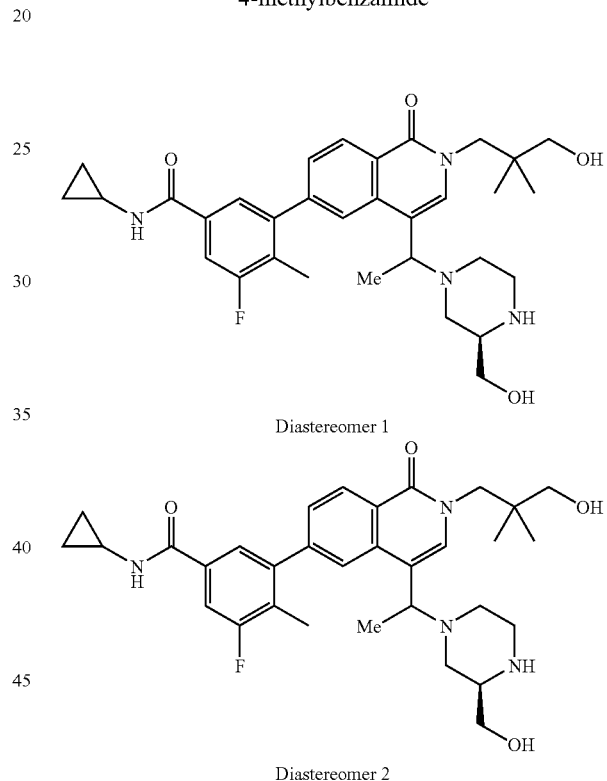

Diastereomer 1

Diastereomer 2 tert-Butyl (2R)-2-(hydroxymethyl)piperazine-1-carboxylate (0.41 g) was reacted with an 8 mL aliquot of the stock solution (Example 41b), by the method of Example 41b to afford the crude product as a racemate (60 mg). The crude product was purified by either preparative HPLC (Chiralpak AD (10×250 mm) column using 90:10 isohexane:ethanol with 0.1% diethylamine as eluent) or by preparative SFC (Chiralpak IA (20×250 mm) column using 30% isopropylamine with 0.1% diethylamine as eluent). The relevant fractions were evaporated to dryness to afford the separated title products: diastereomer 1 (16 mg) and diastereomer 2 (10 mg), each as a white solid.

Diastereomer 1:

MS: APCI(+ve) 565 (M+H)⁺.

$^1$H NMR δ(DMSO-d$_6$) 8.52 (d, 1H), 8.37 (d, 1H), 8.14 (s, 1H), 7.68-7.63 (m, 2H), 7.53 (dd, 1H), 7.36 (s, 1H), 4.87 (t, 1H), 4.41 (t, 1H), 3.99 (d, 1H), 3.88 (d, 1H), 3.81-3.74 (m,

1H), 3.22-3.18 (m, 1H), 3.17 (d, 2H), 3.11 (d, 2H), 2.88-2.68 (m, 4H), 2.24 (d, 3H), 2.03-1.95 (m, 2H), 1.85-1.78 (m, 2H), 1.31 (d, 3H), 0.87 (s, 6H), 0.72-0.66 (m, 2H), 0.59-0.54 (m, 2H).

Diastereomer 2:

MS: APCI(+ve) 565 (M+H)$^+$.

$^1$H NMR δ(DMSO-d$_6$) 8.52 (d, 1H), 8.37 (d, 1H), 8.15 (s, 1H), 7.68-7.63 (m, 2H), 7.53 (dd, 1H), 7.35 (s, 1H), 4.87 (t, 1H), 4.43 (t, 1H), 3.94 (d, 2H), 3.82-3.74 (m, 1H), 3.26-3.19 (m, 1H), 3.17 (d, 2H), 3.11 (d, 2H), 2.89-2.75 (m, 4H), 2.69-2.54 (m, 2H), 2.24 (d, 3H), 2.16-2.09 (m, 1H), 1.70-1.63 (m, 1H), 1.31 (d, 3H), 0.87 (d, 6H), 0.72-0.66 (m, 2H), 0.59-0.54 (m, 2H).

EXAMPLE 46

N-Cyclopropyl-3-[4-(1,4-diazepan-1-ylsulfonyl)-2-(3-hydroxy-2,2-dimethylpropyl)-1-oxo-1,2-dihydroisoquinolin-6-yl]-5-fluoro-4-methylbenzamide

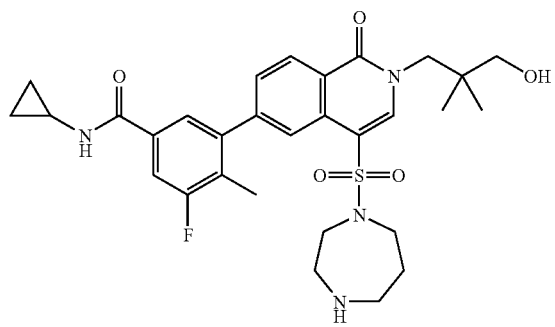

a)
6-Bromo-1-oxo-1,2-dihydroisoquinoline-4-sulfonyl chloride

A solution of 6-bromoisoquinolin-1(2H)-one (10 g) in chlorosulfuric acid (29.9 mL) was heated at 90° C. for 2 h. Chlorosulfuric acid (29.9 mL) was added, and the reaction mixture was poured onto ice (CAUTION). The resulting solid was filtered, washed with water, and dried in vacuo (25° C.) to give the subtitle compound as a beige solid (12.31 g).

$^1$H NMR δ(DMSO-d$_6$) 9.68 (s, 1H), 8.56 (d, 1H), 8.11 (d, 1H), 7.66 (dd, 1H), 7.52 (s, 1H).

b) tert-Butyl 4-[(6-bromo-1-oxo-1,2-dihydroisoquinolin-4-yl)sulfonyl]-1,4-diazepane-1-carboxylate To a solution of tert-butyl 1,4-diazepane-1-carboxylate (0.621 g) and triethylamine (0.864 mL) in THF (12 mL) was added dropwise a solution of 6-bromo-1-oxo-1,2-dihydroisoquinoline-4-sulfonyl chloride (Example 46a, 1 g) in THF (20 mL). The reaction was stirred at room temperature for 20 min. The resulting solution was concentrated under reduced pressure, acidified with 2 M HCl, and extracted into ethyl acetate. The combined organics were dried (MgSO$_4$), filtered and evaporated under reduced pressure to give the subtitle compound (1.097 g) that was used without further purification.

MS: APCI(-ve) 486/8 (M-H)$^-$.

c) tert-Butyl 4-{[6-bromo-2-(3-{[tert-butyl(dimethyl)silyl]oxy}-2,2-dimethylpropyl)-1-oxo-1,2-dihydroisoquinolin-4-yl]sulfonyl}-1,4-diazepane-1-carboxylate A solution of tert-butyl 4-[(6-bromo-1-oxo-1,2-dihydroisoquinolin-4-yl)sulfonyl]-1,4-diazepane-1-carboxylate (Example 46b, 0.082 g) dissolved in DMF (2 mL) was treated with cesium carbonate (0.110 g) and (3-bromo-2,2-dimethylpropoxy)(tert-butyl)dimethylsilane (0.057 g) under nitrogen. The resulting mixture was stirred at 100° C. for 6 h. The cooled reaction mixture was diluted with water (300 mL), and extracted with diethyl ether (300 mL×3). The combined organics were dried (MgSO$_4$), filtered and evaporated. The crude product was purified (SiO$_2$ chromatography, elution 30% diethyl ether/isohexane, then 50% DCM/isohexane) to afford the subtitle compound as a yellow solid (83 mg) which was used without further analysis in the next step.

d) tert-Butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)-1,4-diazepane-1-carboxylate A solution of tert-butyl 4-{[6-bromo-2-(3-{[tert-butyl(dimethyl)silyl]oxy}-2,2-dimethylpropyl)-1-oxo-1,2-dihydroisoquinolin-4-yl]sulfonyl}-1,4-diazepane-1-carboxylate (Example 46c, 83 mg) in DMF (2 mL) was treated with N-cyclopropyl-3-fluoro-4-methyl-5-(4,4,5,5-tetramethyl-1,3,2-dioxaborolan-2-yl)benzamide (39 mg), Pd-118 (2.4 mg) and potassium carbonate (33 mg) under nitrogen. The resulting mixture was stirred at 70° C. for 1 h. The cooled reaction mixture was partitioned between ethyl acetate and water. The aqueous was extracted with ethyl acetate (2×100 mL). The combined organics were washed with water (3×100 mL), brine (3×100 mL) dried (MgSO$_4$), filtered, and evaporated under reduced pressure. The crude product was purified (SiO$_2$ chromatography, elution with 50% ethyl acetate/isohexane) to afford the subtitle compound (0.055 g).

MS: APCI(+ve) 699/700/701 (M+H-BOC)$^+$.

e) N-Cyclopropyl-3-[4-(1,4-diazepan-1-ylsulfonyl)-2-(3-hydroxy-2,2-dimethylpropyl)-1-oxo-1,2-dihydroisoquinolin-6-yl]-5-fluoro-4-methylbenzamide To a solution of tert-butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)-1,4-diazepane-1-carboxylate (Example 46d, 0.055 g) in DCM (4 mL) was added trifluoroacetic acid (1 mL), and the reaction was stirred at room temperature overnight. Toluene (6 mL) was added and the volatiles removed in vacuo (repeated 3 times). The residue was dissolved in methanol and purified by SCX, flushing with methanol (impurities), and eluting the product with 0.7 N methanolic ammonia. Purification by preparative HPLC (Phenomenex Gemini column using a 95-5% gradient of 0.2% aqueous trifluoroacetic acid in acetonitrile as eluent), evaporation of solvents and trituration with diethyl ether gave the title compound (0.011 g) as a white solid.

MS: APCI(+ve) 585 (M+H)$^+$.

¹H NMR δ (CD₃OD) 8.54 (d, 1H), 8.32 (s, 1H), 8.13 (d, 1H), 7.69 (dd, 1H), 7.67-7.61 (m, 3H), 4.15 (s, 2H), 3.79-3.73 (m, 2H), 3.58 (t, 2H), 3.42-3.38 (m, 2H), 2.88 (dquintet, 1H), 2.27 (d, 3H), 2.23-2.12 (m, 2H), 2.05 (t, 3H), 1.01 (s, 6H), 0.87-0.79 (m, 2H), 0.70-0.63 (m, 2H).

EXAMPLE 47

N-Cyclopropyl-3-[2-(cyclopropylmethyl)-1-oxo-4-(piperazin-1-ylsulfonyl)-1,2-dihydroisoquinolin-6-yl]-5-fluoro-4-methylbenzamide

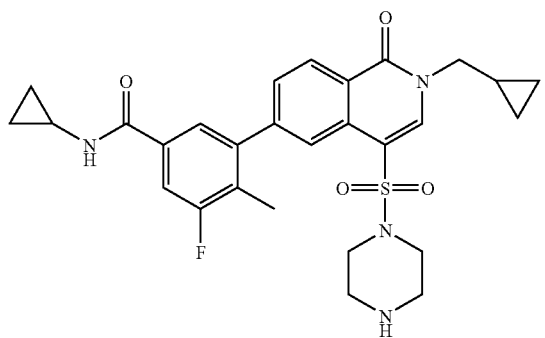

a) tert-Butyl 4-[(6-bromo-1-oxo-1,2-dihydroisoquinolin-4-yl)sulfonyl]piperazine-1-carboxylate To a solution of tert-butyl piperazine-1-carboxylate (0.67 g) and triethylamine (1.0 mL) in THF (20 mL) was added dropwise a solution of 6-bromo-1-oxo-1,2-dihydroisoquinoline-4-s sulfonyl chloride (Example 46a, 1.16 g) in THF (30 mL). The reaction was stirred at room temperature for 20 min. This was combined with another similar reaction (scale: 0.119 g of sulfonyl chloride), and the resulting solution was concentrated under reduced pressure, acidified with 2 M HCl and then extracted with ethyl acetate. The organics were combined, dried (MgSO₄), filtered and evaporated under reduced pressure to leave the subtitle compound (1.70 g).

MS: APCI(−ve) 470/4 (M−H)⁻.

b) tert-Butyl 4-{[6-bromo-2-(cyclopropylmethyl)-1-oxo-1,2-dihydroisoquinolin-4-yl]sulfonyl}piperazine-1-carboxylate A solution of tert-butyl 4-[(6-bromo-1-oxo-1,2-dihydroisoquinolin-4-yl)sulfonyl]piperazine-1-carboxylate (Example 47a, 1.70 g) in 1-methyl-2-pyrrolidinone (10 mL) was treated with (bromomethyl)cyclopropane (0.41 mL) and potassium carbonate (0.796 g). The resulting mixture was stirred at 70° C. overnight. The cooled reaction mixture was partitioned between water (250 mL) and ethyl acetate. The organic was separated and the aqueous extracted with further ethyl acetate. The combined organics were washed with water (2×200 mL) and brine (100 mL), dried (MgSO₄), filtered and concentrated to dryness. The residue was purified (SiO₂ chromatography, elution 10% ethyl acetate/isohexane then 50% ethyl acetate/isohexane) to afford the subtitle compound (0.890 g) as a pale yellow solid.

MS: APCI(+ve) 426 (M+H−BOC)⁺.

¹H NMR δ (CDCl₃) 8.34-8.30 (m, 2H), 8.12 (s, 1H), 7.68 (dd, 1H), 3.91 (d, 2H), 3.51-3.46 (m, 4H), 3.23-3.18 (m, 4H), 1.47-1.41 (m, 10H), 0.71-0.65 (m, 2H), 0.47-0.42 (m, 2H).

c) tert-Butyl 4-({6-[5-(cyclopropylcarbamoyl)-3-fluoro-2-methylphenyl]-2-(cyclopropylmethyl)-1-oxo-1,2-dihydroisoquinolin-4-yl}sulfonyl)piperazine-1-carboxylate A solution of tert-butyl 4-{[6-bromo-2-(cyclopropylmethyl)-1-oxo-1,2-dihydroisoquinolin-4-yl]sulfonyl}piperazine-1-carboxylate (Example 47b, 0.890 g) in DMF (10 mL) was treated with N-cyclopropyl-3-fluoro-4-methyl-5-(4,4,5,5-tetramethyl-1,3,2-dioxaborolan-2-yl)benzamide (0.491 g), Pd-118 (0.030 g) and potassium carbonate (0.425 g). The mixture was stirred at 70° C. for 1 h. The cooled reaction mixture was diluted with water (100 mL), and extracted into ethyl acetate (3×100 mL). The combined organic extracts were washed with brine (3×100 mL), dried (MgSO₄), filtered and evaporated. The crude product was purified (SiO₂ chromatography, elution with 10% ethyl acetate/DCM) to afford the subtitle compound (0.713 g) as beige foam, which was used without further analysis.

d) N-Cyclopropyl-3-[2-(cyclopropylmethyl)-1-oxo-4-(piperazin-1-ylsulfonyl)-1,2-dihydroisoquinolin-6-yl]-5-fluoro-4-methylbenzamide To a solution of tert-butyl 4-({6-[5-(cyclopropylcarbamoyl)-3-fluoro-2-methylphenyl]-2-(cyclopropylmethyl)-1-oxo-1,2-dihydroisoquinolin-4-yl}sulfonyl)piperazine-1-carboxylate (Example 47c, 0.141 g) dissolved in DCM (10 mL) was added trifluoroacetic acid (0.5 mL). The reaction mixture was stirred at room temperature overnight. The reaction was purified by SCX, flushing with methanol (impurities), and eluting the product with 0.7 N methanolic ammonia. Purification by preparative HPLC (Xbridge column using a 95-5% gradient of aqueous ammonia in acetonitrile as eluent) followed by concentration under reduced pressure gave a white solid. This was combined with material from another reaction (scale: 0.097 g of starting material) to give the title compound (0.034 g) as a white solid.

MS: APCI(+ve) 539 (M+H)⁺.

¹H NMR δ (CD₃OD) 8.56-8.46 (m, 1H), 8.36-8.29 (m, 1H), 8.27-8.21 (m, 1H), 7.69-7.55 (m, 3H), 4.05 (d, 2H), 3.22-3.13 (m, 4H), 2.91-2.70 (m, 5H), 2.28-2.18 (m, 3H), 1.46-1.27 (m, 1H), 1.25-1.10 (m, 1H), 0.87-0.74 (m, 2H), 0.71-0.57 (m, 4H), 0.56-0.46 (m, 2H).

EXAMPLE 48

N-Cyclopropyl-3-{2-(cyclopropylmethyl)-4-[(4-methylpiperazin-1-yl)sulfonyl]-1-oxo-1,2-dihydroisoquinolin-6-yl}-5-fluoro-4-methylbenzamide

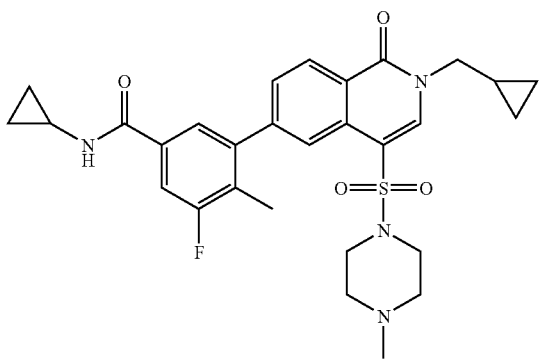

Acetic acid (3 drops) was added to a mixture of N-cyclopropyl-3-[2-(cyclopropylmethyl)-1-oxo-4-(piperazin-1-ylsulfonyl)-1,2-dihydroisoquinolin-6-yl]-5-fluoro-4-methylbenzamide (Example 47d, 0.047 g) and paraformaldehyde (7.9 mg) in 1,2-dichloroethane (1 mL). The mixture was stirred at room temperature overnight then sodium triacetoxyborohydride (18.5 mg) was added and the reaction stirred at room temperature for 1 h. DCM (10 mL) was added and the solution washed with water (3×10 mL). The organics were dried (MgSO₄), filtered and concentrated under reduced pressure then purified by preparative HPLC (Xbridge column using a 95-5% gradient of aqueous trifluoroacetic acid in acetonitrile) then evaporated to dryness. The product was passed through an ion exchange column (StratoSpheres TM SPE PL-HCO3 MP SPE by Polymer Laboratories, eluting with methanol), to give, after triturating with diethyl ether, the title compound (0.032 g) as a white solid.

MS: APCI(+ve) 553 (M+H)⁺.

¹H NMR δ (CDCl₃) 8.40 (d, 1H), 8.12 (s, 1H), 8.07 (d, 1H), 7.54 (dd, 1.5 Hz, 1H), 7.46 (d, 1H), 7.42 (dd, 1H), 6.92 (d, 1H), 3.96 (d, 2H), 3.20 (t, 4H), 2.92 (dsextet, 1H), 2.41 (t, 4H), 2.25 (s, 3H), 2.15 (d, 3H), 1.36-1.25 (m, 1H), 0.84 (td, 2H), 0.70-0.63 (m, 4H), 0.49-0.43 (m, 2H).

EXAMPLE 49

N-Cyclopropyl-3-fluoro-5-[2-(3-hydroxy-2,2-dimethylpropyl)-4-{[(3R)-3-(hydroxymethyl)piperazin-1-yl]sulfonyl}-1-oxo-1,2-dihydroisoquinolin-6-yl]-4-methylbenzamide

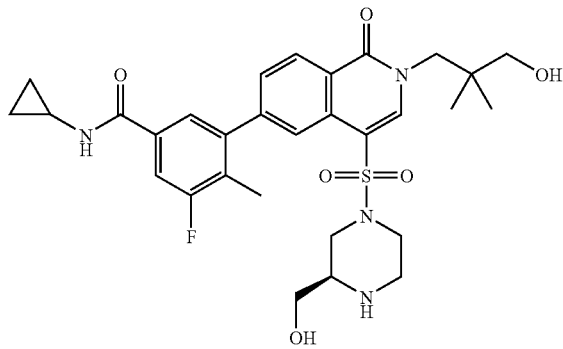

a) tert-Butyl (2R)-4-[(6-bromo-1-oxo-1,2-dihydroisoquinolin-4-yl)sulfonyl]-2-(hydroxymethyl)piperazine-1-carboxylate To a solution of tert-butyl (2R)-2-(hydroxymethyl)piperazine-1-carboxylate (0.479 g) and triethylamine (0.618 mL) in THF (6 mL) was added dropwise a solution of 6-bromo-1-oxo-1,2-dihydroisoquinoline-4-sulfonyl chloride (Example 46a, 0.715 g) in THF (10 mL). The reaction was stirred at room temperature for 20 min. The resulting solution was concentrated under reduced pressure before adding water and extracting into ethyl acetate. The combined organics were dried (MgSO₄), filtered and evaporated under reduced pressure. Trituration with ethyl acetate gave the subtitle compound (0.855 g).

MS: APCI(−ve) 500/504 (M−H)⁻.

¹H NMR δ (CDCl₃) 8.34 (d, 1H), 8.30 (d, 1H), 8.05 (s, 1H), 7.73 (dd, 1H), 4.32-4.18 (m, 1H), 4.00 (d, 1H), 3.88 (d, 1H), 3.72 (d, 1H), 3.63 (d, 2H), 3.10-2.96 (m, 1H), 2.84 (td, 2H), 1.44 (s, 9H).

b) tert-Butyl (2R)-4-{[6-bromo-2-(3-{[tert-butyl(dimethyl)silyl]oxy}-2,2-dimethylpropyl)-1-oxo-1,2-dihydroisoquinolin-4-yl]sulfonyl}-2-(hydroxymethyl)piperazine-1-carboxylate]

A solution of tert-butyl (2R)-4-[(6-bromo-1-oxo-1,2-dihydroisoquinolin-4-yl)sulfonyl]-2-(hydroxymethyl)piperazine-1-carboxylate (Example 49a, 0.855 g) dissolved in DMF (20 mL) was treated with (3-bromo-2,2-dimethylpropoxy)(tert-butyl)dimethylsilane (0.718 g) and cesium carbonate (1.109 g). The reaction was heated at 110° C. for 107 h. The reaction was cooled and partitioned between ethyl acetate and brine. The organics were washed with brine (×3), dried (MgSO₄), filtered and evaporated to leave the crude product. This was purified (SiO₂ chromatography, elution with 100% DCM then 10-50% ethyl acetate/isohexane) to afford the subtitle compound (0.580 g).

MS: APCI(+ve) 602 (M+H-BOC)⁺.

¹H NMR δ (CDCl₃) 8.31 (d, 1H), 8.19-8.17 (m, 2H), 7.68 (dd, 1H), 4.49-4.39 (m, 1H), 4.06 (s, 2H), 4.00-3.84 (m, 6H), 3.70 (d, 1H), 3.31 (s, 2H), 3.14 (td, 1H), 2.85-2.63 (m, 2H), 1.55 (s, 9H), 0.95 (s, 9H), 0.93 (s, 6H), 0.10 (s, 4H).

c) tert-Butyl (2R)-4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)-2-(hydroxymethyl)piperazine-1-carboxylate A solution of tert-butyl (2R)-4-{[6-bromo-2-(3-{[tert-butyl(dimethyl)silyl]oxy}-2,2-dimethylpropyl)-1-oxo-1,2-dihydroisoquinolin-4-yl]sulfonyl}-2-(hydroxymethyl)piperazine-1-carboxylate (Example 49b, 0.58 g) in DMF (10 mL) was treated with N-cyclopropyl-3-fluoro-4-methyl-5-(4,4,5,5-tetramethyl-1,3,2-dioxaborolan-2-yl)benzamide (0.263 g), Pd-118 (0.016 g) and potassium carbonate (0.228 g). The resulting mixture was stirred at 75° C. for 6 h. The cooled reaction was concentrated under reduced pressure then purified (SiO₂ chromatography, loaded in DCM, flushed with isohexane (100 mL), then DCM (200 mL), followed by a 10-100% gradient of ethyl acetate/isohexane) to afford the subtitle compound (0.537 g).

¹H NMR δ (CDCl₃) 8.53 (d, 1H), 8.21 (s, 1H), 8.03-8.00 (m, 1H), 7.53 (dd, 1H), 7.47-7.45 (m, 1H), 7.43 (d, 1H), 6.23 (s, 1H), 4.50-4.43 (m, 1H), 4.10 (d, 2H), 4.01-3.95 (m, 2H), 3.95-3.92 (m, 1H), 3.88-3.82 (m, 1H), 3.68-3.62 (m, 1H), 3.35-3.32 (m, 2H), 3.16-3.08 (m, 1H), 2.96 (s, 2H), 2.93-2.85 (m, 3H), 2.79-2.65 (m, 2H), 2.22 (d, 3H), 2.08 (dd, 3H), 1.92 (s, 1H), 1.24 (s, 6H), 0.96 (s, 9H), 0.90-0.85 (m, 2H), 0.64-0.59 (m, 2H), 0.11 (s, 6H).

d) N-Cyclopropyl-3-fluoro-5-[2-(3-hydroxy-2,2-dimethylpropyl)-1-oxo-4-{[(8aR)-3-oxotetrahydro[1,3]oxazolo[3,4-a]pyrazin-7(1H)-yl]sulfonyl}-1,2-dihydroisoquinolin-6-yl]-4-methylbenzamide tert-Butyl (2R)-4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)-2-(hydroxymethyl)piperazine-1-carboxylate (Example 49c, 0.537 g) was dissolved in DCM (10 mL) and treated with trifluoroacetic acid (3 mL). The reaction mixture was diluted with toluene (5 mL) and evaporated under reduced pressure.

MS: APCI(+ve) 627 (M+H)+.

e) N-Cyclopropyl-3-fluoro-5-[2-(3-hydroxy-2,2-dimethylpropyl)-4-{[(3R)-3-(hydroxymethyl)piperazin-1-yl]sulfonyl}-1-oxo-1,2-dihydroisoquinolin-6-yl]-4-methylbenzamide 2 N aqueous NaOH solution (2 mL) was added to a solution of N-cyclopropyl-3-fluoro-5-[2-(3-hydroxy-2,2-dimethylpropyl)-1-oxo-4-{[(8aR)-3-oxotetrahydro[1,3]oxazolo[3,4-a]pyrazin-7(1H)-yl]sulfonyl}-1,2-dihydroisoquinolin-6-yl]-4-methylbenzamide (Example 49d, 0.291 g) in methanol (2 mL) and the mixture stirred at 90° C. for 45 min. The reaction was neutralised with acetic acid and the volatiles removed under reduced pressure before partitioning between water and DCM. The organic layer was separated and the aqueous extracted further (2×) and the combined organics dried (MgSO$_4$), filtered and evaporated. The residue was purified by SCX (eluting with methanol to remove impurities, then flushing with methanolic ammonia to elute product). Further purification by preparative HPLC (Xbridge column using a 95-5% gradient of 0.3% aqueous ammonia in acetonitrile), solvent evaporation under reduced pressure and trituration with diethyl ether gave the title compound (0.059 g).

MS: APCI(+ve) 601 (M+H)+.

1H NMR δ (CDCl$_3$) 8.53 (d, 1H), 8.15 (s, 1H), 8.04 (s, 1H), 7.61 (s, 1H), 7.54 (d, 1H), 7.33 (d, 1H), 6.42 (s, 1H), 4.07 (d, 1H), 3.97-3.85 (m, 2H), 3.67-3.59 (m, 1H), 3.58-3.44 (m, 2H), 3.39-3.27 (m, 1H), 3.17 (s, 2H), 3.03 (d, 3H), 2.93-2.84 (m, 1H), 2.83-2.68 (m, 3H), 2.22 (s, 3H), 1.29-1.17 (m, 1H), 1.04 (d, 6H), 0.89 (d, 2H), 0.68-0.60 (m, 2H).

The following intermediate sulfonamides (Table 4) were prepared from 6-bromo-1-oxo-1,2-dihydroisoquinoline-4-sulfonyl chloride (Example 46a) and a suitable amine using the method of Example 46b.

TABLE 4

| Name | Structure | MS m/z | $^1$H NMR δ (DMSO-d$_6$) unless noted |
|---|---|---|---|
| tert-Butyl {1-[(6-bromo-1-oxo-1,2-dihydroisoquinolin-4-yl)sulfonyl]piperidin-4-yl}carbamate | 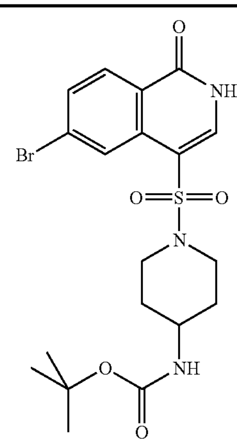 | APCI(−ve) 484/488 (M − H)− | 8.24-8.22(m, 1H), 8.19(d, 1H), 7.86-7.83(m, 1H), 7.81(dd, 1H), 3.59-3.50 (m, 2H), 2.86-2.77(m, 2H), 1.91(s, 2H), 1.78-1.70(m, 2H), 1.35(s, 9H), 1.33-1.21(m, 2H) |
| tert-Butyl {1-[(6-bromo-1-oxo-1,2-dihydroisoquinolin-4-yl)sulfonyl]piperidin-4-yl}methylcarbamate | 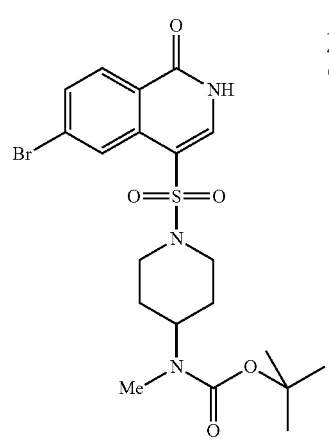 | APCI(−ve) 498/502 (M − H)− | |

TABLE 4-continued

| Name | Structure | MS m/z | $^{1}$H NMR δ (DMSO-$d_6$) unless noted |
|---|---|---|---|
| tert-Butyl {(3S)-1-[(6-bromo-1-oxo-1,2-dihydroisoquinolin-4-yl)sulfonyl]pyrrolidin-3-yl}carbamate | 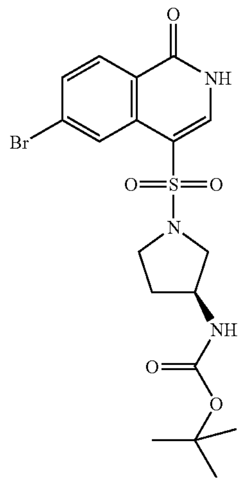 | APCI(−ve) 470/472 (M − H)$^-$ | |
| tert-Butyl {(3R)-1-[(6-bromo-1-oxo-1,2-dihydroisoquinolin-4-yl)sulfonyl]pyrrolidin-3-yl}carbamate | 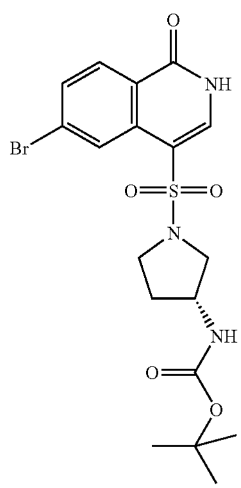 | APCI(−ve) 470/472 (M − H)$^-$ | |
| tert-Butyl ({(2R)-1-[(6-bromo-1-oxo-1,2-dihydroisoquinolin-4-yl)sulfonyl]pyrrolidin-2-yl}methyl)carbamate | 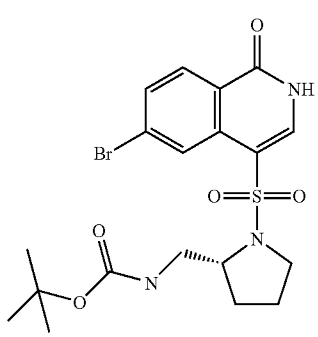 | APCI(−ve) 485(M − H)$^-$ | (CDCl$_3$) 8.48(s, 1H), 8.30(d, 1H), 8.05(s, 1H), 7.72 (dd, 1H), 4.90-4.84(m, 1H), 3.47-3.23(m, 4H), 1.95-1.49 (m, 4H), 1.45-1.39(m, 9H) |

TABLE 4-continued

| Name | Structure | MS m/z | ¹H NMR δ (DMSO-d₆) unless noted |
|---|---|---|---|
| 6-Bromo-N-[2-(dimethylamino)ethyl]-1-oxo-1,2-dihydroisoquinoline-4-sulfonamide | 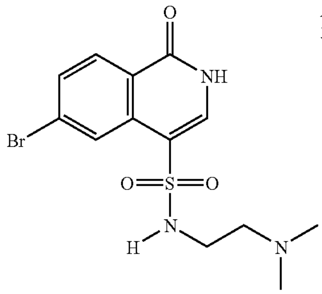 | APCI(+ve) 375 (M + H)⁺ | (CDCl₃) 8.39(d, 1H), 8.31(d, 1H), 8.04(s, 1H), 7.73 (dd, 1H), 2.98-2.94(m, 2H), 2.34-2.29(m, 2H), 2.06(s, 6H) |

The following intermediates (Table 5) were prepared using the methods described in Examples 46-49.

TABLE 5

| Name | Structure | MS m/z | ¹H NMR δ (DMSO-d₆) unless noted |
|---|---|---|---|
| tert-Butyl (1-{[6-bromo-2-(cyclopropylmethyl)-1-oxo-1,2-dihydroisoquinolin-4-yl]sulfonyl}piperidin-4-yl)carbamate | 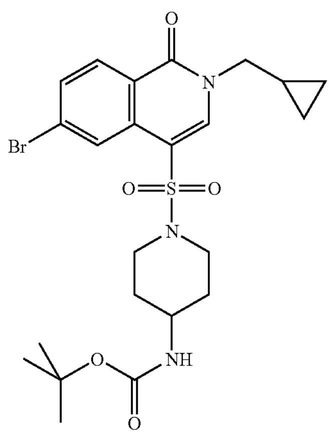 | | (CDCl₃) 8.32(d, 1H), 8.28(d, 1H), 8.11(s, 1H), 7.68(dd, 1H), 4.48-4.39 (m, 1H), 3.91(d, 2H), 3.78-3.69 (m, 2H), 3.60-3.51(m, 1H), 3.00(s, 1H), 2.92-2.85(m, 3H), 2.72(s, 2H), 1.66(s, 9H), 1.33-1.21 (m, 1H), 0.70-0.62(m, 2H), 0.47-0.40(m, 2H) |
| tert-Butyl (1-{[6-bromo-2-(cyclopropylmethyl)-1-oxo-1,2-dihydroisoquinolin-4-yl]sulfonyl}piperidin-4-yl)methylcarbamate | 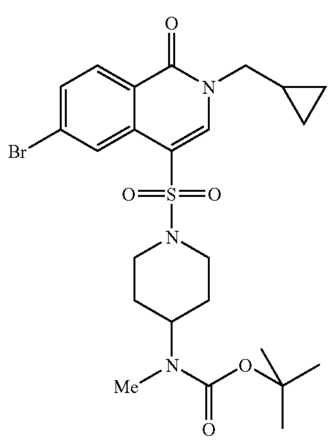 | APCI(+ve) 454(M + H − BOC)⁺ | |

TABLE 5-continued

| Name | Structure | MS m/z | ¹H NMR δ (DMSO-d₆) unless noted |
|---|---|---|---|
| tert-Butyl [(3S)-1-{[6-bromo-2-(3-{[tert-butyl(dimethyl)silyl]oxy}-2,2-dimethylpropyl)-1-oxo-1,2-dihydroisoquinolin-4-yl]sulfonyl}pyrrolidin-3-yl]carbamate | 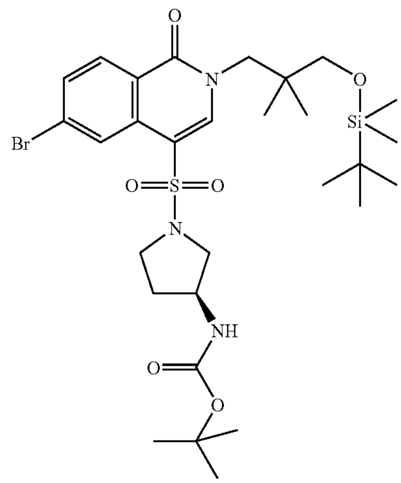 | APCI(+ve) 573(M + H − BOC)⁺ | |
| tert-Butyl [(3R)-1-{[6-bromo-2-(3-{[tert-butyl(dimethyl)silyl]oxy}-2,2-dimethylpropyl)-1-oxo-1,2-dihydroisoquinolin-4-yl]sulfonyl}pyrrolidin-3-yl]carbamate | 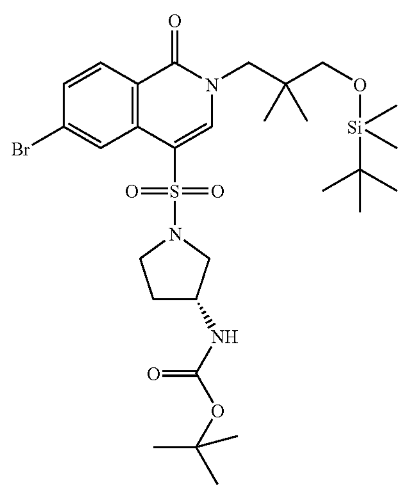 | APCI(−ve) 672(M − H)⁻ | |
| tert-Butyl {[(2R)-1-{[6-bromo-2-(3-{[tert-butyl(dimethyl)silyl]oxy}-2,2-dimethylpropyl)-1-oxo-1,2-dihydroisoquinolin-4-yl]sulfonyl}pyrrolidin-2-yl]methyl}carbamate | 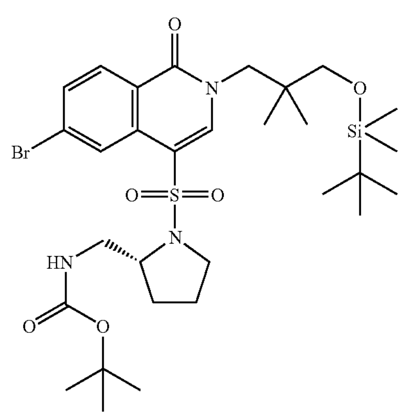 | APCI(+ve) 587(M + H − BOC)⁺ | |

TABLE 5-continued

| Name | Structure | MS m/z | ¹H NMR δ (DMSO-d₆) unless noted |
|---|---|---|---|
| 6-Bromo-2-(3-{[tert-butyl(dimethyl)silyl]oxy}-2,2-dimethylpropyl)-N-[2-(dimethylamino)ethyl]-1-oxo-1,2-dihydroisoquinoline-4-sulfonamide | 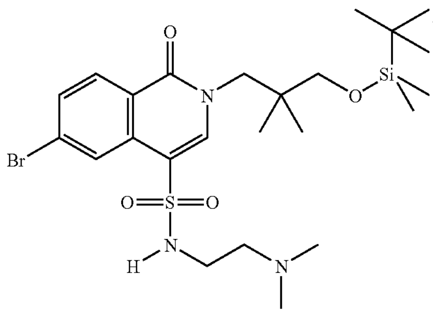 | APCI(+ve) 574/576 (M + H)⁺ | (CDCl₃) 8.35-8.28(m, 2H), 8.15(s, 1H), 7.67(d, 1H), 4.05(s, 2H), 3.32(s, 2H), 2.94-2.87(m, 2H), 2.30(t, 2H), 2.04(s, 6H), 1.26(s, 6H), 0.94(d, 9H), 0.10(d, 6H) |
| 6-Bromo-N-[2-(dimethylamino)ethyl]-2-(3-hydroxy-2,2-dimethylpropyl)-1-oxo-1,2-dihydroisoquinoline-4-sulfonamide (prepared by trifluoroacetic acid deprotection of above TBS analogue in table) | 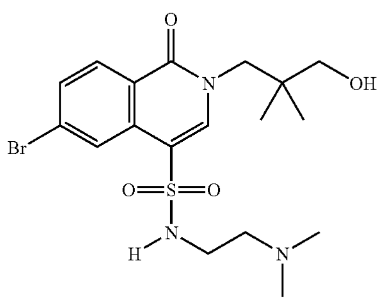 | APCI(−ve) 458/462 (M − H)⁻ | |
| tert-Butyl 4-{[6-bromo-2-(cyclopropylmethyl)-1-oxo-1,2-dihydroisoquinolin-4-yl]sulfonyl}-1,4-diazepane-1-carboxylate | 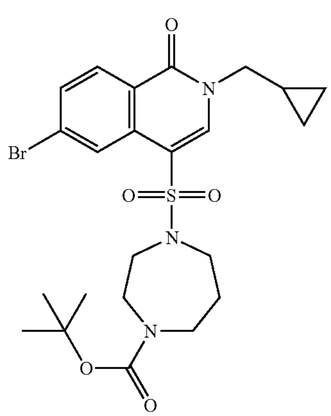 | APCI(+ve) 442(M + H − BOC)⁺ | (CDCl₃) 8.32(d, 1H), 8.22(d, 1H), 8.13(s, 1H), 7.70-7.64 (m, 1H), 3.91(d, 2H), 3.57-3.46 (m, 4H), 3.46-3.34(m, 4H), 2.08-1.91(m, 2H), 1.44(s, 9H), 1.33-1.21 (m, 1H), 0.70-0.62(m, 2H), 0.47-0.41(m, 2H). |

The following intermediates (Table 6) were prepared using the methods described in Examples 46-49.

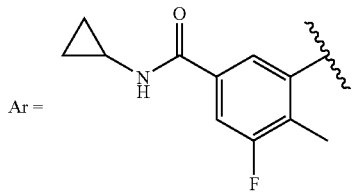

Ar =

TABLE 6

| Name | Structure | MS m/z | ¹H NMR δ (DMSO-$d_6$) unless noted |
|---|---|---|---|
| tert-Butyl [1-({6-[5-(cyclopropylcarbamoyl)-3-fluoro-2-methylphenyl]-2-(cyclopropylmethyl)-1-oxo-1,2-dihydroisoquinolin-4-yl}sulfonyl)piperidin-4-yl]carbamate | 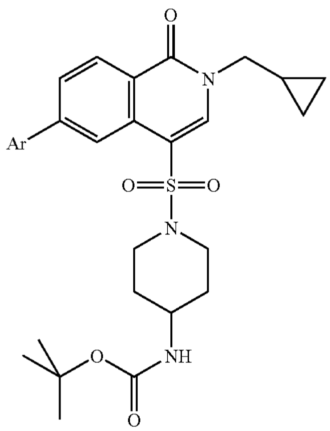 | APCI(−ve) 651(M − H)⁻ | 8.57-8.54(m, 1H), 8.43(d, 1H), 8.35(s, 1H), 8.11(d, 1H), 7.73-7.67 (m, 2H), 7.63(s, 1H), 6.88-6.83 (m, 1H), 4.01(d, 2H), 3.62-3.53 (m, 2H), 2.90-2.75(m, 3H), 2.19(d, 3H), 1.79-1.70(m, 2H), 1.40-1.25 (m, 11H), 0.72-0.65(m, 2H), 0.60-0.50(m, 4H), 0.47-0.42 (m, 2H) |
| tert-Butyl [1-({6-[5-(cyclopropylcarbamoyl)-3-fluoro-2-methylphenyl]-2-(cyclopropylmethyl)-1-oxo-1,2-dihydroisoquinolin-4-yl}sulfonyl)piperidin-4-yl]methylcarbamate | 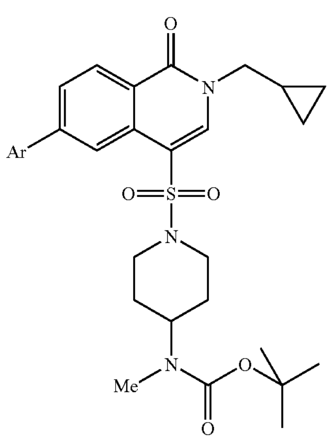 | APCI(−ve) 665(M − H)⁻ | |

TABLE 6-continued

| Name | Structure | MS m/z | $^1$H NMR δ (DMSO-d$_6$) unless noted |
|---|---|---|---|
| tert-Butyl [(3S)-1-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)pyrrolidin-3-yl]carbamate | 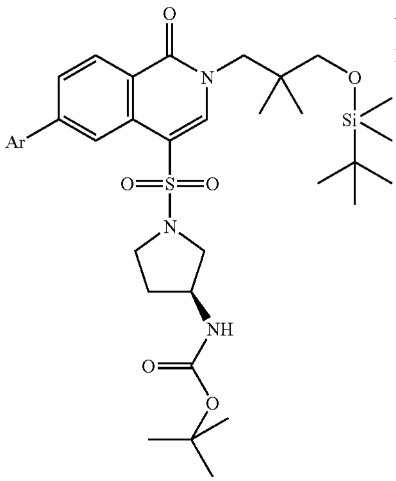 | APCI(+ve) 685(M + H − BOC)$^+$ | (CD$_3$OD) 8.38 (d, 1H), 8.17-8.14(m, 2H), 7.55-7.48(m, 3H), 4.03(d, 2H), 3.93-3.85 (m, 1H), 3.40-3.33(m, 2H), 3.32-3.29(m, 2H), 3.05-2.99 (m, 1H), 2.75 (dquintet, 1H), 2.61-2.49(m, 1H), 2.15(d, 3H), 2.08-1.95 (m, 1H), 1.75-1.66(m, 1H), 1.22(s, 9H), 1.09(s, 6H), 0.88-0.83(m, 9H), 0.72-0.66 (m, 2H), 0.56-0.50(m, 2H), 0.00(s, 6H) |
| tert-Butyl [(3R)-1-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)pyrrolidin-3-yl]carbamate | 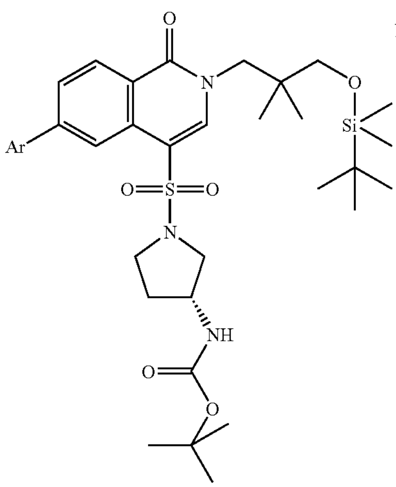 | APCI(+ve) 785(M + H)$^+$ | (CDCl$_3$) 8.50(d, 1H), 8.20(s, 1H), 8.17-8.14 (m, 1H), 7.52-7.46(m, 3H), 4.17-4.03(m, 4H), 3.54-3.32 (m, 7H), 2.96-2.86(m, 1H), 2.26-2.16(m, 4H), 1.30(s, 9H), 0.96-0.96 (m, 15H), 0.90-0.83(m, 3H), 0.62(d, 2H), 0.11(s, 6H) |
| tert-Butyl {[(2R)-1-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)pyrrolidin-2-yl]methyl}carbamate | 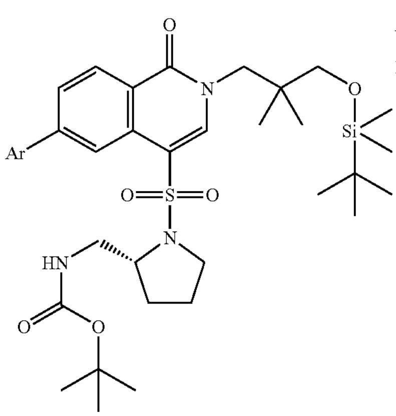 | APCI(+ve) 698(M + H − BOC)$^+$ | (CD$_3$OD) 8.38 (d, 1H), 8.20(s, 1H), 8.16(d, 1H), 7.54-7.47 (m, 3H), 4.13-3.97(m, 2H), 3.83-3.74(m, 1H), 3.40-3.28 (m, 3H), 2.96-2.88(m, 1H), 2.77-2.63(m, 2H), 2.13(d, 3H), 1.83-1.72 (m, 1H), 1.71-1.61(m, 3H), 1.25(s, 9H), 1.09(s, 2H), 0.89-0.83(m, 14H), 0.73-0.66(m, 2H), 0.55-0.50(m, 2H), 0.00(d, 6H) |

TABLE 6-continued

| Name | Structure | MS m/z | ¹H NMR δ (DMSO-d₆) unless noted |
|---|---|---|---|
| tert-Butyl 4-({6-[5-(cyclopropylcarbamoyl)-3-fluoro-2-methylphenyl]-2-(cyclopropylmethyl)-1-oxo-1,2-dihydroisoquinolin-4-yl}sulfonyl)-1,4-diazepane-1-carboxylate | 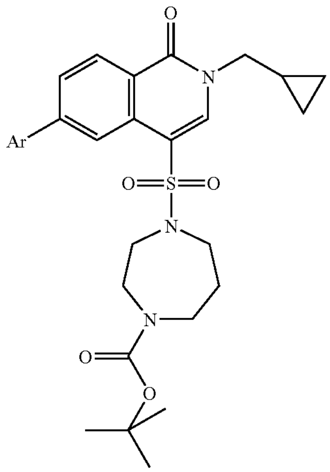 | APCI(−ve) 651(M − H)⁻ | (CDCl₃) 8.53-8.48(m, 1H), 8.20-8.12(m, 1H), 8.04-7.72 (m, 2H), 7.65-7.42(m, 3H), 4.01-3.93(m, 2H), 3.64-3.50 (m, 2H), 3.50-3.34(m, 5H), 3.34-3.27(m, 1H), 2.23-2.11 (m, 3H), 1.89-1.77(m, 2H), 1.65(s, 3H), 1.38(s, 3H), 1.09(s, 5H), 0.89-0.77(m, 2H), 0.70-0.60 (m, 4H), 0.50-0.43(m, 2H) |

The following Examples 50 to 56 (Table 7) were prepared from the above intermediates using similar methods to those described for Examples 47-49:

EXAMPLE 50

3-{4-[(4-Aminopiperidin-1-yl)sulfonyl]-2-(cyclopropylmethyl)-1-oxo-1,2-dihydroisoquinolin-6-yl}-N-cyclopropyl-5-fluoro-4-methylbenzamide

EXAMPLE 51

N-cyclopropyl-3-[2-(cyclopropylmethyl)-4-(1,4-diazepan-1-ylsulfonyl)-1-oxo-1,2-dihydroisoquinolin-6-yl]-5-fluoro-4-methylbenzamide

EXAMPLE 52

N-cyclopropyl-3-[2-(cyclopropylmethyl)-4-{[4-(methylamino)piperidin-1-yl]sulfonyl}-1-oxo-1,2-dihydroisoquinolin-6-yl]-5-fluoro-4-methylbenzamide

EXAMPLE 53

3-[4-{[(3S)-3-Aminopyrrolidin-1-yl]sulfonyl}-2-(3-hydroxy-2,2-dimethylpropyl)-1-oxo-1,2-dihydroisoquinolin-6-yl]-N-cyclopropyl-5-fluoro-4-methylbenzamide

EXAMPLE 54

3-[4-{[(3R)-3-Aminopyrrolidin-1-yl]sulfonyl}-2-(3-hydroxy-2,2-dimethylpropyl)-1-oxo-1,2-dihydroisoquinolin-6-yl]-N-cyclopropyl-5-fluoro-4-methylbenzamide

EXAMPLE 55

3-[4-{[(2R)-2-(aminomethyl)pyrrolidin-1-yl]sulfonyl}-2-(3-hydroxy-2,2-dimethylpropyl)-1-oxo-1,2-dihydroisoquinolin-6-yl]-N-cyclopropyl-5-fluoro-4-methylbenzamide

EXAMPLE 56

N-cyclopropyl-3-[4-{[2-(dimethylamino)ethyl]sulfamoyl}-2-(3-hydroxy-2,2-dimethylpropyl)-1-oxo-1,2-dihydroisoquinolin-6-yl]-5-fluoro-4-methylbenzamide

TABLE 7

| Example | Structure | MS m/z [M + H]⁺ | ¹H NMR δ (DMSO-d₆) unless otherwise noted |
|---|---|---|---|
| 50 | 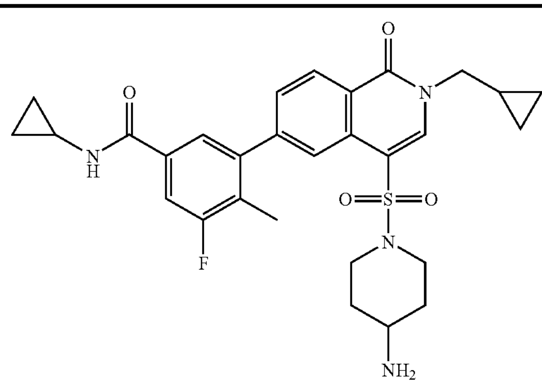 | 553 | (CD₃OD) 8.42(dd, 1H), 8.27 (s, 1H), 8.16(s, 1H), 7.60-7.53(m, 3H), 3.99(d, 2H), 3.71(d, 2H), 2.83(dquintet, 1H), 2.79-2.70(m, 2H), 2.66 (ddd, 1H), 2.19(s, 3H), 1.85-1.77(m, 2H), 1.38-1.23(m, 3H), 0.80-0.74(m, 2H), 0.64-0.57(m, 4H), 0.49-0.44(m, 2H) |

TABLE 7-continued

| Example | Structure | MS m/z [M + H]+ | 1H NMR δ (DMSO-d6) unless otherwise noted |
|---|---|---|---|
| 51 | 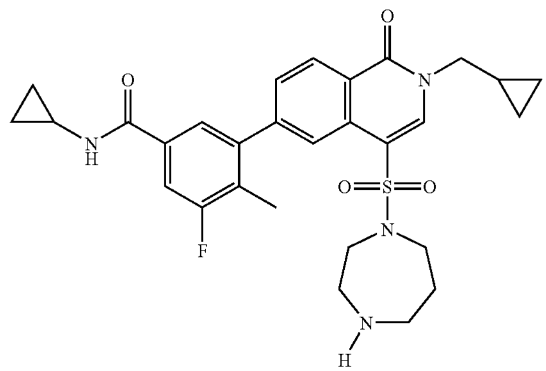 | 553 | (CD3OD) 8.38(d, 1H), 8.26(s, 1H), 8.06(d, 1H), 7.59-7.51 (m, 3H), 3.97(d, 2H), 3.54-3.43(m, 4H), 3.05-2.95(m, 4H), 2.85-2.78(m, 1H), 2.15 (d, 3H), 1.93-1.85(m, 2H), 1.37-1.24(m, 1H), 0.80-0.72(m, 2H), 0.65-0.55(m, 4H), 0.48-0.42(m, 2H) |
| 52 | 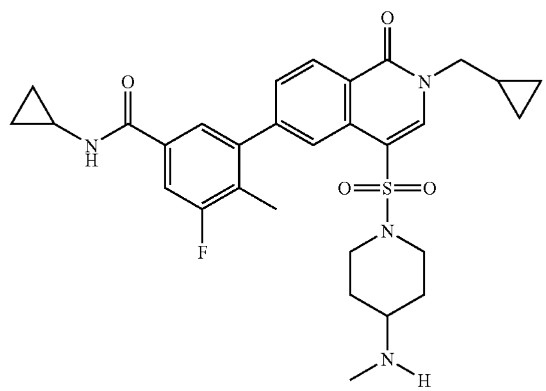 | 567 | (CD3OD) 8.48(d, 1H), 8.30(s, 1H), 8.19(d, 1H), 7.62(dd, 1H), 7.60-7.57(m, 2H), 4.01 (d, 2H), 3.77-3.70(m, 2H), 2.86-2.74(m, 3H), 2.46-2.33(m, 1H), 2.28(s, 3H), 2.22(d, 3H), 1.94-1.86(m, 2H), 1.39-1.20(m, 3H), 0.78 (td, 2H), 0.65-0.59(m, 4H), 0.50-0.45(m, 2H) |
| 53 | 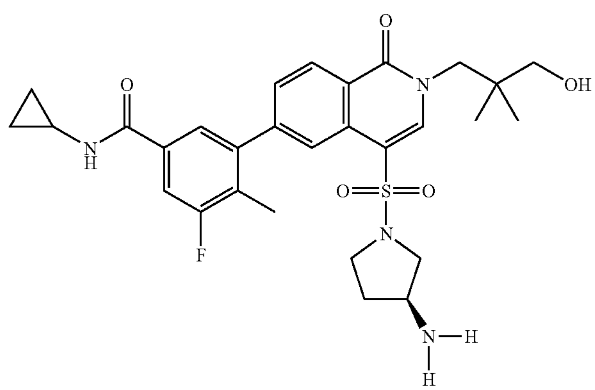 | 571 | 8.54(d, 1H), 8.42(d, 1H), 8.30(s, 1H), 8.14(d, 1H), 7.72-7.63(m, 3H), 4.97-4.87(m, 1H), 4.12-3.97(m, 3H), 3.48-3.34(m, 3H), 3.19-3.15(m, 4H), 2.92(dd, 1H), 2.86(dq, 1H), 2.20(d, 3H), 1.94(td, 1H), 1.58(td, 1H), 0.88(d, 6H), 0.73-0.67(m, 2H), 0.59-0.53(m, 2H) |
| 54 | 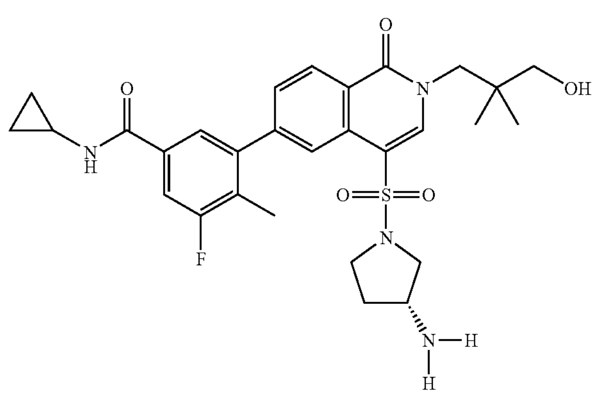 | 571 | 8.53(d, 1H), 8.42(d, 1H), 8.30(s, 1H), 8.14(d, 1H), 7.73-7.63(m, 3H), 4.96-4.90(m, 1H), 4.05(dd, 2H), 3.47-3.35 (m, 3H), 3.29(s, 2H), 3.19-3.15(m, 2H), 2.92(dd, 1H), 2.86(dsextet, 1H), 2.20(d, 3H), 1.94(td, 1H), 1.79-1.65 (m, 1H), 1.63-1.52(m, 1H), 0.88(d, 6H), 0.73-0.67(m, 2H), 0.59-0.54(m, 2H) |

TABLE 7-continued

| Example | Structure | MS m/z [M + H]⁺ | ¹H NMR δ (DMSO-d₆) unless otherwise noted |
|---|---|---|---|
| 55* | 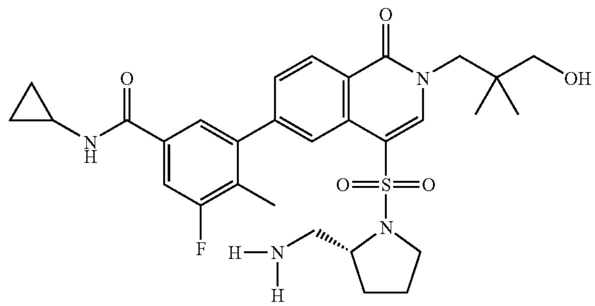 | 585 | 8.57(d, 1H), 8.42(d, 1H), 8.28(s, 1H), 8.18(s, 1H), 7.73-7.66(m, 2H), 7.63(s, 1H), 4.99(s, 1H), 4.12-4.02(m, 2H), 3.74-3.65(m, 1H), 3.30-3.26(m, 1H), 3.24-3.15(m, 3H), 2.85(dq, 1H), 2.61(dd, 1H), 2.47-2.42(m, 1H), 2.19 (d, 3H), 1.90-1.61(m, 4H), 0.88(d, 6H), 0.74-0.65(m, 2H), 0.59-0.52(m, 2H) |
| 56** | 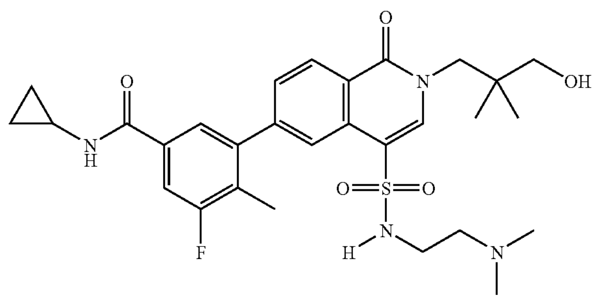 | 573 | 8.53(d, 1H), 8.41(d, 1H), 8.21(s, 1H), 8.17(s, 1H), 7.91-7.81(m, 1H), 7.71-7.61(m, 3H), 4.91(t, 1H), 4.04(s, 2H), 3.17(d, 2H), 2.92-2.81(m, 3H), 2.18(s, 3H), 2.14(t, 2H), 1.92(s, 6H), 0.87(s, 6H), 0.74-0.66(m, 2H), 0.59-0.53(m, 2H) |

*Example 55 final purification by RPHPLC needs to avoid aq trifluoroacetic acid eluents to remove undesired trifluoroacetamide formation.
**Example 56 final Suzuki coupling done directly on non silylated intermediate (Table 5).

EXAMPLE 57

N-Cyclopropyl-3-[4-(1,4-diazepan-1-ylmethyl)-2-{[1-(hydroxymethyl)cyclopropyl]methyl}-1-oxo-1,2-dihydroisoquinolin-6-yl]-5-fluoro-4-methylbenzamide

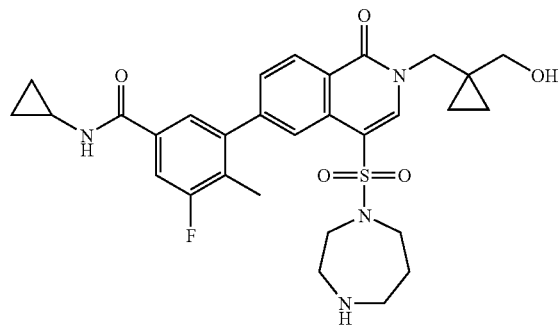

tert-Butyl 4-[(6-bromo-1-oxo-1,2-dihydroisoquinolin-4-yl)sulfonyl]-1,4-diazepane-1-carboxylate (Example 46b, 0.40 g), [1-({[tert-butyl(dimethyl)silyl]oxy}methyl)cyclopropyl]methyl methanesulfonate (0.24 g) and cesium carbonate (0.536 g) were stirred together in DMF (20 mL) at 110° C. for 72 h under nitrogen, cooled to room temperature, diluted with water (100 mL) and extracted into ethyl acetate (3×20 mL). The combined organics were washed with saturated brine (3×20 mL), dried (MgSO₄) filtered and evaporated, and the residue was purified (SiO₂ chromatography, elution with 10% ethyl acetate in DCM) to give (tert-butyl 4-[(6-bromo-2-{[1-({[tert-butyl(dimethyl)silyl]oxy}methyl)cyclopropyl]methyl}-1-oxo-1,2-dihydroisoquinolin-4-yl)sulfonyl]-1,4-diazepane-1-carboxylate) as a solid. This was dissolved in DMF (10 mL), treated with N-cyclopropyl-3-fluoro-4-methyl-5-(4,4,5,5-tetramethyl-1,3,2-dioxaborolan-2-yl)benzamide (0.089 g), potassium carbonate (0.077 g) and Pd-118 (0.006 g) and the resulting mixture was stirred at 70° C. under nitrogen for 1 h. After being cooled to room temperature, it was diluted with saturated brine and extracted into ethyl acetate (3×30 mL). The combined extracts were washed with brine (3×30 mL), dried (MgSO₄) filtered and evaporated. The residue was dissolved in THF (20 mL), treated with 4 M HCl in dioxane (3 mL), stirred at room temperature for 3 h, evaporated and purified by preparative HPLC (Waters Xbridge column using a 95-5% gradient of aqueous 0.2% ammonia in acetonitrile as eluent) to give the title compound (0.019 g) as a solid.

MS: APCI(+ve) 583 (M+H)⁺.

¹H NMR δ (DMSO-d₆) 8.54 (d, 1H), 8.41 (d, 1H), 8.30 (s, 1H), 8.03 (d, 1H), 7.73-7.63 (m, 2H), 4.79-4.69 (m, 1H), 4.17 (s, 2H), 3.45-3.29 (m, 4H), 3.27-3.21 (m, 2H), 2.91-2.80 (m,

1H), 2.77-2.66 (m, 4H), 2.18 (d, 3H), 1.68-1.58 (m, 2H), 0.95-0.78 (m, 1H), 0.74-0.63 (m, 4H), 0.60-0.53 (m, 2H), 0.51-0.46 (m, 2H).

EXAMPLE 58

N-Cyclopropyl-3-fluoro-5-[2-(3-hydroxy-2,2-dimethylpropyl)-1-oxo-4-(piperidin-4-ylsulfanyl)-1,2-dihydroisoquinolin-6-yl]-4-methylbenzamide

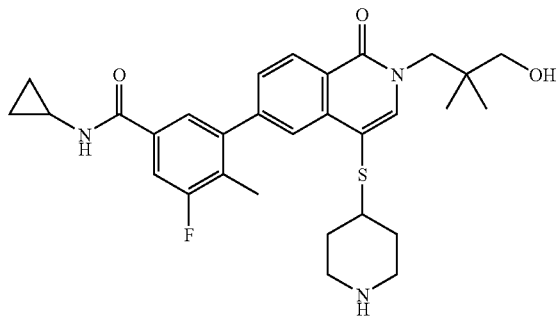

a) 6-Bromo-4-sulfanylisoquinolin-1(2H)-one

To a solution of 6-bromo-1-oxo-1,2-dihydroisoquinoline-4-sulfonyl chloride (Example 46a, 1 g) in THF (12 mL) was added triphenylphosphine (2.85 g). After 5 min, water (0.48 mL) was added followed by DMF (0.6 mL) and the reaction stirred for 1 h. Ethyl acetate and 2M HCl (aq) were added and the mixture shaken vigorously. The solid was filtered off and washed with further water and ethyl acetate before drying in vacuo at room temperature is for 2 h to afford the subtitle compound (0.2 g).

MS: APCI(−ve) 254/258 (M−H)⁻.

¹H NMR δ (DMSO-d₆) 11.61 (s, 1H), 8.13 (d, 2H), 7.72 (dd, 1H), 7.42 (d, 1H), 4.87 (s, 1H).

b) tert-Butyl 4-[(6-bromo-1-oxo-1,2-dihydroisoquinolin-4-yl)sulfanyl]piperidine-1-carboxylate To 6-bromo-4-sulfanylisoquinolin-1(2H)-one (Example 58a, 0.62 g) was added tert-butyl 4-[(methylsulfonyl)oxy]piperidine-1-carboxylate (0.676 g) and potassium carbonate (0.769 g). After thoroughly flushing with nitrogen, DMF (6 mL) was added and the reaction stirred at room temperature for 30 min. Further DMF (9 mL) was added, and the reaction stirred at 40° C. for 1 h. Further DMF (10 mL) was added and the reaction stirred at 50° C. for 16 h. The reaction was partitioned between ethyl acetate and water. The aqueous was extracted with further ethyl acetate (3×) and the combined organics were washed with saturated brine (3×100 mL). The organics were dried (MgSO₄), filtered and evaporated under reduced pressure. DCM was added, and the resulting suspension was filtered. The filtrate was concentrated under reduced pressure, dissolved in the minimum volume of DCM and purified (SiO₂ chromatography, elution with 50%-100% diethyl ether/isohexane followed by ethyl acetate flush) to afford the subtitle compound (0.353 g).

MS: APCI(−ve) 437/441 (M−H)⁻.

¹H NMR δ (CDCl₃) 10.20 (s, 1H), 8.34 (d, 1H), 8.28 (d, 1H), 7.67 (dd, 1H), 7.48 (d, 1H), 4.00 (d, 2H), 2.99-2.76 (m, 3H), 1.93-1.80 (m, 2H), 1.44 (s, 9H), 0.92-0.78 (m, 2H).

c) tert-Butyl 4-{[6-bromo-2-(3-{[tert-butyl(dimethyl)silyl]oxy}-2,2-dimethylpropyl)-1-oxo-1,2-dihydroisoquinolin-4-yl]sulfanyl}piperidine-1-carboxylate A mixture of tert-butyl 4-[(6-bromo-1-oxo-1,2-dihydroisoquinolin-4-yl)sulfanyl]piperidine-1-carboxylate (Example 58b, 0.353 g) in DMF (5 mL) was treated with (3-bromo-2,2-dimethylpropoxy)(tert-butyl)dimethylsilane (0.452 g) and cesium carbonate (0.785 g). The mixture was stirred at 80° C. for 16 h, then at 90° C. for 16 h. After cooling to room temperature the reaction mixture was partitioned between water (250 mL) and ethyl acetate (3×250 mL). The combined organics were washed with water (3×200 mL) and brine (3×100 mL), dried (MgSO₄), filtered and concentrated. The crude product was dissolved in the minimum amount of DCM and purified (SiO₂ chromatography, eluting first with isohexane, then 25% diethyl ether/isohexane) to afford the subtitle compound (0.248 g).

MS: APCI(+ve) 640 (M+H)⁺.

d) tert-Butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfanyl)piperidine-1-carboxylate A solution of tert-butyl 4-{[6-bromo-2-(3-{[tert-butyl(dimethyl)silyl]oxy}-2,2-dimethylpropyl)-1-oxo-1,2-dihydroisoquinolin-4-yl]sulfanyl}piperidine-1-carboxylate (Example 58c, 0.248 g) in DMF (4 mL) was treated with N-cyclopropyl-3-fluoro-4-methyl-5-(4,4,5,5-tetramethyl-1,3,2-dioxaborolan-2-yl)benzamide (0.124 g), Pd-118 (0.007 g) and potassium carbonate (0.107 g). The reaction was stirred at 80° C. for 6 h. The reaction mixture was partitioned between ethyl acetate and water. The aqueous was extracted with ethyl acetate (2×100 mL), and the combined organics were washed with water (3×100 mL) and brine (3×100 mL). The organics were dried (MgSO₄), filtered, and evaporated under reduced pressure. The crude product was purified (SiO₂ chromatography, eluting with 10-50% ethyl acetate/isohexane) to afford the subtitle compound (0.123 g).

MS: APCI(−ve) 750 (M−H)⁻.

¹H NMR δ (CDCl₃) 8.50 (d, 1H), 8.01 (d, 1H), 7.71 (s, 1H), 7.51-7.48 (m, 1H), 7.45-7.41 (m, 2H), 6.24-6.20 (m, 1H), 4.03 (s, 1H), 3.32 (s, 1H), 2.22 (d, 3H), 1.87-1.79 (m, 2H), 1.43 (s, 9H), 1.34-1.23 (m, 7H), 0.98 (s, 9H), 0.90-0.84 (m, 4H), 0.64-0.60 (m, 2H), 0.12 (s, 5H), 0.07 (s, 8H).

e) N-Cyclopropyl-3-fluoro-5-[2-(3-hydroxy-2,2-dimethylpropyl)-1-oxo-4-(piperidin-4-ylsulfanyl)-1,2-dihydroisoquinolin-6-yl]-4-methylbenzamide Trifluoroacetic Acid (1 mL) was added to a solution of tert-butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfanyl)piperidine-1-carboxylate (Example 58d, 0.123 g) in DCM (3 mL). The reaction was stirred at room temperature for 30 min. Toluene (5 mL) was added and the volatiles were removed under reduced pressure. The residue was dissolved in MeOH (1 mL)/DMF (1 mL) and purified by preparative HPLC (Xbridge column using a 95-5% gradient of 0.2% aqueous ammonia in acetonitrile) and after solvent removal, the residue was triturated with diethyl ether. This was dissolved in methanol and purified by preparative HPLC (Sunfire C18 column using a 95-30% gradient of 0.1% aqueous formic acid in methanol run over 16 min). The relevant fractions were lyophilized before the solid was dissolved in methanol and passed through a Stratospheres PL-HCO3 cartridge. The solvent was removed from the resulting filtrate under reduced pressure to give, after trituration with diethyl ether, the title compound (0.035 g).

MS: APCI(+ve) 538 (M+H)$^+$.

$^1$H NMR δ (CD$_3$OD) 8.46 (d, 1H), 8.16 (s, 1H), 7.82 (s, 1H), 7.65-7.52 (m, 3H), 4.06 (s, 2H), 3.26 (s, 2H), 3.07-2.94 (m, 3H), 2.92-2.82 (m, 1H), 2.61-2.46 (m, 2H), 2.25 (d, 3H), 1.96-1.84 (m, 2H), 1.61-1.38 (m, 2H), 1.00 (s, 6H), 0.86-0.77 (m, 2H), 0.68-0.61 (m, 2H).

EXAMPLE 59

N-Cyclopropyl-3-fluoro-5-[2-(3-hydroxy-2,2-dimethylpropyl)-1-oxo-4-(piperidin-4-ylsulfinyl)-1,2-dihydroisoquinolin-6-yl]-4-methylbenzamide

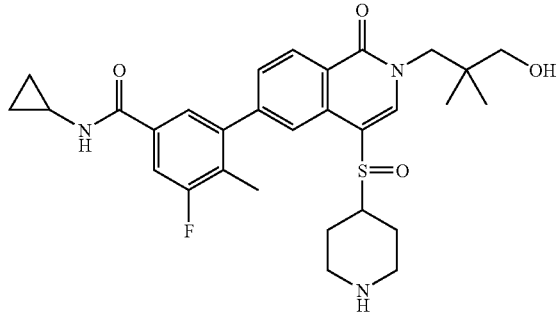

a) tert-Butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfinyl)piperidine-1-carboxylate mCPBA (0.025 g of 77% Max) was added to a solution of tert-butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfanyl)piperidine-1-carboxylate (Example 58d, 0.1 g) in DCM (2 mL). The reaction was stirred at room temperature for 1 h. The reaction was washed with saturated NaHCO$_3$ solution (3×5 mL), then brine (3×5 mL). The organic layer was concentrated under reduced pressure to give the subtitle compound (0.060 g).

MS: APCI(+ve) 768 (M+H)$^+$.

b) N-Cyclopropyl-3-fluoro-5-[2-(3-hydroxy-2,2-dimethylpropyl)-1-oxo-4-(piperidin-4-ylsulfinyl)-1,2-dihydroisoquinolin-6-yl]-4-methylbenzamide Trifluoroacetic Acid (1 mL) was added to a solution of tert-butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfanyl)piperidine-1-carboxylate (Example 59a, 0.06 g) in DCM (2 mL), and the reaction was stirred at room temperature for 30 min. Toluene (10 mL) was added and the volatiles were removed under reduced pressure (repeated 3×). The residue was purified by preparative HPLC (Phenomenex Gemini column using a 95-5% gradient of 0.1% aqueous NH$_3$ in acetonitrile), and after solvent removal and trituration with diethyl ether gave the title compound (0.01 g).

MS: APCI(+ve) 554 (M+H)$^+$.

$^1$H NMR δ (CDCl$_3$) 8.54 (d, 1H), 7.69 (s, 1H), 7.58 (s, 1H), 7.56-7.42 (m, 3H), 6.66 (s, 1H), 4.00 (q, 2H), 3.29-3.11 (m, 4H), 3.10-2.95 (m, 1H), 2.88 (dq, 1H), 2.61 (t, 2H), 2.19 (s, 3H), 1.88-1.59 (m, 5H), 1.02 (s, 6H), 0.91-0.81 (m, 2H), 0.67-0.59 (m, 2H).

EXAMPLE 60

N-Cyclopropyl-3-fluoro-5-[2-(3-hydroxy-2,2-dimethylpropyl)-1-oxo-4-(piperidin-4-ylsulfonyl)-1,2-dihydroisoquinolin-6-yl]-4-methylbenzamide

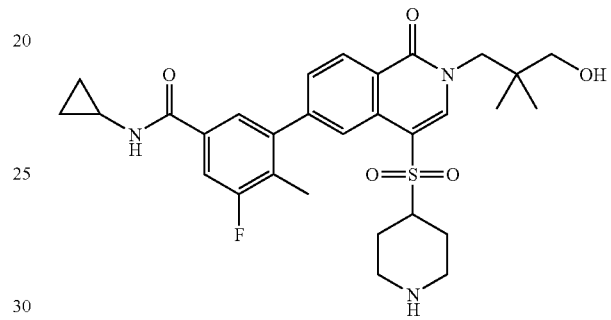

a) tert-Butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)piperidine-1-carboxylate mCPBA (0.023 g of 77% Max) was added to a solution of tert-butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfanyl)piperidine-1-carboxylate (Example 58d, 0.093 g) in DCM (2 mL). The reaction was stirred at room temperature for 1 h. Further mCPBA (0.030 g) was added and the reaction stirred at room temperature for 1 h. The reaction was washed with saturated NaHCO$_3$ solution (3×5 mL), then brine (3×5 mL). The organics were concentrated under reduced pressure to afford the subtitle compound (0.116 g).

MS: APCI(+ve) 684/685/686 (M+H-BOC)$^+$.

b) N-Cyclopropyl-3-fluoro-5-[2-(3-hydroxy-2,2-dimethylpropyl)-1-oxo-4-(piperidin-4-ylsulfonyl)-1,2-dihydroisoquinolin-6-yl]-4-methylbenzamide Trifluoroacetic Acid (1 mL) was added to a solution of tert-butyl 4-({2-(3-{[tert-butyl(dimethyl)silyl]oxy}-2,2-dimethylpropyl)-6-[5-(cyclopropylcarbamoyl)-3-fluoro-2-methylphenyl]-1-oxo-1,2-dihydroisoquinolin-4-yl}sulfonyl)piperidine-1-carboxylate (Example 60a, 0.116 g) in DCM (2 mL), and the reaction was stirred at room temperature for 30 min. The reaction was then azeotroped with toluene (3×10 mL), and the residue dissolved in methanol and purified by preparative HPLC (Phenomenex Gemini column using a 95-5% gradient of 0.2% aqueous NH$_3$ in MeCN).

Solvent removal and trituration with diethyl ether gave the title compound (0.026 g).

MS: APCI(+ve) 570 (M+H)⁺.

¹H NMR δ (CDCl₃) 8.56 (d, 1H), 8.20 (d, 1H), 8.00 (s, 1H), 7.56 (dd, 1H), 7.48 (dd, 1H), 7.46-7.43 (m, 1H), 6.45 (s, 1H), 4.01 (s, 2H), 3.24-3.09 (m, 5H), 2.89 (dq, 1H), 2.56 (td, 2H), 2.21 (d, 3H), 1.98 (d, 2H), 1.71 (qd, 4H), 1.03 (s, 6H), 0.87 (td, 2H), 0.65-0.60 (m, 2H).

EXAMPLE 61

N-Cyclopropyl-3-[2-(cyclopropylmethyl)-1-oxo-4-(piperidin-4-ylsulfanyl)-1,2-dihydroisoquinolin-6-yl]-5-fluoro-4-methylbenzamide

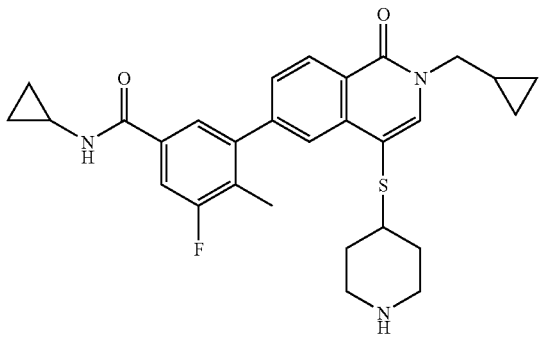

a) tert-Butyl 4-{[6-bromo-2-(cyclopropylmethyl)-1-oxo-1,2-dihydroisoquinolin-4-yl]sulfanyl}piperidine-1-carboxylate The subtitle compound was prepared from tert-butyl 4-[(6-bromo-1-oxo-1,2-dihydroisoquinolin-4-yl)sulfanyl]piperidine-1-carboxylate (Example 58b) and cyclopropylmethyl-bromide using the method of example 58c.

MS: APCI(+ve) 393/395 (M+H)⁺.

¹H NMR δ (DMSO-d₆) 8.22 (d, 1H), 8.19 (d, 1H), 7.99 (s, 1H), 7.74 (dd, 1H), 3.88-3.76 (m, 5H), 2.91-2.76 (m, 1H), 2.08-2.02 (m, 1H), 1.86-1.73 (m, 3H), 1.37 (s, 9H), 0.88-0.79 (m, 2H), 0.51-0.45 (m, 2H), 0.44-0.38 (m, 2H).

b) tert-Butyl 4-({6-[5-(cyclopropylcarbamoyl)-3-fluoro-2-methylphenyl]-2-(cyclopropylmethyl)-1-oxo-1,2-dihydroisoquinolin-4-yl}sulfanyl)piperidine-1-carboxylate The subtitle compound was prepared from tert-Butyl 4-{[6-bromo-2-(cyclopropylmethyl)-1-s oxo-1,2-dihydroisoquinolin-4-yl]sulfanyl}piperidine-1-carboxylate (Example 61a) using the method of example 58d.

MS: APCI(+ve) 506 (M+H-BOC)⁺.

c) N-Cyclopropyl-3-[2-(cyclopropylmethyl)-1-oxo-4-(piperidin-4-ylsulfanyl)-1,2-dihydroisoquinolin-6-yl]-5-fluoro-4-methylbenzamide The title compound was prepared from tert-Butyl 4-({6-[5-(cyclopropylcarbamoyl)-3-fluoro-2-methylphenyl]-2-(cyclopropylmethyl)-1-oxo-1,2-dihydroisoquinolin-4-yl}sulfanyl)piperidine-1-carboxylate (Example 61b) using the method of example 58e.

MS: APCI(+ve) 506 (M+H)⁺.

¹H NMR δ (CD₃OD) 8.41 (d, 1H), 8.13 (d, 1H), 7.83 (s, 1H), 7.60-7.55 (m, 2H), 7.54 (dd, 1H), 3.94 (d, 2H), 2.99 (dt, 2H), 2.96-2.88 (m, 1H), 2.83 (dquintet, 1H), 2.55-2.46 (m, 2H), 2.21 (d, 3H), 1.90-1.82 (m, 2H), 1.48 (ddd, 2H), 1.37-1.25 (m, 1H), 0.78 (td, 2H), 0.64-0.55 (m, 4H), 0.49-0.43 (m, 2).

EXAMPLE 62

N-Cyclopropyl-3-[2-(cyclopropylmethyl)-1-oxo-4-(piperidin-4-ylsulfonyl)-1,2-dihydroisoquinolin-6-yl]-5-fluoro-4-methylbenzamide

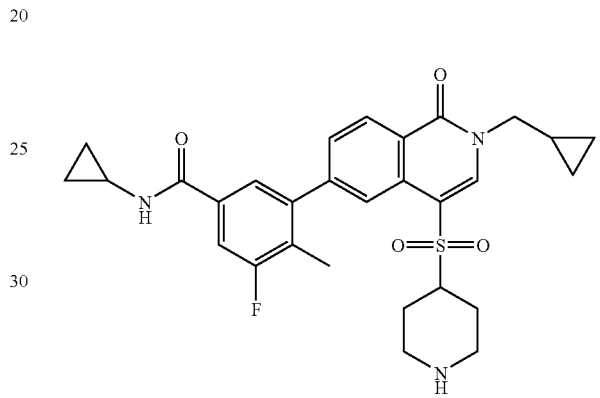

a) tert-Butyl 4-({6-[5-(cyclopropylcarbamoyl)-3-fluoro-2-methylphenyl]-2-(cyclopropylmethyl)-1-oxo-1,2-dihydroisoquinolin-4-yl}sulfonyl)piperidine-1-carboxylate The subtitle compound was prepared from tert-Butyl 4-({6-[5-(cyclopropylcarbamoyl)-3-fluoro-2-methylphenyl]-2-(cyclopropylmethyl)-1-oxo-1,2-dihydroisoquinolin-4-yl}sulfanyl)piperidine-1-carboxylate (Example 61b) using the method of example 60a.

MS: APCI(+ve) 538 (M+H-BOC)⁺.

b) N-Cyclopropyl-3-[2-(cyclopropylmethyl)-1-oxo-4-(piperidin-4-ylsulfonyl)-1,2-dihydroisoquinolin-6-yl]-5-fluoro-4-methylbenzamide The title compound was prepared from tert-Butyl 4-({6-[5-(cyclopropylcarbamoyl)-3-fluoro-2-methylphenyl]-2-(cyclopropylmethyl)-1-oxo-1,2-dihydroisoquinolin-4-yl}sulfonyl)piperidine-1-carboxylate (Example 62a) using the method of example 60b.

MS: APCI(+ve) 538 (M+H)⁺.

¹H NMR δ (CD₃OD) 8.46 (d, 1H), 8.29 (s, 2H), 7.65-7.54 (m, 3H), 4.04 (d, 2H), 3.40-3.27 (m, 1H), 3.11 (d, 2H), 2.90-2.81 (m, 1H), 2.52 (dd, 2H), 2.22 (d, 3H), 1.99 (d, 2H), 1.77-1.60 (m, 2H), 1.43-1.28 (m, 1H), 0.84-0.77 (m, 2H), 0.69-0.61 (m, 4H), 0.54-0.47 (m, 2H).

EXAMPLE 63

N-Cyclopropyl-3-fluoro-5-(2-{[1-(hydroxymethyl)cyclopropyl]methyl}-1-oxo-4-{[(3R)-piperidin-3-ylmethyl]sulfanyl}-1,2-dihydroisoquinolin-6-yl)-4-methylbenzamide

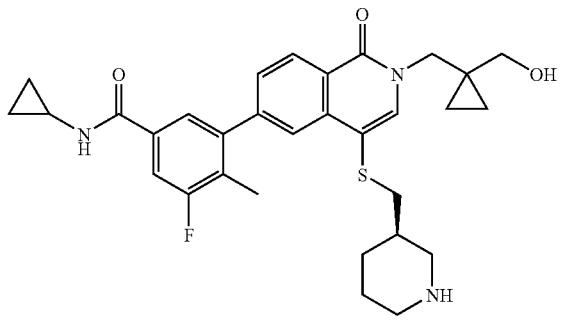

a) 4,4'-disulfanediylbis(6-bromoisoquinolin-1(2H)-one)

To 6-bromo-1-oxo-1,2-dihydroisoquinoline-4-sulfonyl chloride (Example 46a, 3.0 g) in THF (35 mL) was added triphenylphosphine (8.54 g). After 5 min water (1.5 mL) was added followed by DMF (2 mL) and the reaction stirred for 3 h. Ethyl acetate and 2M HCl were added and the mixture stirred vigorously. The solid was filtered off and washed with water and ethyl acetate before drying under vacuum at room temperature for 20 h to afford the subtitle product (2.05 g) as a tan solid.
$^1$H NMR δ(DMSO-$d_6$) 11.76 (d, 2H), 8.12 (d, 2H), 7.85 (d, 2H), 7.69 (dd, 2H), 7.38 (d, 2H).

b) tert-Butyl (3S)-3-{[(methylsulfonyl)oxy]methyl}piperidine-1-carboxylate

Methanesulfonyl chloride (0.48 mL) was added to a solution of (S)-tert-butyl 3-(hydroxymethyl)piperidine-1-carboxylate (1.10 g) and triethylamine (1.42 mL) in DCM (20 mL) at 0° C. under nitrogen. The reaction was stirred for 2 h before being partitioned between DCM (200 mL) and water (100 mL). The organic layer was dried (MgSO$_4$), filtered and evaporated to afford the subtitle product (1.20 g) as a yellow oil.
$^1$H NMR δ(CDCl$_3$) 4.14-4.04 (m, 2H), 4.01-3.88 (m, 1H), 3.85-3.77 (m, 1H), 3.02 (s, 3H), 2.96-2.89 (m, 1H), 2.86-2.70 (m, 1H), 2.01-1.91 (m, 1H), 1.87-1.79 (m, 1H), 1.71-1.63 (m, 1H), 1.54-1.42 (m, 1H), 1.46 (s, 9H), 1.37-1.27 (m, 1H).

c) tert-Butyl (3S)-3-{[(6-bromo-1-oxo-1,2-dihydroisoquinolin-4-yl)sulfanyl]methyl}-piperidine-1-carboxylate Nitrogen was bubbled through a suspension of 4,4'-disulfanediylbis(6-bromoisoquinolin-1(2H)-one) (Example 63a, 140 mg) in ethanol (15 mL) for 20 min. Sodium borohydride (24 mg) was added at room temperature and the mixture was stirred for 10 min before heating at 45° C. for 1 h to afford an orange solution. A degassed solution of tert-Butyl (3S)-3-{[(methylsulfonyl)oxy]methyl}piperidine-1-carboxylate (Example 63b, 177 mg) in acetonitrile (3 mL) was added as a single portion at 45° C. and the reaction stirred for 2 h. The volatiles were removed in vacuo, the residue suspended in DCM and filtered. The filtrate was purified (SiO$_2$ chromatography, elution gradient 10 to 50% ethyl acetate in isohexane) to afford the subtitle product (190 mg) as an orange gum.
MS: APCI(−ve) 452 (M−H)$^+$.

d) tert-Butyl (3S)-3-{[(6-bromo-2-{[1-({[tert-butyl(dimethyl)silyl]oxy}methyl)-cyclopropyl]methyl}-1-oxo-1,2-dihydroisoquinolin-4-yl)sulfanyl]methyl}piperidine-1-carboxylate tert-Butyl (3S)-3-{[(6-bromo-1-oxo-1,2-dihydroisoquinolin-4-yl)sulfanyl]methyl}-piperidine-1-carboxylate (Example 63c, 190 mg) was reacted with [1-({[tert-butyl(dimethyl)silyl]oxy}methyl)cyclopropyl]methyl methanesulfonate (136 mg) by the method of Example 58c to afford the subtitle compound (110 mg) as a colourless oil.
MS: APCI(+ve) 652 (M+H)$^+$.

e) tert-Butyl (3R)-3-{[(2-{[1-({[tert-butyl(dimethyl)silyl]oxy}methyl)-cyclopropyl]methyl}-6-[5-(cyclopropylcarbamoyl)-3-fluoro-2-methylphenyl]-1-oxo-1,2-dihydroisoquinolin-4-yl)sulfanyl]methyl}piperidine-1-carboxylate tert-Butyl (3S)-3-{[(6-bromo-2-{[1-({[tert-butyl(dimethyl)silyl]oxy}methyl)-cyclopropyl]methyl}-1-oxo-1,2-dihydroisoquinolin-4-yl)sulfanyl]methyl}piperidine-1-carboxylate (Example 63d, 109 mg) was reacted with N-cyclopropyl-3-fluoro-4-methyl-5-(4,4,5,5-tetramethyl-1,3,2-dioxaborolan-2-yl)benzamide (45 mg) by the method of Example 58d to afford the subtitle compound (110 mg) as a colourless oil.
MS: APCI(+ve) 665 (M+H−Boc)$^+$.

f) N-Cyclopropyl-3-fluoro-5-(2-{[1-(hydroxymethyl)cyclopropyl]methyl}-1-oxo-4-{[(3R)-piperidin-3-ylmethyl]sulfanyl}-1,2-dihydroisoquinolin-6-yl)-4-methylbenzamide A solution of tert-Butyl (3R)-3-{[(2-{[1-({[tert-butyl(dimethyl)silyl]oxy}methyl)-cyclopropyl]methyl}-6-[5-(cyclopropylcarbamoyl)-3-fluoro-2-methylphenyl]-1-oxo-1,2-dihydroisoquinolin-4-yl)sulfanyl]methyl}piperidine-1-carboxylate (Example 63e, 110 mg) in 4N HCl in dioxane (1 mL) and ethanol (3 mL) was stirred for 20 h before being concentrated in vacuo. The residue was dissolved in methanol (2 mL) and loaded onto a 10 g SCX cartridge. The impurities were washed through with methanol (50 mL) and discarded. The product was eluted with 1N methanolic ammonia (50 mL) and evaporated in vacuo to afford the title product (63 mg) as a white solid.
MS: APCI(+ve) 550 (M+H)$^+$.
$^1$H NMR δ(DMSO-$d_6$) 8.54 (d, 1H), 8.37 (d, 1H), 7.94 (d, 2H), 7.68 (d, 2H), 7.59 (d, 1H), 4.13 (d, 1H), 4.03 (d, 1H), 3.27-3.14 (m, 4H), 3.07-2.98 (m, 1H), 2.88-2.81 (m, 1H), 2.69-2.54 (m, 2H), 2.53-2.37 (m, 3H), 2.19 (s, 3H), 1.89-1.80 (m, 1H), 1.73-1.60 (m, 2H), 1.50-1.37 (m, 1H), 1.20-1.08 (m, 1H), 0.74-0.62 (m, 4H), 0.59-0.53 (m, 2H), 0.45 (s, 2H).

The following Examples 64 to 66 (Table 8) were prepared from 4,4'-disulfanediylbis(6-bromoisoquinolin-1(2H)-one) (Example 63a), using a suitable alkylating agent (for R1) and a suitable (protected) amine (for Y) using similar methods to those described for Example 63:

EXAMPLE 64

N-Cyclopropyl-3-fluoro-5-[2-{[1-(hydroxymethyl)cyclopropyl]methyl}-1-oxo-4-(piperidin-4-ylsulfanyl)-1,2-dihydroisoquinolin-6-yl]-4-methylbenzamide

EXAMPLE 65

N-Cyclopropyl-3-fluoro-5-{2-(3-hydroxy-2,2-dimethylpropyl)-1-oxo-4-[(3R)-pyrrolidin-3-ylsulfanyl]-1,2-dihydroisoquinolin-6-yl}-4-methylbenzamide

EXAMPLE 66

N-Cyclopropyl-3-fluoro-5-{2-[3-hydroxy-2-(hydroxymethyl)-2-methylpropyl]-1-oxo-4-(piperidin-4-ylsulfanyl)-1,2-dihydroisoquinolin-6-yl}-4-methylbenzamide

TABLE 8

| Example | R1 | Y | MS m/z [M + H]+ | 1H NMR δ (DMSO-d6) |
|---|---|---|---|---|
| 64 | 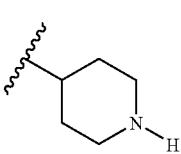 |  | 536 | 8.54(d, 1H), 8.37(d, 1H), 8.02 (d, 1H), 7.88(s, 1H), 7.71-7.64 (m, 2H), 7.61-7.58(m, 1H), 4.72 (s, 1H), 4.09(s, 2H), 3.35-3.27 (m, 1H), 3.23(s, 2H), 2.97-2.82 (m, 4H), 2.40(t, 2H), 2.21(d, 3H), 1.77(d, 2H), 1.40-1.29(m, 2H), 0.73-0.67(m, 4H), 0.59-0.55(m, 2H), 0.45(s, 2H) |
| 65 | 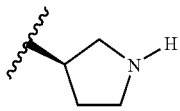 | 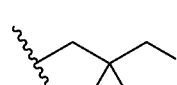 | 524 | 8.54(d, 1H), 8.38(d, 1H), 8.03 (d, 1H), 7.86(s, 1H), 7.71-7.65 (m, 2H), 7.60(dd, 1H), 4.89(s, 1H), 3.97(s, 2H), 3.43-3.36(m, 1H), 3.18-3.13(m, 3H), 2.92 (dd, 1H), 2.89-2.83(m, 1H), 2.76-2.70(m, 1H), 2.63(dd, 1H), 2.20(d, 3H), 2.00-1.90(m, 1H), 1.60-1.52(m, 1H), 0.88(s, 6H), 0.72-0.67(m, 2H), 0.59-0.54(m, 2H) |
| 66 | 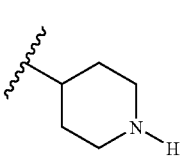 | | 554 | 8.35(d, 1H), 8.38(d, 1H), 8.03 (d, 1H), 7.85(s, 1H), 7.71-7.65 (m, 2H), 7.61(dd, 1H), 4.73(t, 2H), 4.01(s, 2H), 3.29-3.16(m, 4H), 2.97-2.83(m, 4H), 2.42-2.34(m, 2H), 2.21(d, 3H), 1.80-1.71(m, 2H), 1.39-1.28(m, 2H), 0.81(s, 3H), 0.72-0.67(m, 2H), 0.59-0.54(m, 2H) |

EXAMPLE 67

N-Cyclopropyl-3-fluoro-5-[2-(3-hydroxy-2,2-dimethylpropyl)-4-{[(2S,4S)-2-(hydroxymethyl)piperidin-4-yl]sulfanyl}-1-oxo-1,2-dihydroisoquinolin-6-yl]-4-methylbenzamide

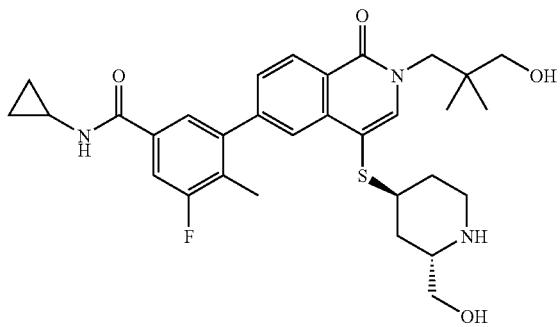

a) (1S,5R)-2-[(1R)-1-Phenylethyl]-6-oxa-2-azabicyclo[3.2.1]octan-7-one

Glyoxylic acid (7.43 mL) was added dropwise to a solution of (R)—N-(1-phenylethyl)but-3-en-1-amine (7.80 g) in tetrahydrofuran (30 mL) at 60° C. over a period of 1.5 h. The reaction was heated at 60° C. for a further 7 h. Water (30 mL) and brine (30 mL) were added and the pH adjusted with 2M NaOH solution to pH 9. The aqueous was extracted with ethyl acetate (3×50 mL), the organics combined, washed with saturated aqueous NaHCO$_3$ solution, water, brine, dried (MgSO$_4$), filtered and evaporated to afford an orange oil (9.5 g). Purification (SiO$_2$ chromatography using elution gradient 25% ethyl acetate in isohexane) afforded the subtitle product (3.10 g) as an orange oil.

$^1$H NMR δ(CDCl$_3$) 7.41-7.23 (m, 5H), 4.77 (t, 1H), 3.70 (q, 1H), 3.34 (dd, 1H), 3.19 (d, 1H), 2.47 (td, 1H), 2.12-2.03 (m, 2H), 1.95-1.86 (m, 1H), 1.82 (d, 1H), 1.33 (d, 3H).

b) tert-Butyl (2S,4R)-4-hydroxy-2-(hydroxymethyl)piperidine-1-carboxylate

A solution of (1S,5R)-2-[(1R)-1-Phenylethyl]-6-oxa-2-azabicyclo[3.2.1]octan-7-one (Example 67a, 3.10 g) in methanol (30 mL) was treated with 4M HCl in dioxane (3.35 mL), added to a paste of 20% palladium hydroxide on carbon (0.50 g) in methanol (5 mL) and stirred under an atmosphere of hydrogen (3 bar) for 20 h. The reaction was filtered and the solid washed with methanol (3×20 mL) and combined filtrates concentrated in vacuo. The residue was suspended in DCM (70 mL) and treated with triethylamine (2.80 mL). BOC-anhydride (3.42 mL) was added to the solution at room temperature and stirred for 20 h before the volatiles were removed in vacuo. Purification (SiO$_2$ chromatography, elution gradient 50 to 80% ethyl acetate in isohexane) afforded the subtitle product (3.40 g) as a colorless oil.

$^1$H NMR δ(CDCl$_3$) 4.87-4.62 (m, 1H), 4.17-4.14 (m, 1H), 3.94-3.77 (m, 1H), 3.74 (s, 3H), 3.45-3.24 (m, 2H), 2.42 (d, 1H), 1.91 (ddd, 1H), 1.78-1.64 (m, 2H), 1.60 (s, 1H), 1.47 (s, 9H).

c) tert-Butyl (2S,4R)-4-hydroxy-2-(hydroxymethyl)piperidine-1-carboxylate

Sodium borohydride (3.28 g) was added portionwise to a solution of tert-Butyl (2S,4R)-4-hydroxy-2-(hydroxymethyl) piperidine-1-carboxylate (Example 67b, 3.40 g) in ethanol (200 mL) at 0° C. The cooling bath was removed after 1 h and the reaction stirred for 20 h before the addition of 1M NaOH solution (25 mL). The mixture was concentrated in vacuo. Water and ethyl acetate were added and the organic layer (and 2 further extracts) were dried and volatiles removed in vacuo. Purification (SiO$_2$ chromatography, elution gradient 50% ethyl acetate in isohexane) gave a colorless oil (2.31 g) which was diluted with DMF (40 mL). TBDPS-Cl (3.60 mL) and imidazole (2.04 g) were added to this solution at room temperature and the reaction stirred for 20 h before being evaporated to dryness. Purification (SiO$_2$ chromatography, elution gradient 35% ethyl acetate in isohexane) afforded the subtitle product (3.50 g) as a colorless oil.

MS: APCI(+ve) 370 (M+H-Boc)$^+$.

d) tert-Butyl (2S,4R)-2-({[tert-butyl(diphenyl)silyl]oxy}methyl)-4-[(methylsulfonyl)-oxy]piperidine-1-carboxylate tert-Butyl (2S,4R)-4-hydroxy-2-(hydroxymethyl)piperidine-1-carboxylate (Example 67c, 1.0 g) was reacted with methanesulfonyl chloride (0.50 mL) using the method of Example 63b to afford the subtitle compound (1.10 g) as a yellow oil.

$^1$H NMR δ(CDCl$_3$) 7.66 (ddd, 4H), 7.45-7.35 (m, 6H), 5.06 (t, 1H), 4.48-4.40 (m, 1H), 4.00-3.93 (m, 1H), 3.77 (quintet, 2H), 2.99-2.90 (m, 1H), 2.79 (s, 3H), 2.32-2.25 (m, 1H), 1.99-1.92 (m, 1H), 1.91-1.84 (m, 1H), 1.82-1.73 (m, 1H), 1.42 (s, 9H), 1.06 (s, 9H).

e) tert-Butyl (2S,4S)-4-[(6-bromo-1-oxo-1,2-dihydroisoquinolin-4-yl)sulfanyl]-2-({[tert-butyl(diphenyl)silyl]oxy}methyl)piperidine-1-carboxylate Sodium borohydride (97 mg) was added to a degassed solution of 6-bromo-4-sulfanylisoquinolin-1(2H)-one (Example 58a, 0.54 g) in ethanol (20 mL) at room temperature with effervescence. The resulting mixture was stirred at room temperature for 10 min before being heating to 85° C. A degassed solution of tert-Butyl (2S,4R)-2-({[tert-butyl(diphenyl)silyl]oxy}methyl)-4-[(methylsulfonyl)-oxy]piperidine-1-carboxylate (Example 67d, 1.17 g) in ethanol (3 mL) and potassium carbonate (0.353 g) were added to the orange solution and the reaction was heated for 1 h, cooled to room temperature and concentrated in vacuo. Purification (SiO$_2$ chromatography, elution gradient 25% to 40% ethyl acetate in isohexane) afforded the subtitle product (0.68 g) as a white foam.

MS: APCI(-ve) 705, 707 (M-H)$^+$.

f) N-Cyclopropyl-3-fluoro-5-[2-(3-hydroxy-2,2-dimethylpropyl)-4-{[(2S,4S)-2-(hydroxymethyl)piperidin-4-yl]sulfanyl}-1-oxo-1,2-dihydroisoquinolin-6-yl]-4-methylbenzamide tert-Butyl (2S,4S)-4-[(6-bromo-1-oxo-1,2-dihydroisoquinolin-4-yl)sulfanyl]-2-({[tert-butyl(diphenyl)silyl]oxy}methyl)piperidine-1-carboxylate (Example 67e, 0.68 g) and 3-(tert-butyldimethylsilyloxy)-2,2-dimethylpropyl methanesulfonate (0.315 g) were reacted by the method of Example 58c to afford crude tert-butyl (2S,4S)-4-{[6-bromo-2-(3-{[tert-butyl(dimethyl)silyl]oxy}-2,2-dimethylpropyl)-1-oxo-1,2-dihydroisoquinolin-4-yl]sulfanyl}-2-({[tert-butyl (diphenyl)silyl]oxy}methyl)piperidine-1-carboxylate (0.87 g) as a colourless oil. This was reacted with N-cyclopropyl-3-fluoro-4-methyl-5-(4,4,5,5-tetramethyl-1,3,2-dioxaborolan-2-yl)benzamide (0.306 g) by the method of Example 58d to afford tert-butyl (2S,4S)-4-({2-(3-{[tert-butyl(dimethyl)silyl]oxy}-2,2-dimethylpropyl)-6-[5-(cyclo-ropylcarbamoyl)-3-fluoro-2-methylphenyl]-1-oxo-1,2-dihydroisoquinolin-4-yl}sulfanyl)-2-({[tert-butyl(diphenyl)silyl]oxy}methyl)piperidine-1-carboxylate as a colourless oil. This was diluted with ethanol (3 mL) and treated with 4M HCl in dioxane (1 mL) and stirred at room temperature for 20 h. The volatiles were removed in vacuo. The crude material was dissolved in methanol (2 mL) and loaded on to a 10 g SCX cartridge. The impurities were washed through with methanol (50 mL) and discarded. The product was eluted with 1N methanolic ammonia (75 mL) and the solvents evaporated in vacuo. Purification by preparative HPLC (Gemini-NX C18 column using a 95-5% gradient of aqueous 0.1% ammonia in methanol as eluent) afforded the title compound (32 mg) as a white solid.

MS: APCI(−ve) 568 (M+H)+.

$^1$H NMR δ(DMSO-d$_6$) 8.53 (d, 1H), 8.37 (d, 1H), 7.99 (d, 1H), 7.81 (s, 1H), 7.68 (d, 1H), 7.66 (d, 1H), 7.60 (dd, 1H), 4.86 (t, 1H), 4.49 (t, 1H), 3.96 (d, 2H), 3.39-3.35 (m, 1H), 3.26-3.18 (m, 1H), 3.14 (d, 2H), 2.98-2.82 (m, 2H), 2.76-2.69 (m, 1H), 2.20 (d, 3H), 2.07 (s, 3H), 1.75-1.40 (m, 4H), 0.87 (s, 6H), 0.70 (dd, 2H), 0.57 (dd, 2H).

Salt Forms and Physical Form Data

DESCRIPTION OF FIGURES

FIG. 1: X-ray powder diffraction pattern of Example 26 Free Base Form A

FIG. 2: X-ray powder diffraction pattern of Example 26 Free Base Form B

FIG. 3: X-ray powder diffraction pattern of Example 26 Free Base Form C

FIG. 4: X-ray powder diffraction pattern of Example 26 Acetate Salt Form A

FIG. 5: X-ray powder diffraction pattern of Example 26 Dihydrobromide Salt Form A FIG. 6: X-ray powder diffraction pattern of Example 26 Free Base Form D

INSTRUMENT DETAILS

XRPD data were collected using a PANalytical CubiX PRO machine unless otherwise stated.

XRPD—PANalytical CubiX PRO

Data was collected with a PANalytical CubiX PRO machine in q-2q configuration over the scan range 2° to 40° 2q with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

Where stated, XRPD data were also collected using a PANalytical X'pert machine.

XRPD—PANalytical X'pert

Data was collected with a PANalytical X'pert machine in q-2q configuration over the scan range 2° to 40° 2q with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

Preparation and Analysis of Example 26 Free Base: N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide Crystalline Form A A crystalline sample of N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide form A was obtained by slurrying amorphous N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide (obtained from example 26 h) in a range of solvents at different temperatures followed by analysis by XRPD.

The slurry conditions that produced polymorph A were:

Approximately 60 μl of acetonitrile/dibutyl ether solvent mixture (1:4 mixture) was added to approximately 9 mg of amorphous compound (example 26 h) and then the mixture was slurried at room temperature for 7 days using a magnetic stirrer.

Approximately 60 μl of acetonitrile/dibutyl ether solvent mixture (1:4 mixture) was added to approximately 11 mg of amorphous compound (example 26 h) and then the mixture was slurried at 40° C. (±5° C.) for 7 days using a magnetic stirrer.

Approximately 30 μl of methanol/dibutyl ether solvent mixture (1:4 mixture) was added to approximately 9 mg of amorphous compound (example 26 h) and then the mixture was slurried at room temperature for 7 days using a magnetic stirrer.

Approximately 30 μl of methanol/dibutyl ether solvent mixture (1:4 mixture) was added to approximately 9 mg of amorphous compound (example 26 h) and then the mixture was slurried at 40° C. (±5° C.) for 7 days using a magnetic stirrer.

Approximately 80 μl of ethanol/dibutyl ether solvent mixture (1:4 mixture) was added to approximately 9 mg of amorphous compound (example 26 h) and then the mixture was slurried at room temperature for 7 days using a magnetic stirrer.

Approximately 80 μl of ethanol/dibutyl ether solvent mixture (1:4 mixture) was added to approximately 9 mg of amorphous compound (example 26 h) and then the mixture was slurried at 40° C. (±5° C.) for 7 days using a magnetic stirrer.

Larger Scale Preparation of N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide crystalline form A Amorphous N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide (2.2 g made using the procedure described in example 26 h) was slurried in 4:1 dibutyl ether:acetonitrile (40 mL) at room temperature for 3 days. The solid was filtered off and re-suspended in heptane (40 mL), stirred at room temperature for 3 days, filtered off and dried in vacuo at 40° C. to give the title compound (1.22 g).

MS: APCI(+ve) 535 (M+H)+.

¹H NMR δ(DMSO-d₆) 8.52 (d, 1H), 8.35 (d, 1H), 8.05 (d, 1H), 7.71-7.63 (m, 2H), 7.56 (dd, 1H), 7.38 (s, 1H), 4.86 (t, 1H), 4.15 (d, 1H), 3.92 (q, 2H), 3.12 (d, 2H), 3.02 (d, 1H), 2.93-2.80 (m, 1H), 2.79-2.59 (m, 2H), 2.59-2.44 (m, 2H), 2.40-2.31 (m, 2H), 2.27 (d, 3H), 2.04-1.89 (m, 1H), 1.09-1.05 (m, 3H), 0.87 (s, 6H), 0.74-0.65 (m, 2H), 0.60-0.52 (m, 2H).

An XRPD diffraction pattern of Example 26 free base crystalline form A is presented in FIG. 1.

Preparation and Analysis of Example 26 Free Base: N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide Crystalline Form B A crystalline sample of N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide form B was obtained by slurrying amorphous N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide obtained from example 26 h in ethyl acetate at different temperatures followed by analysis by XRPD.

The slurry conditions that produced form B were:

Approximately 20 μl of ethyl acetate was added to approximately 9 mg of amorphous compound (example 26 h) and then the mixture was slurried at room temperature for 7 days using a magnetic stirrer.

Approximately 15 μl of ethyl acetate was added to approximately 9 mg of amorphous compound (example 26 h) and then the mixture was slurried at 40° C. (±5° C.) for 7 days using a magnetic stirrer.

An XRPD diffraction pattern of Example 26 free base crystalline form B is presented in FIG. 2.

Preparation and Analysis of Example 26 Free Base: N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide Crystalline Form C A crystalline sample of N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide form C was obtained by slurrying amorphous N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide obtained from example 26 h in 2-butanone at different temperatures followed by analysis by XRPD.

The slurry conditions that produced form C were:

Approximately 10 μl of 2-butanone was added to approximately 9 mg of amorphous compound (example 26 h) and then the mixture was slurried at room temperature for 7 days using a magnetic stirrer.

Approximately 10 μl of 2-butanone was added to approximately 9 mg of amorphous compound (example 26 h) and then the mixture was slurried at 40° C. (±5° C.) for 7 days using a magnetic stirrer.

An XRPD diffraction pattern of Example 26 free base crystalline form C is presented in FIG. 3.

Preparation and Analysis of Example 26 Acetate Salt: N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide Acetate Crystalline Form A N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide[1] (0.10 g) was dissolved in methanol (2 mL), treated with acetic acid (0.11 mL) and the volatiles removed in vacuo. Toluene (5-10 mL) was added and the volatiles were removed in vacuo and this process was repeated an additional 3 times to obtain a solid which was triturated in acetone (3 mL) at room temperature for 7 days, filtered off and dried in vacuo at 40° C. for 48 h to give the title compound (0.08 g).

[1] Purity greater than 98% as determined by HPLC/UV.

MS: APCI(+ve) 535 (M+H)+.

¹H NMR δ(DMSO-d₆) 8.52 (d, 1H), 8.35 (d, 1H), 8.04 (d, 1H), 7.71-7.64 (m, 2H), 7.57 (dd, 1H), 7.39 (s, 1H), 4.16 (d, 1H), 3.97 (d, 1H), 3.87 (d, 1H), 3.12 (s, 2H), 3.03 (d, 1H), 2.91-2.78 (m, 2H), 2.72-2.64 (m, 1H), 2.58-2.52 (m, 1H-2H part obscured by DMSO) 2.43-2.32 (m, 2H), 2.27 (d, 3H), 2.06-1.95 (m, 1H), 1.90 (s, 3H), 1.08 (d, 3H), 0.87 (s, 6H), 0.74-0.66 (m, 2H), 0.59-0.52 (m, 2H).

Elemental Analysis—Found (calculated): % C, 65.5 (66.7); H, 7.3 (7.3); N, 9.3 (9.4).

Karl Fischer Analysis: 1.2% water.

The ratio of acetate to N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide was determined as being 1:1 by NMR.

A larger scale preparation of the acetate salt was also carried out:

N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide[1] (2 g) was dissolved in methanol (10 mL), treated with acetic acid (1.1 mL) and the volatiles removed in vacuo. Toluene (30-50 mL) was added and the volatiles were removed in vacuo and this process was repeated an additional 3 times to obtain a solid which was triturated in acetone (30 mL) at RT for 7 days, filtered off and dried in vacuo at 40° C. for 48 h to give the title compound (1.95 g).

[1] Purity greater than 98% as determined by HPLC/UV.

MS: APCI(+ve) 535 (M+H)+.

¹H NMR δ(DMSO-d₆) 8.52 (d, 1H), 8.35 (d, 1H), 8.04 (d, 1H), 7.71-7.64 (m, 2H), 7.57 (dd, 1H), 7.39 (s, 1H), 4.16 (d, 1H), 3.97 (d, 1H), 3.87 (d, 1H), 3.12 (s, 2H), 3.03 (d, 1H), 2.91-2.81 (m, 1H), 2.78 (d, 1H), 2.72-2.64 (m, 1H), 2.58-2.52 (m, 1H-2H part obscured by DMSO) 2.43-2.32 (m, 2H), 2.27 (d, 3H), 2.06-1.95 (m, 1H), 1.90 (s, 3H), 1.08 (d, 3H), 0.87 s, 6H), 0.74-0.66 (m, 2H), 0.59-0.52 (m, 2H).

Elemental Analysis—Found (calculated): % C, 65.9 (66.7); H, 7.3 (7.3); N, 9.4 (9.4)

Karl Fischer Analysis: 0.2% water.

The ratio of acetate to N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide was determined as being 1:1 by NMR.

A sample of N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide acetate salt crystalline form A obtained as described above was slurried in a variety of solvents at room temperature which resulted in no change of crystalline form. The details of the conditions for the slurries are given below:

Approximately 90 μl of heptane was added to approximately 16 mg of the crystalline acetate salt and then the mixture was slurried at room temperature for 7 days using a magnetic stirrer.

Approximately 100 μl of ethyl acetate was added to approximately 15 mg of crystalline acetate salt and then the mixture was slurried at room temperature for 7 days using a magnetic stirrer.

Approximately 100 μl of acetonitrile was added to approximately 9 mg of crystalline acetate salt and then the mixture was slurried at room temperature for 7 days using a magnetic stirrer.

Approximately 200 μl of 0.9% NaCl (aq) was added to approximately 16 mg of crystalline acetate salt and then the mixture was slurried at room temperature for 7 days using a magnetic stirrer.

An XRPD diffraction pattern of Crystalline Form A of Example 26 Acetate Salt is presented in FIG. 4.

Preparation and Analysis of Example 26 Dihydrobromide Salt: N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide Dihydrobromide Crystalline Form A N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide (2 g) was dissolved in 2-propanol (30 mL) at 0° C. and treated dropwise with HBr (1.69 mL of a 48% solution in acetic acid), allowed to warm to room temperature and stirred for 5 days. The resulting solid was filtered off and dried in vacuo at 40° C. for 48 h to give the title compound (1.35 g). [N.B. the use of methanol at room temperature in place of 2-propanol at 0° C. for this salt formation led to ~4% decomposition].

MS: APCI(+ve) 535 (M+H)$^+$.

$^1$H NMR δ(CD$_3$OD) 8.47 (d, 1H), 7.97 (s, 1H), 7.75 (s, 2H), 7.63-7.55 (m, 2H), 4.10 (d, 1H), 4.00 (d, 1H), 3.93-3.86 (m, 1H), 3.65-3.32 (m, 4H), 3.24 (s, 2H), 3.16-2.95 (m, 2H), 2.90-2.81 (m, 1H), 2.24 (s, 3H), 1.62-1.52 (m, 3H), 1.13 (d, 2H), 0.98 (s, 6H), 0.82-0.75 (m, 2H), 0.69-0.63 (m, 2H).

Elemental Analysis—Found (calculated): %: C, 53.1 (53.2); H, 6.2 (6.0); N, 7.7 (8.0).

Karl Fischer Analysis: 0.1% water.

The ratio of hydrobromide to N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide was confirmed as being 2:1 by elemental analysis.

An XRPD diffraction pattern of Crystalline Form A of Example 26 Dihydrobromide Salt is presented in FIG. 5. This was generated using the PANalytical X'pert machine.

Preparation and Analysis of Example 26 Free Base: N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide Crystalline Form D 3-Bromo-2,2-dimethylpropyl pivalate 3-Bromo-2,2-dimethyl-1-propanol (26.9 mL), 4-(dimethylamino)pyridine (2.67 g), and triethylamine (33.5 mL) were dissolved in toluene (250 mL) and cooled to 0° C. Pivaloyl chloride was added dropwise over 30 min (temperature rose to 15° C.) and upon completion the reaction was allowed to warm to 23° C. and stirred for 1 h. The reaction was filtered and the filtrate washed with 2N aqueous HCl (250 mL), aqueous sodium hydrogencarbonate solution (250 mL) and aqueous brine (250 mL). The organic layer was separated and the solvent evaporated to give the subtitle compound (53.0 g).

$^1$H NMR δ(CDCl$_3$) 3.91 (s, 2H), 3.35 (s, 2H), 1.22 (s, 9H), 1.07 (s, 6H).

3-(6-Bromo-1-oxoisoquinolin-2(1H)-yl)-2,2-dimethylpropyl pivalate 6-bromoisoquinolin-1(2H)-one (43 g) and 3-bromo-2,2-dimethylpropyl pivalate (53.0 g) were dissolved in DMF (400 mL) and cesium carbonate (125 g, finely ground in a pestle and mortar) was added and the reaction heated at 90° C. for 15 h. After cooling to room temperature the reaction was stirred for 72 h and then poured into water (3 L). The mixture was extracted with tert-butyl methyl ether (2×2.5 L) and the organics combined and washed with aqueous brine (2.5 L). The organics were separated and dried (Na$_2$SO$_4$), filtered and the solvents evaporated. The residue was dissolved in diethyl ether and the resultant solid was filtered off (and discarded). The filtrate was collected, the solvents evaporated and the residue purified (SiO$_2$ chromatography, eluting with 0-15% ethyl acetate/isohexane) to afford the subtitle compound (51.3 g).

$^1$H NMR δ(CDCl$_3$) 8.26 (d, 1H), 7.66 (d, 1H), 7.56 (dd, 1H), 7.02 (d, 1H), 6.35 (d, 1H), 3.99 (s, 2H), 3.90 (s, 2H), 1.24 (s, 9H), 1.03 (s, 6H).

3-(6-Bromo-4-formyl-1-oxoisoquinolin-2(1H)-yl)-2,2-dimethylpropyl pivalate

A stirred solution of 3-(6-bromo-1-oxoisoquinolin-2(1H)-yl)-2,2-dimethylpropyl pivalate (51.3 g) in DMF (150 mL) at 75° C. (flask fitted with a CaCl$_2$ drying tube) was treated dropwise over ~20 min with a freshly prepared solution of Vilsmeyer Haak reagent [freshly prepared by dropwise addition of POCl$_3$ (182 mL) over ~40 min to DMF (302 mL) at 0° C. and then stirred for 1 h at room temperature]. Heating was continued for 8 h, and then the reaction mixture was cooled to room temperature and stirred overnight. The mixture was poured onto ice water (6 L) [CAUTION: exotherm] and extracted with tert-butyl methyl ether (2×2.5 L). The combined organics were washed with 20% w/v aqueous brine (2.5 L), dried (Na$_2$SO$_4$), filtered and concentrated in vacuo. The residue was purified (SiO$_2$ chromatography, eluting with 10% to 20% ethyl acetate/isohexane) to give the subtitle product (41.5 g).

$^1$H NMR δ(CDCl$_3$) 9.70 (s, 1H), 9.21 (d, 1H), 8.26 (d, 1H), 7.69 (dd, 1H), 7.64 (s, 1H), 4.09 (s, 2H), 3.92 (s, 2H), 1.25 (s, 9H), 1.06 (s, 6H).

(3R)-tert-Butyl 4((6-bromo-2-(2,2-dimethyl-3-(pivaloyloxy)propyl)-1-oxo-1,2-dihydroisoquinolin-4-yl)methyl)-3-methylpiperazine-1-carboxylate (3R) tert-Butyl-3-methylpiperazine-1-carboxylate (26.1 g) was dissolved in 2-methyltetrahydrofuran (200 mL) and then magnesium sulfate (57 g) and triethylamine (18.17 mL) were added and the resulting mixture cooled to 0° C. Chlorotrimethylsilane (16.66 mL, freshly distilled from K$_2$CO$_3$ and stored under nitrogen) was added dropwise. The reaction was stirred for 1 h at 23° C., filtered and the filtrate added in one portion to a stirred mixture of 3-(6-bromo-4-formyl-1-oxoisoquinolin-2(1H)-yl)-2,2-dimethylpropyl pivalate (36.7 g), triethylamine (12.11 mL) and magnesium sulfate (57 g) in 2-methyltetrahydrofuran (200 mL). Chlorotrimethylsilane (11.11 mL) was added in one portion and, after stirring for 1 h, sodium triacetoxyborohydride (27.6 g) was added (slight effervescence noted) and the reaction stirred at room temperature overnight. Further sodium triacetoxyborohydride (0.5 equiv) was added and the reaction stirred for 3 days. Sodium borohydride (0.5 eq) was added and after stirring for 30 min, the reaction was quenched with saturated aqueous sodium hydrogencarbonate solution (250 mL) and stirred vigorously for 10 min. The aqueous layer was separated and extracted with 2-methyltetrahydrofuran (200 mL) and the combined organics washed with brine (250 mL), dried ($Na_2SO_4$), filtered and the solvents evaporated to give the subtitle compound (58 g) which was used without additional purification.

MS: APCI(+ve) 608 (M+H)+.

(3R)-tert-Butyl 4-((6-(5-(cyclopropylcarbamoyl)-3-fluoro-2-methylphenyl)-2-(2,2-dimethyl-3-(pivaloyloxy)propyl)-1-oxo-1,2-dihydroisoquinolin-4-yl)methyl)-3-methylpiperazine-1-carboxylate Pd-118 (0.688 g) was stirred in acetonitrile (80 mL) under nitrogen and after 5 min, N-cyclopropyl-3-fluoro-4-methyl-5-(4,4,5,5-tetramethyl-1,3,2-dioxaborolan-2-yl)benzamide (9.26 g) was added. After 5 min, a solution of potassium carbonate (7.29 g) in water (80 mL) was added and after 10 min, a solution of (3R)-tert-butyl 4-((6-bromo-2-(2,2-dimethyl-3-(pivaloyloxy)propyl)-1-oxo-1,2-dihydroisoquinolin-4-yl)methyl)-3-methylpiperazine-1-carboxylate (16 g) in acetonitrile (80 mL) was added and the reaction heated at 70° C. for 1.5 h. After cooling to room temperature, brine (200 mL) was added and the mixture extracted with ethyl acetate (2×125 mL). The combined organics were dried ($Na_2SO_4$), filtered and the solvents evaporated. The residue was purified ($SiO_2$ chromatography, eluting with 20%-35% ethyl acetate/2% triethylamine in isohexane) to give the subtitle compound (14.20 g).

MS: APCI(+ve) 719 (M+H)+.

(3R)-tert-butyl 4-((6-(5-(cyclopropylcarbamoyl)-3-fluoro-2-methylphenyl)-2-(3-hydroxy-2,2-dimethylpropyl)-1-oxo-1,2-dihydroisoquinolin-4-yl)-methyl)-3-methylpiperazine-1-carboxylate (3R)-tert-Butyl 4-((6-(5-(cyclopropylcarbamoyl)-3-fluoro-2-methylphenyl)-2-(2,2-dimethyl-3-(pivaloyloxy)propyl)-1-oxo-1,2-dihydroisoquinolin-4-yl)methyl)-3-methylpiperazine-1-carboxylate (50.8 g) was dissolved in methanol (600 mL) and a solution of potassium carbonate (29.3 g) in water (100 mL) was added. The reaction was heated at reflux (internal temperature 67° C.) for 16 h. After cooling to 50° C., further water was slowly added until the mixture became opaque and the mixture was cooled to 23° C. over 1 h. The precipitate was collected by filtration, washed with water (100 mL) and isohexane (100 mL) and dried in vacuo at 45° C. to give the subtitle product (32.4 g).

$^1$H NMR δ(DMSO-$d_6$) 8.53 (d, 1H), 8.35 (d, 1H), 8.00 (d, 1H), 7.72-7.62 (m, 2H), 7.57 (dd, 1H), 7.41 (s, 1H), 4.87 (t, 1H), 4.05 (d, 1H), 3.92 (dd, 2H), 3.50-3.38 (m, 1H), 3.26 3.16 (m, 2H), 3.12 (d, 2H), 2.99 (s, 1H), 2.90-2.81 (m, 1H), 2.63-2.55 (m, 1H), 2.26 (d, 3H), 2.12 (s, 1H), 1.39 (s, 9H), 1.06 (d, 3H), 0.88 (s, 6H), 0.74-0.64 (m, 2H), 0.58-0.51 (m, 2H).

N-Cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide (3R)-tert-Butyl 4-((6-(5-(cyclopropylcarbamoyl)-3-fluoro-2-methylphenyl)-2-(3-hydroxy-2,2-dimethylpropyl)-1-oxo-1,2-dihydroisoquinolin-4-yl)methyl)-3-methylpiperazine-1-carboxylate (27 g) was dissolved in 2-propanol (200 mL) and HCl (54.1 mL of a 5-6 N solution in 2-propanol) was added. The reaction was heated at 50° C. for 4 h, cooled to room temperature and stirred overnight. The volatiles were evaporated in vacuo and excess HCl removed by addition of toluene followed by solvent removal in vacuo. Water (300 mL) was added followed by the portionwise addition of sodium bicarbonate (7.15 g) until pH 7. Further sodium bicarbonate (7.15 g) was added portionwise and the mixture extracted with DCM (500 mL+200 mL). The combined organics were washed with brine (250 mL), dried ($Na_2SO_4$), filtered and the volatiles evaporated in vacuo to give the title product (22 g).

$^1$H NMR δ(DMSO-$d_6$) 8.54 (d, 1H), 8.36 (dd, 1H), 8.02 (d, 1H), 7.73-7.63 (m, 2H), 7.60-7.55 (m, 1H), 7.41 (s, 1H), 4.88 (s, 1H), 4.18 (d, 1H), 4.01-3.83 (m, 2H), 3.12 (m, 2H), 3.02 (d, 1H), 2.93-2.62 (m, 3H), 2.58-2.45 (m, 2H), 2.42-2.30 (d, 2H), 2.27 (t, 3H), 2.08 (t, 1H), 1.11 (d, 3H), 0.88 (s, 6H), 0.75-0.66 (m, 2H), 0.62-0.52 (m, 2H) (further analysis showed the presence of residual solvents at the following approximate w/w levels: toluene (1.6% w/w), 2-propanol (3.9%) and DCM (0.4%)).

Karl Fischer Analysis: 2.5% water
XRPD showed amorphous form.

A sample of N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide free base crystalline form D was obtained by slurrying amorphous N-cyclopropyl-3-fluoro-5-[2-(3-hydroxy-2,2-dimethylpropyl)-4-{[(2R)-2-methylpiperazin-1-yl]methyl}-1-oxo-1,2-dihydroisoquinolin-6-yl]-4-methylbenzamide (obtained above) in range of solvents at different temperatures followed by analysis by XRPD (using the PANalytical X'pert machine).

The details of the conditions for the slurries/recrystallisations, which produced crystalline form D are given below:—
- Approximately 500 µl of acetone was added to approximately 10 mg of amorphous compound and then the mixture slurried at 50° C. (±5° C.) for 7 days using a magnetic stirrer.
- Approximately 500 µl of THF was added to approximately 10 mg of amorphous compound and then the mixture slurried at 50° C. (±5° C.) for 7 days using a magnetic stirrer.
- Approximately 500 µl of ethyl acetate was added to approximately 10 mg of amorphous compound and then the mixture slurried at 72° C. (±5° C.) for 7 days using a magnetic stirrer.
- Approximately 500 µl of methyl ethyl ketone was added to approximately 10 mg of amorphous compound and then the mixture slurried at 72° C. (±5° C.) for 7 days using a magnetic stirrer.
- Approximately 500 µl of acetonitrile was added to approximately 10 mg of amorphous compound and then the mixture slurried at 72° C. (±5° C.) for 7 days using a magnetic stirrer.

Approximately 500 µl of isopropyl acetate was added to approximately 10 mg of amorphous compound and then the mixture slurried at 77° C. (±5° C.) for 7 days using a magnetic stirrer.

Approximately 500 µl of methyl tert-butyl ketone was added to approximately 10 mg of amorphous compound and then the mixture slurried at 103° C. (±5° C.) for 7 days using a magnetic stirrer.

Approximately 3000 µl of ethyl acetate/diethyl ether (1:4 mixture—ethyl acetate previously made wet by washing with water and then separating) was added to approximately 100 mg of amorphous compound and then the mixture heated to 77° C. (±5° C.) and then left to stir at room temperature for 7 days using a magnetic stirrer.

Approximately 3000 µl of DCM/isohexane (1:4 mixture—DCM previously made wet by washing with water and then separating) was added to approximately 100 mg of amorphous compound and then the mixture heated to 40° C. (±5° C.) and then left to stir at room temperature for 7 days using a magnetic stirrer.

Approximately 3000 µl of ethyl Acetate/isohexane (1:4 mixture—ethyl acetate previously made wet by washing with water and then separating) was added to approximately 100 mg of amorphous compound and then the mixture heated to 77° C. (±5° C.) and then left to stir at room temperature for 7 days using a magnetic stirrer.

Approximately 3000 µl of ethyl acetate (previously made wet by washing with water and then separating) was added to approximately 100 mg of amorphous compound and then slurried at room temperature for 7 days using a magnetic stirrer.

Approximately 3000 µl of dibutylether was added to approximately 100 mg of amorphous compound and then the mixture slurried at room temperature for 7 days using a magnetic stirrer.

Approximately 3000 µl of dibutylether/acetonitrile (4:1 mixture) was added to approximately 100 mg of amorphous compound and then the mixture slurried at room temperature for 7 days using a magnetic stirrer.

Approximately 3000 µl of diisopropylether/acetonitrile (4:1 mixture) was added to approximately 100 mg of amorphous compound and then the mixture slurried at room temperature for 7 days using a magnetic stirrer.

Approximately 3000 µl of ethyl acetate was added to approximately 100 mg of amorphous compound and then the mixture slurried at room temperature for 7 days using a magnetic stirrer.

An XRPD diffraction pattern of Example 26 free base Crystalline Form D is presented in FIG. 6.

The invention claimed is:

1. A compound which is N-Cyclopropyl-3-fluoro-5-[2-(3-hydroxy-2,2-dimethylpropyl)-4-{[(2R)-2-methylpiperazin-1-yl]methyl-1-oxo-1,2-dihydroisoquinolin-6-yl]-4-methylbenzamide or a pharmaceutically acceptable salt or N-oxide thereof.

2. A pharmaceutical composition that comprises the compound of claim 1 or a pharmaceutically acceptable salt or N-oxide thereof and a pharmaceutically acceptable adjuvant, diluent or carrier.

3. A pharmaceutical product comprising, in combination, a first active ingredient which is the compound of claim 1 or a pharmaceutically acceptable salt thereof or N-oxide thereof and at least one further active ingredient selected from:—
    a phosphodiesterase inhibitor;
    a β2 adrenoceptor agonist;
    a modulator of chemokine receptor function;
    a protease inhibitor;
    a steroidal glucocorticoid receptor agonist;
    an anticholinergic agent; and
    a non-steroidal glucocorticoid receptor agonist.

4. A method for the treatment of chronic obstructive pulmonary disease (COPD) in a warm-blooded animal, which comprises administering to said mammal in need of such treatment an effective amount of the compound of claim 1 or a pharmaceutically acceptable salt or N-oxide thereof.

5. A method for the treatment of asthma in a warm-blooded animal, which comprises administering to said mammal in need of such treatment an effective amount of the compound of claim 1 or a pharmaceutically acceptable salt or N-oxide thereof.

* * * * *